(12) United States Patent
Martin López et al.

(10) Patent No.: US 8,501,968 B2
(45) Date of Patent: Aug. 6, 2013

(54) ANTITUMORAL DIHYDROPYRAN-2-ONE COMPOUNDS

(75) Inventors: Ma Jesús Martin López, Madrid (ES); Laura Coello Molinero, Madrid (ES); José Fernando Reyes Benítez, Madrid (ES); Alberto Rodríguez Vicente, Madrid (ES); María Garranzo García-Ibarrola, Madrid (ES); Carmen Murcia Pérez, Madrid (ES); Andrés Francesch Solloso, Madrid (ES); Francisco Sánchez Sancho, Madrid (ES); Maria del Carmen Cuevas Marchante, Madrid (ES); Rogelio Fernández Rodríguez, Madrid (ES)

(73) Assignee: PharmaMar, S.A. (ES)

( * ) Notice: Subject to any disclaimer, the term of this patent is extended or adjusted under 35 U.S.C. 154(b) by 0 days.

(21) Appl. No.: 13/171,567

(22) Filed: Jun. 29, 2011

(65) Prior Publication Data

US 2012/0190870 A1    Jul. 26, 2012

Related U.S. Application Data

(63) Continuation of application No. 12/304,123, filed as application No. PCT/EP2007/055959 on Jun. 15, 2007, now Pat. No. 8,324,406.

(30) Foreign Application Priority Data

Jun. 16, 2006    (EP) .................................... 06380173

(51) Int. Cl.
*C07D 309/30*    (2006.01)
*A01N 43/16*    (2006.01)

(52) U.S. Cl.
USPC ......................................... 549/293; 514/460

(58) Field of Classification Search
USPC ......................................... 549/293; 514/430
See application file for complete search history.

*Primary Examiner* — Nizal Chandrakumar
(74) *Attorney, Agent, or Firm* — Lando & Anastasi LLP

(57) ABSTRACT

Antitumoral compounds obtained from a porifera, of the family Raspailiidae, genus *Lithoplocamia*, species *lithistoides*, and derivatives thereof are provided.

35 Claims, No Drawings

ANTITUMORAL DIHYDROPYRAN-2-ONE COMPOUNDS

CROSS-REFERENCE TO RELATED APPLICATIONS

This patent application is a continuation of U.S. Application No. 12/304,123, filed Jan. 26, 2009, which is the U.S. National Phase of International Application No. PCT/EP2007/055959, filed Jun. 15, 2007, which claims priority to EP 06380173.2, filed June 16, 2006, all of which are incorporated by reference in their entireties.

FIELD OF THE INVENTION

The present invention relates to new antitumoral compounds, pharmaceutical compositions containing them and their use as antitumoral agents.

BACKGROUND OF THE INVENTION

In 1990, Gunasekera S P et al. reported the isolation of a new polyhydroxylated lactone, (+)-discodermolide, from the deep-water Caribbean sponge *Discodermia dissoluta* (Gunasekera S P et al. J. Org. Chem. 1990, 55, 4912-4915 and J. Org. Chem. 1991, 56, 1346).

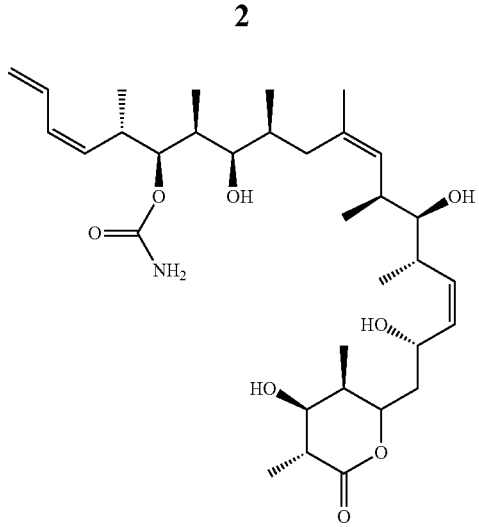

(+)-Discodermolide

This compound has been revealed to be a potent antimitotic agent (Hung D T et al. Chem. Biol. 1996, 3, 287-293 and ter Haar E et al. Biochemistry 1996, 35, 243-250), possessing a mode of action similar to that of the clinically proven anticancer agent paclitaxel (Schiff P B et al. Nature 1979, 277, 665-667). Both natural products arrest the cell cycle at the M phase, promote microtubule formation, and have similar inhibitory effects against breast cancer carcinoma ($IC_{50}$ of 2.4 nM and 2.1 nM, respectively).

On the other hand, some unusual linear dipeptides containing a N-acyl enamide functionality have been isolated from a myxobacteria belonging to the *Chondromyces* genus (Kunze B et al. J. Antibiot. 1994, 47, 881-886 and Jansen R et al. J. Org. Chem. 1999, 1085-1089). Specifically, these compounds are crocacins A, B, C and D and are a group of electron transport inhibitors.

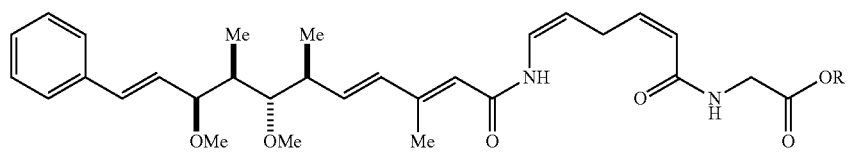

Crocacin A; R = Me
Crocacin B; R = H

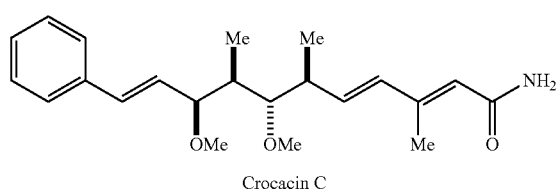

Crocacin C

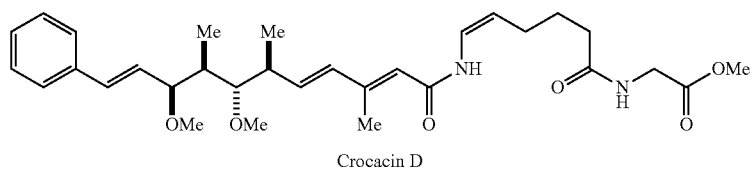

Crocacin D

Crocacins A-D moderately inhibit the growth of a few Gram-positive bacteria and are potent inhibitors of animal cell cultures and several yeasts and fungi. The most active is crocacin D which showed a MIC of 1.4 ng/mL against the fungus *Saccharomyces cerevisiae* and strong toxicity (IC$_{50}$ of 0.06 mg/L) toward L929 mouse fibroblast cell culture.

Cancer is a leading cause of death in animals and humans. Huge efforts have been and are still being undertaken in order to obtain an antitumor agent active and safe to be administered to patients suffering from a cancer. The problem to be solved by the present invention is to provide compounds that are useful in the treatment of cancer.

SUMMARY OF THE INVENTION

In one aspect, the present invention is directed to compounds of general formula I or pharmaceutically acceptable salts, derivatives, tautomers, prodrugs or stereoisomers thereof

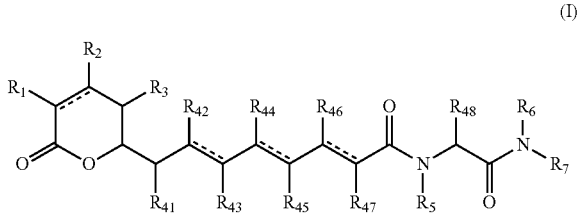

(I)

wherein
R$_1$ is selected from hydrogen, OR$_a$, OCOR$_a$, OCOOR$_a$, NR$_a$R$_b$, NR$_a$COR$_b$, and NR$_a$C(NR$_a$)NR$_a$R$_b$;
each R$_2$ and R$_3$ are independently selected from hydrogen, substituted or unsubstituted C$_1$-C$_{12}$ alkyl, substituted or unsubstituted C$_2$-C$_{12}$ alkenyl and substituted or unsubstituted C$_2$-C$_{12}$ alkynyl;
each R$_{41}$, R$_{42}$, R$_{43}$, R$_{44}$, R$_{45}$, R$_{46}$, R$_{47}$ and R$_{48}$ are independently selected from hydrogen, substituted or unsubstituted C$_1$-C$_{12}$ alkyl, substituted or unsubstituted C$_2$-C$_{12}$ alkenyl and substituted or unsubstituted C$_2$-C$_{12}$ alkynyl;
each R$_5$, R$_6$, and R$_7$ are independently selected from hydrogen, COR$_a$, COOR$_a$, substituted or unsubstituted C$_1$-C$_{12}$ alkyl, substituted or unsubstituted C$_2$-C$_{12}$ alkenyl and substituted or unsubstituted C$_2$-C$_{12}$ alkynyl, or R$_5$ and R$_{48}$ together with the corresponding N atom and C atom to which they are attached may form a substituted or unsubstituted heterocyclic group;
each R$_a$ and R$_b$ are independently selected from hydrogen, substituted or unsubstituted C$_1$-C$_{12}$ alkyl, substituted or unsubstituted C$_2$-C$_{12}$ alkenyl, substituted or unsubstituted C$_2$-C$_{12}$ alkynyl, substituted or unsubstituted aryl and substituted or unsubstituted heterocyclic group; and
each dotted line represent an optional additional bond.

In another aspect, the present invention is directed to compounds of formula I or pharmaceutically acceptable salts, derivatives, tautomers, prodrugs or stereoisomers thereof for use as a medicament, in particular as a medicament for treating cancer.

In a further aspect, the present invention is also directed to the use of compounds of formula I or pharmaceutically acceptable salts, derivatives, tautomers, prodrugs or stereoisomers thereof in the treatment of cancer, or in the preparation of a medicament, preferably for the treatment of cancer. Other aspects of the invention are methods of treatment, and compounds for use in these methods. Therefore, the present invention further provides a method of treating any mammal, notably a human, affected by cancer which comprises administering to the affected individual a therapeutically effective amount of a compound as defined above.

In another aspect, the present invention is directed to pharmaceutical compositions comprising a compound of formula I or pharmaceutically acceptable salts, derivatives, tautomers, prodrugs or stereoisomers thereof together with a pharmaceutically acceptable carrier or diluent.

The present invention also relates to the isolation of the compounds of formula I from a porifera of the family Raspailiidae, genus *Lithoplocamia*, species *lithistoides*, the process for obtaining them and the formation of derivatives from these compounds.

DETAILED DESCRIPTION OF PREFERRED EMBODIMENTS

The present invention relates to compounds of general formula I as defined above.

In these compounds the substituents can be selected in accordance with the following guidance:

Alkyl groups may be branched or unbranched, and preferably have from 1 to about 12 carbon atoms. One more preferred class of alkyl groups has from 1 to about 6 carbon atoms. Even more preferred are alkyl groups having 1, 2, 3 or 4 carbon atoms. Methyl, ethyl, propyl, isopropyl and butyl, including tert-butyl, sec-butyl and isobutyl are particularly preferred alkyl groups in the compounds of the present invention. Another preferred class of alkyl groups has from 6 to about 10 carbon atoms; and even more preferably 7, 8 or 9 carbon atoms. Heptyl, octyl and nonyl are the most preferred alkyl groups of this class.

Preferred alkenyl and alkynyl groups in the compounds of the present invention may be branched or unbranched, have one or more unsaturated linkages and from 2 to about 12 carbon atoms. One more preferred class of alkenyl and alkynyl groups has from 2 to about 6 carbon atoms. Even more preferred are alkenyl and alkynyl groups having 2, 3 or 4 carbon atoms. Another preferred class of alkenyl and alkynyl groups has from 4 to about 10 carbon atoms, still more preferably 6 to about 10 carbon atoms; and even more preferably 7, 8 or 9 carbon atoms.

Suitable aryl groups in the compounds of the present invention include single and multiple ring compounds, including multiple ring compounds that contain separate and/or fused aryl groups. Typical aryl groups contain from 1 to 3 separated or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl.

Suitable heterocyclic groups include heteroaromatic and heteroalicyclic groups containing from 1 to 3 separated or fused rings and from 5 to about 18 ring atoms. Preferably heteroaromatic and heteroalicyclic groups contain from 5 to about 10 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S atoms and include, e.g., pyrrolidinyl, tetrahydrofuranyl, dihydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

The groups above mentioned may be substituted at one or more available positions by one or more suitable groups such as OR', =O, SR', SOR', $SO_2R'$, $NO_2$, NHR', $N(R')_2$, =N—R', NHCOR', $N(COR')_2$, $NHSO_2R'$, NR'C(=NR')NR'R', CN, halogen, COR', COOR', OCOR', OCONHR', $OCON(R')_2$, protected OH, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, $CO_2H$, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list.

Suitable halogen substituents in the compounds of the present invention include F, Cl, Br and I.

Suitable protecting groups for OH are well known for the skill person in the art. A general review of protecting groups in organic chemistry is provided by Wuts, PGM and Greene T W in Protecting Groups in Organic Synthesis, $4^{th}$ Ed. Wiley-Interscience, and by Kocienski P J in Protecting Groups, $3^{rd}$ Ed. Georg Thieme Verlag. These references provide sections on protecting groups for OH. All these references are incorporated by reference in their entirety. Examples of such protected OH include ethers, silyl ethers, esters, sulfonates, sulfenates and sulfinates, carbonates and carbamates. In the case of ethers the protecting group for the OH can be selected from methyl, methoxymethyl, methylthiomethyl, (phenyldimethylsilyl)methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy]methyl, (4-methoxyphenoxy)methyl, guaiacolmethyl, [(p-phenylphenyl)oxy]methyl, t-butoxymethyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethylsilyl)ethoxymethyl, menthoxymethyl, o-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-phenylselenyl)ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienylnitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2-picolyl, 4-picolyl, 3-methyl-2-picolyl N-oxido, 2-quinolinylmethyl, 6-methoxy-2-(4-methylphenyl-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl)methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-dimethoxy-3"-[N-(imidazolylmethyl)]trityl, 4,4'-dimethoxy-3"-[N-(imidazolylethyl) carbamoyl]trityl, bis(4-methoxyphenyl)-1'-pyrenylmethyl, 4-(17-tetrabenzo[a,c,g,i]fluorenylmethyl)-4,4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, and 4,5-bis(ethoxycarbonyl)-[1,3]-dioxolan-2-yl, benzisothiazolyl S,S-dioxido. In the case of silyl ethers the protecting group for the OH can be selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. In the case of esters the protecting group for the OH can be selected from formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, diphenylacetate, 3-phenylpropionate, bisfluorous chain type propanoyl, 4-pentenoate, 4-oxopentanoate, 4,4-(ethylenedithio)pentanoate, 5[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azidobutyrate, (2-azidomethyl)phenylacetate, 2-{[(tritylthio)oxy]methyl}benzoate, 2-{[(4-methoxytritylthio)oxy]methyl}benzoate, 2-{[methyl(tritylthio)amino]methyl}benzoate, 2-{{[(4-methoxytrityl)thio]methylamino}-methyl}benzoate, 2-(allyloxy)phenylacetate, 2-(prenyloxymethyl)benzoate, 6-(levulinyloxymethyl)-3-methoxy-2-nitrobenzoate, 6-(levulinyloxymethyl)-3-methoxy-4-nitrobenzoate, 4-benzyloxybutyrate, 4-trialkylsilyloxybutyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-(methylthiomethoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, and 2-chlorobenzoate. In the case of sulfonates, sulfenates and sulfinates the protecting group for the OH can be selected from sulfate, allylsulfonate, methanesulfonate, benzylsulfonate, tosylate, 2-[(4-nitrophenyl)ethyl]sulfonate, 2-trifluoromethylbenzenesulfonate, 4-monomethoxytritylsulfenate, alkyl 2,4-dinitrophenylsulfenate, 2,2,5,5-tetramethylpyrrolidin-3-one-1-sulfinate, borate, and dimethylphosphinothiolyl. In the case of carbonates the protecting group for the OH can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl]ethyl carbonate, 2-(phenylsulfonyl)ethyl carbonate, 2-(triphenylphosphonio)ethyl carbonate, cis-[4-[[(methoxytrityl)sulfenyl]oxy]tetrahydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, alkyl 2-(3,4-methylenedioxy-6-nitrophenyl)propyl carbonate, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, and S-benzyl thiocarbonate. And in the case of carbamates the protecting group for the OH can be selected from dimethylthiocarbamate, N-phenylcarbamate, N-methyl-N-(o-nitrophenyl)carbamate. The mention of these groups should be not interpreted as a limitation of the scope of the invention, since they have been mentioned as a mere illustration of protecting groups for OH, but further groups having said function may be known by the skill person in the art, and they are to be understood to be also encompassed by the present invention.

The term "pharmaceutically acceptable salts, derivatives, prodrugs" refers to any pharmaceutically acceptable salt, ester, solvate, hydrate or any other compound which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in crystalline form either as free compounds or as solvates (e.g. hydrates) and it is intended that both forms are within the scope of the present invention. Methods of solvation are generally known within the art.

Any compound that is a prodrug of a compound of formula I is within the scope and spirit of the invention. The term "prodrug" is used in its broadest sense and encompasses those derivatives that are converted in vivo to the compounds of the invention. Such derivatives would readily occur to those skilled in the art, and include, for example, compounds where a free hydroxy group is converted into an ester derivative.

Any compound referred to herein is intended to represent such specific compound as well as certain variations or forms. In particular, compounds referred to herein may have asymmetric centres and therefore exist in different enantiomeric forms. All optical isomers and stereoisomers of the compounds referred to herein, and mixtures thereof, are considered within the scope of the present invention. Thus any given compound referred to herein is intended to represent any one of a racemate, one or more enantiomeric forms, one or more diastereomeric forms, one or more atropisomeric forms, and mixtures thereof. Particularly, the compounds of the present invention represented by the above described formula I may include enantiomers depending on their asymmetry or diastereoisomers. Stereoisomerism about the double bond is also possible, therefore in some cases the molecule could exist as (E)-isomer or (Z)-isomer. If the molecule contains several double bonds, each double bond will have its own stereoisomerism, that could be the same or different than the stereoisomerism of the other double bonds of the molecule. The single isomers and mixtures of isomers fall within the scope of the present invention.

Furthermore, compounds referred to herein may exist as geometric isomers (i.e., cis and trans isomers), as tautomers, or as atropisomers. Specifically, the term tautomer refers to one of two or more structural isomers of a compound, that exist in equilibrium and are readily converted from one isomeric form to another. Common tautomeric pairs are amine-imine, amide-imide, keto-enol, lactam-lactim, etc. Additionally, any compound referred to herein is intended to represent hydrates, solvates, and polymorphs, and mixtures thereof when such forms exist in the medium. In addition, compounds referred to herein may exist in isotopically-labelled forms. All geometric isomers, tautomers, atropisomers, hydrates, solvates, polymorphs, and isotopically labelled forms of the compounds referred to herein, and mixtures thereof, are considered within the scope of the present invention.

To provide a more concise description, some of the quantitative expressions given herein are not qualified with the term "about". It is understood that, whether the term "about"

is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

In compounds of general formula I, particularly preferred $R_1$ is hydrogen, $OR_a$ and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, propyl, isopropyl and butyl, including tert-butyl. Hydrogen, OH and methoxy are the most preferred $R_1$ groups.

Particularly preferred $R_2$ and $R_3$ are hydrogen and substituted or unsubstituted $C_1$-$C_{12}$ alkyl. More preferred $R_2$ and $R_3$ are hydrogen and substituted or unsubstituted $C_1$-$C_6$ alkyl, and even more preferred are hydrogen.

Particularly preferred $R_{41}$, $R_{42}$, $R_{43}$, $R_{44}$, $R_{45}$, $R_{46}$, $R_{47}$ and $R_{48}$ are hydrogen and substituted or unsubstituted $C_1$-$C_{12}$ alkyl. More preferred $R_{41}$, $R_{42}$, $R_{43}$, $R_{44}$, $R_{45}$, $R_{46}$, $R_{47}$ and $R_{48}$ are hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl and substituted or unsubstituted butyl, including substituted or unsubstituted tert-butyl, substituted or unsubstituted isobutyl and substituted or unsubstituted sec-butyl. Preferred substituents of said groups are OR', =O, SR', SOR', $SO_2R'$, $NO_2$, NHR', N(R')$_2$, =N—R', NHCOR', N(COR')$_2$, $NHSO_2R'$, NR'C(=NR')NR'R', CN, halogen, COR', COOR', OCOR', OCONHR', OCON(R')$_2$, protected OH, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, NHC(=NH)$NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen, methyl, isopropyl, tert-butyl and benzyl are the most preferred $R_{41}$, $R_{42}$, $R_{43}$, $R_{44}$, $R_{45}$, $R_{46}$, $R_{47}$ and $R_{48}$ groups. Specifically, particularly preferred $R_{42}$, $R_{44}$, $R_{45}$, $R_{46}$, and $R_{47}$ are hydrogen. *Particularly preferred $R_{41}$ and $R_{43}$ are methyl.* And particularly preferred $R_{48}$ is isopropyl, tert-butyl, or benzyl.

Particularly preferred $R_5$ and $R_6$ are hydrogen and substituted or unsubstituted $C_1$-$C_{12}$ alkyl. More preferred $R_5$ and $R_6$ are hydrogen and substituted or unsubstituted $C_1$-$C_6$ alkyl; and even more preferred are hydrogen, methyl, ethyl, propyl, isopropyl and butyl, including tert-butyl. Hydrogen is the most preferred.

In another embodiment of the invention, it is also preferred that $R_5$ and $R_{48}$ together with the corresponding N atom and C atom to which they are attached form a substituted or unsubstituted heterocyclic group. Preferred heterocyclic group is pyrrolidinyl, including 1-, 2- and 3-pyrrolidinyl.

Particularly preferred $R_7$ is hydrogen, substituted or unsubstituted $C_1$-$C_{12}$ alkyl and substituted or unsubstituted $C_2$-$C_{12}$ alkenyl, and more preferably is hydrogen, substituted $C_1$-$C_{12}$ alkyl and substituted $C_2$-$C_{12}$ alkenyl. The preferred substituted alkyl and substituted alkenyl may present not only one but two or more substituients. More preferred alkyl groups are those having from 6 to about 10 carbon atoms; and even more preferably 7, 8 or 9 carbon atoms. Heptyl, octyl and nonyl are the most preferred alkyl groups. On the other hand, more preferred alkenyl groups are those having from 6 to about 10 carbon atoms; and even more preferably 7, 8 or 9 carbon atoms. Octa-1,6-dienyl, octa-1,5-dienyl, octa-1,4-dienyl, octa-1,3-dienyl, nona-1,7-dienyl, nona-1,6-dienyl, nona-1,5-dienyl, nona-1,4-dienyl, nona-1,3-dienyl, hepta-1,5-dienyl, hepta-1,4-dienyl, hepta-1,3-dienyl are the most preferred alkenyl groups. Preferred substituents for said alkyl and alkenyl groups are OR', =O, SR', SOR', $SO_2R'$, $NO_2$, NHR', N(R')$_2$, =N—R', NHCOR', N(COR')$_2$, $NHSO_2R'$, NR'C(=NR') NR'R', CN, halogen, COR', COOR', OCOR', OCONHR', OCON(R')$_2$, protected OH, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkyl and alkenyl groups are halogen, OR', =O, OCOR", OCONHR', OCON(R')$_2$, and protected OH, wherein each of the R' groups is preferably selected from hydrogen, substituted or unsubstituted $C_1$-$C_{12}$ alkyl or substituted or unsubstituted $C_2$-$C_{12}$ alkenyl, substituted or unsubstituted $C_2$-$C_{12}$ alkynyl, and substituted or unsubstituted aryl. Even more preferred substituents for these alkyl and alkenyl groups are halogen, OR', =O, OCONHR', OCON(R')$_2$, and protected OH wherein the protecting group for the OH is preferably selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3[2-(triphenylmethoxy)ethoxy]disiloxane-1-yl, and fluorous silyl, and wherein each of the R' groups is more preferably selected from hydrogen, unsubstituted $C_1$-$C_6$ alkyl, and substituted or unsubstituted aryl. Cl, OH, =O, $OCONH_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl) silyl, (2-hydroxystyryl)dimethylsilyl, (2-hydroxystyryl) diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, are the most preferred substituents for these alkyl and alkenyl groups.

Particularly preferred is the presence of one or more additional bonds in the places indicated with a dotted line. More preferred is the presence of an additional bond in all the places indicated with a dotted line. In addition, the stereochemistry of each double bond may exist as (E) or (Z). The single isomers and mixtures of the isomers fall within the scope of the present invention.

More particularly, the invention provides compounds of general formula II or pharmaceutically acceptable salts, derivatives, tautomers, prodrugs or stereoisomers thereof

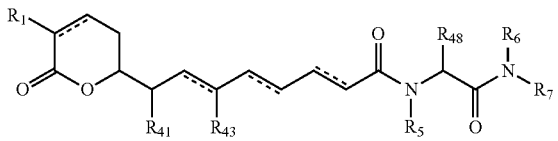

(II)

wherein
$R_1$ is selected from hydrogen, $OR_a$, $OCOR_a$, $OCOOR_a$, $NR_aR_b$, $NR_aCOR_b$, and $NR_aC(NR_a)NR_aR_b$;
each $R_{41}$, $R_{43}$ and $R_{48}$ are independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl;
each $R_5$, $R_6$, and $R_7$ are independently selected from hydrogen, $COR_a$, $COOR_a$, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, or $R_5$ and $R_{48}$ together with the corresponding N atom and C atom to which they are attached may form a substituted or unsubstituted heterocyclic group;
each $R_a$ and $R_b$ are independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl and substituted or unsubstituted heterocyclic group; and
each dotted line represent an optional additional bond.

In compounds of general formula II, particularly preferred $R_1$ is hydrogen, $OR_a$ and $OCOR_a$, wherein $R_a$ is selected from hydrogen and substituted or unsubstituted $C_1$-$C_{12}$ alkyl. Particularly preferred $R_a$ is hydrogen and substituted or unsubstituted $C_1$-$C_6$ alkyl; and even more preferred is hydrogen, methyl, ethyl, propyl, isopropyl and butyl, including tert-butyl. Hydrogen, OH and methoxy are the most preferred $R_1$ groups.

Particularly preferred $R_{41}$, $R_{43}$ and $R_{48}$ are hydrogen and substituted or unsubstituted $C_1$-$C_{12}$ alkyl. More preferred $R_{41}$, $R_{43}$ and $R_{48}$ are hydrogen and substituted or unsubstituted $C_1$-$C_6$ alkyl, and even more preferred is hydrogen, substituted or unsubstituted methyl, substituted or unsubstituted ethyl, substituted or unsubstituted propyl, substituted or unsubstituted isopropyl and substituted or unsubstituted butyl, including substituted or unsubstituted tert-butyl, substituted or unsubstituted isobutyl and substituted or unsubstituted sec-butyl. Preferred substituents of said groups are OR', =O, SR', SOR', $SO_2R'$, $NO_2$, NHR', $N(R')_2$, =N—R', NHCOR', $N(COR')_2$, $NHSO_2R'$, NR'C(=NR')NR'R', CN, halogen, COR', COOR', OCOR', OCONHR', $OCON(R')_2$, protected OH, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. Even more preferred substituents of the above mentioned groups are OH, $SCH_3$, SH, $NH_2$, NHC(=NH)$NH_2$, $CONH_2$, COOH, phenyl, p-, m- or o-hydroxyphenyl, indolyl, including 1-, 2-, and 3-indolyl, and imidazolyl, including 4- and 5-imidazolyl. Hydrogen, methyl, isopropyl, tert-butyl and benzyl are the most preferred $R_{41}$, $R_{43}$ and $R_{48}$ groups. Specifically, particularly preferred $R_{41}$ and $R_{43}$ are methyl, and particularly preferred $R_{48}$ is isopropyl, tert-butyl, or benzyl.

Particularly preferred $R_5$ and $R_6$ are hydrogen and substituted or unsubstituted $C_1$-$C_{12}$ alkyl. More preferred $R_5$ and $R_6$ are hydrogen and substituted or unsubstituted $C_1$-$C_6$ alkyl; and even more preferred are hydrogen, methyl, ethyl, propyl, isopropyl and butyl, including tert-butyl. Hydrogen is the most preferred.

In another embodiment of the invention, it is also preferred that $R_5$ and $R_{48}$ together with the corresponding N atom and C atom to which they are attached form a substituted or unsubstituted heterocyclic group. Preferred heterocyclic group is pyrrolidinyl, including 1-, 2- and 3-pyrrolidinyl.

Particularly preferred $R_7$ is hydrogen, substituted or unsubstituted $C_1$-$C_{12}$ alkyl and substituted or unsubstituted $C_2$-$C_{12}$ alkenyl, and more preferably is hydrogen, substituted $C_1$-$C_{12}$ alkyl and substituted $C_2$-$C_{12}$ alkenyl. More preferred alkyl groups are those having from 6 to about 10 carbon atoms; and even more preferably 7, 8 or 9 carbon atoms. Heptyl, octyl and nonyl are the most preferred alkyl groups. On the other hand, more preferred alkenyl groups are those having from 6 to about 10 carbon atoms; and even more preferably 7, 8 or 9 carbon atoms. Octa-1,6-dienyl, octa-1,5-dienyl, octa-1,4-dienyl, octa-1,3-dienyl, nona-1,7-dienyl, nona-1,6-dienyl, nona-1,5-dienyl, nona-1,4-dienyl, nona-1,3-dienyl, hepta-1,5-dienyl, hepta-1,4-dienyl, hepta-1,3-dienyl are the most preferred alkenyl groups. Preferred substituents for said alkyl and alkenyl groups are OR', =O, SR', SOR', $SO_2R'$, $NO_2$, NHR', $N(R')_2$, =N—R', NHCOR', $N(COR')_2$, $NHSO_2R'$, NR'C(=NR')NR'R', CN, halogen, COR', COOR', OCOR', OCONHR', $OCON(R')_2$, protected OH, substituted or unsubstituted aryl, and substituted or unsubstituted heterocyclic group, wherein each of the R' groups is independently selected from the group consisting of hydrogen, OH, $NO_2$, $NH_2$, SH, CN, halogen, COH, COalkyl, COOH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group. Where such groups are themselves substituted, the substituents may be chosen from the foregoing list. More preferred substituents for the above mentioned alkyl and alkenyl groups are halogen, OR', =O, OCOR', OCONHR', $OCON(R')_2$, and protected OH, wherein each of the R' groups is preferably selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted aryl. Even more preferred substituents for these alkyl and alkenyl groups are halogen, OR', =O, OCONHR', $OCON(R')_2$, and protected OH wherein the protecting group for the OH is preferably selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, and wherein each of the R' groups is more preferably selected from hydrogen, unsubstituted $C_1$-$C_6$ alkyl, and substituted or unsubstituted aryl. Cl, OH, =O, $OCONH_2$, OCONHPhenyl, and protected OH wherein the protecting group for the OH is preferably selected from trimethylsilyl, triethylsilyl, triisopropylsilyl, dimethylisopropylsilyl, diethylisopropylsilyl, dimethylhexylsylil, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl) silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl, are the most preferred substituents for these alkyl and alkenyl groups.

Particularly preferred is the presence of one or more additional bonds in the places indicated with a dotted line. More preferred is the presence of an additional bond in all the places indicated with a dotted line. In addition, the stereochemistry of each double bond may exist as (E) or (Z). The single isomers and mixtures of the isomers fall within the scope of the present invention.

Particularly preferred compounds of the invention are the following:

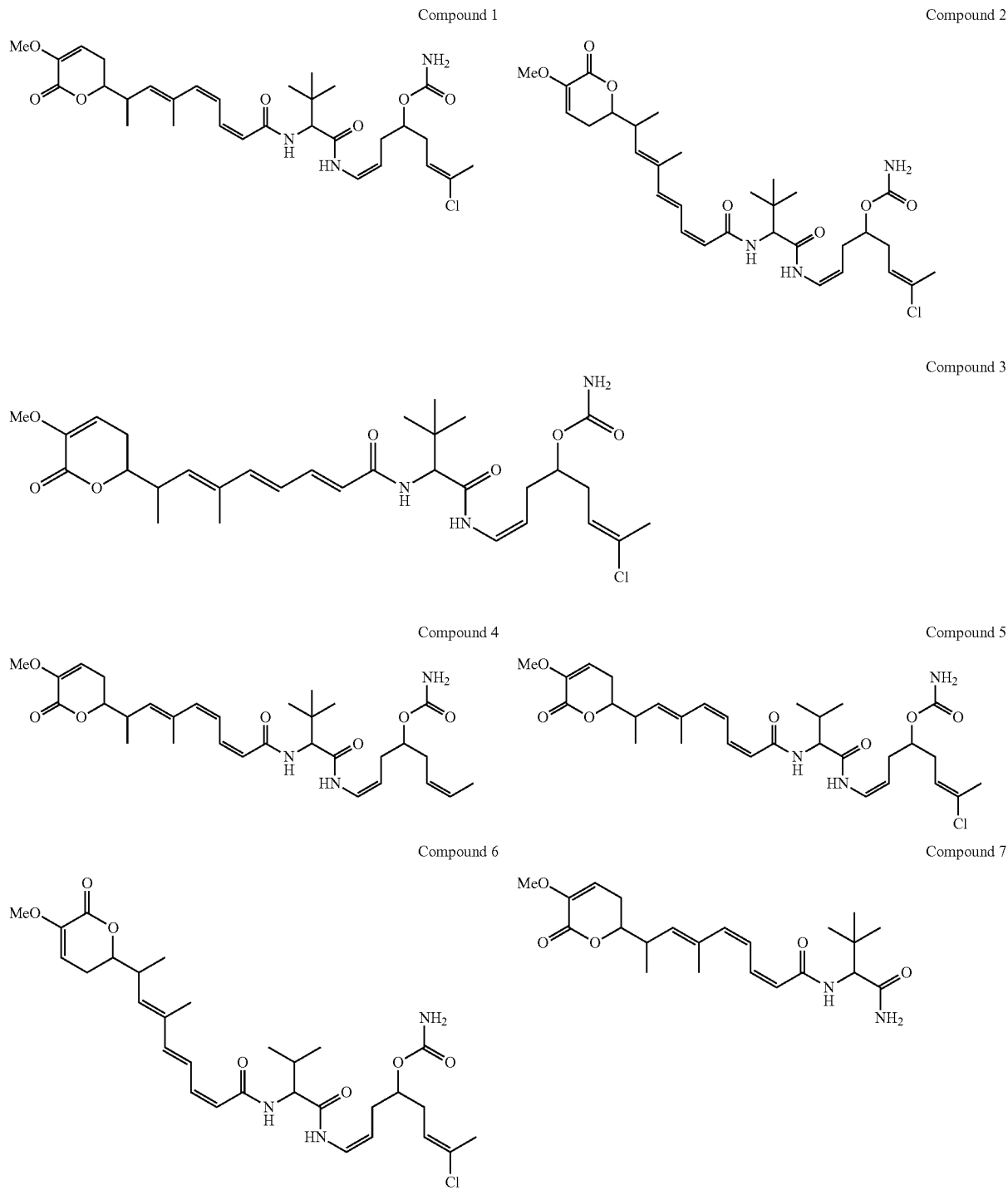

-continued

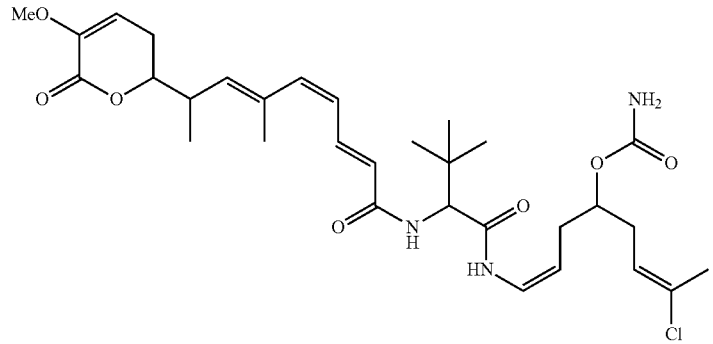

Compound 8

Compounds 1-8 were isolated from a porifera, of the family Raspailiidae, genus *Lithoplocamia*, species *lithistoides*.

A sample of *Lithoplocamia lithistoides* was deposited in the "Instituto de Ciencias del Mar y Limnología" of the Universidad Nacional Autónoma de México in Mazatlan, in Mexico, with the reference code LEB-ICML-UNAM-11-2004. This sponge was collected by hand using SCUBA diving in Madagascar (S 17° 06.071'/E 49° 51.385') at a depth ranging between 6 and 20 m, and its description is the following:

Family Raspailiidae: Raspailiidae Hentschel, 1923 are sponges with encrusting, massive, lobate, fan-shaped or branching growth forms, usually with a very hispid surface. A specialised ectosomal skeleton is typically present, consisting of brushes of small thin styles (Hooper & Wiedenmayer 1994: FIG. 17) or oxeas (Hooper & Wiedenmayer 1994: FIG. 5), surrounding individual long thick styles or oxeas. The choanosomal skeleton varies from a compressed axial skeleton, to plumo-reticulate or exclusively reticulate structures. Spongin fibres usually completely enclose coring spicules (choanosomal styles, oxeas or both). A special category of spined styles (Hooper & Wiedenmayer 1994: FIG. 22), or modifications to styles (e.g. FIGS. 22-25, 28), echinate fibres, protrude at right angles from fibres. Microscleres are usually absent, although single raphides (Hooper & Wiedenmayer 1994: FIG. 109) or bundles (trichodragmata; Hooper & Wiedenmayer 1994: FIG. 110) may occur in some genera. Raspailiids are widely distributed, ranging from shallow waters to at least 2460 m in depth (Hartman 1982).

Genus *Lithoplocamia*, species *lithistoides* are encrusting and massive growth forms, choanosomal skeleton is a dense isodictyal or irregularly subisodictyal reticulation of acanthostrongyles, in 1 or 2 size categories, without axial condensation, without echinating acanthostyles, with extra-axial radial tracts of smooth styles, and typically without a specialized raspailiid ectosomal skeleton (although when present ectosomal spicules are long slender oxeas); microscleres absent.

Samples of *Lithoplocamia lithistoides* were also collected in Kenya (S 04° 40' 5.5"/E 39° 26' 4.3", and S 03° 38' 36.5"/E 39° 53' 53.8") and Tanzania (S 08° 55' 31.7"/E 39° 34' 53.5", and S 05° 24.200'/E 39° 47.730') at a depth ranging between 30 and 40 m.

Additionally, the compounds of the invention can be obtained by synthesis. For example, compound 1 can be made by joining different fragments as indicated in the Scheme 1.

Scheme 1

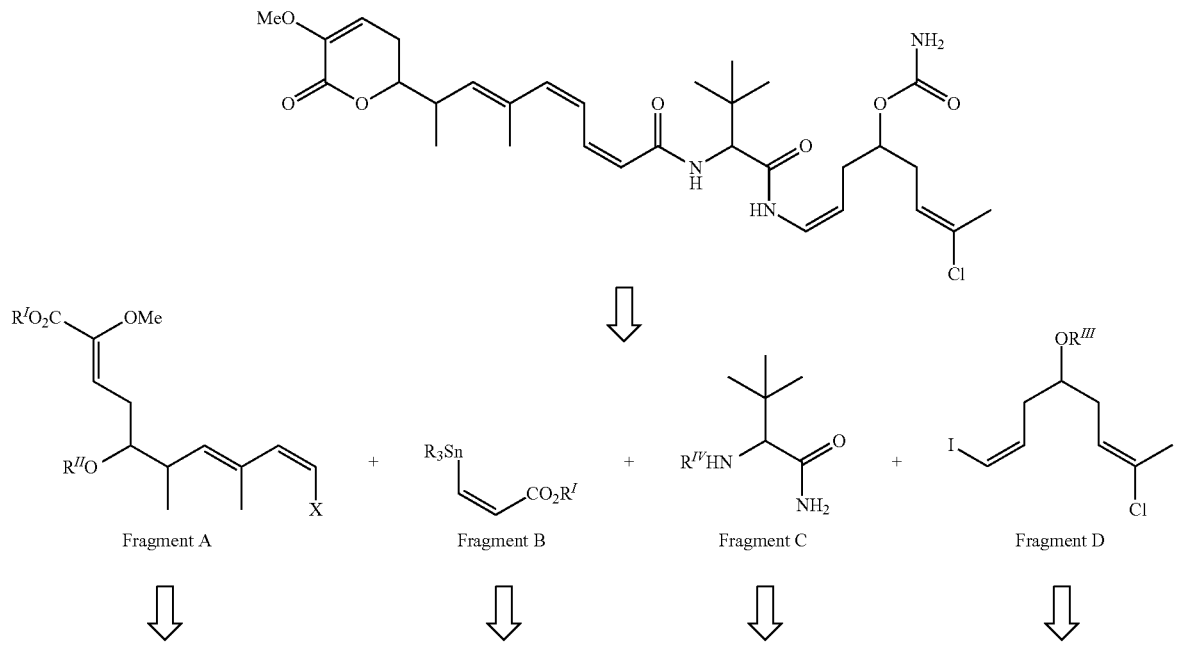

-continued

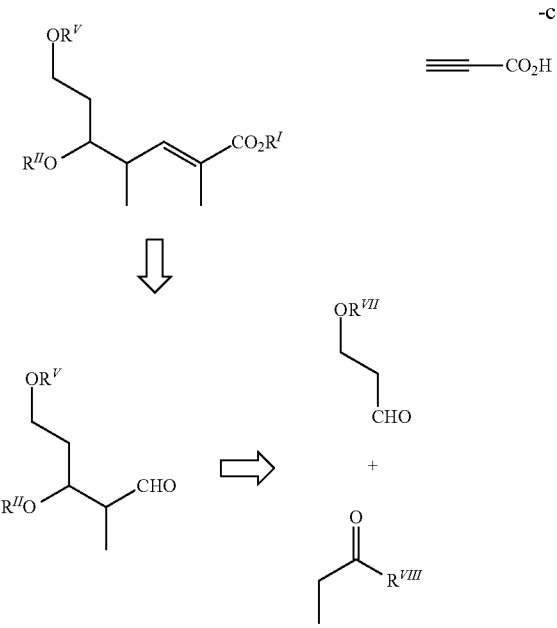
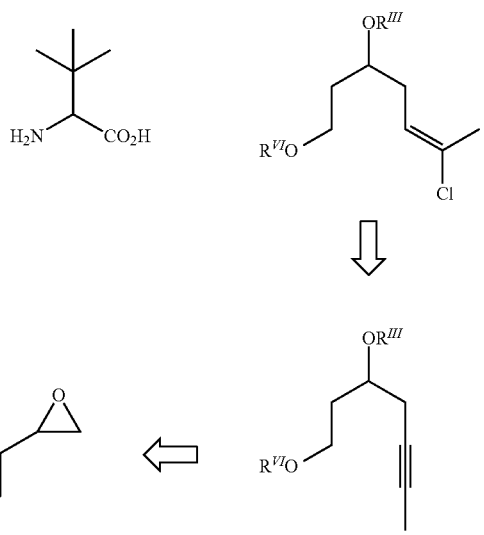

where R, $R^I$, $R^{II}$, $R^{III}$, $R^{IV}$, $R^V$, $R^{VI}$, $R^{VII}$ and $R^{VIII}$ are the desired group or an appropriate protecting group as needed.

This process can comprise the following key steps:

a) Amidation of the iodoalkenyl derivative (Fragment D) with Fragment C following standard literature procedures (Kozawa Y et al. Tetrahedron Lett. 2002, 43, 111) to afford the corresponding enamide (fragment CD).

b) Stille coupling reaction between Fragment A and Fragment B following known procedures in organic synthesis (Scott W J et al. J. Am. Chem. Soc. 1984, 106, 4630; Labadie J W et al. J. Org. Chem. 1983, 48, 4634-4642; Farina V et al. Organic Reactions 1998, Wiley) to obtain the linear polyene (fragment AB).

c) Fragments AB and CD can be coupled following standard procedures (Bodanszky M and Bodanszky A, The Practice of Peptide Synthesis, Springer-Verlag, 1993) to obtain the carbon skeleton of compound 1.

d) Deprotection of the alcohol $OR^{II}$ followed by lactonization can be achieved according to known procedures in organic synthesis (Greene and Wuts, Protective Groups in Organic Synthesis, $3^{rd}$ ed., Wiley-Interscience; Burke and Danheiser, Handbook of Reagents for Organic Synthesis Oxidizing and Reducing Agents, Wiley; Pla D et al. J. Org. Chem. 2005, 70, 8231).

e) Finally, deprotection of alcohol $OR^{III}$ followed by formation of the carbamate can be achieved by means of standard literature procedures (Love B et al. Organic Syntheses, Coll. Vol. 5, p. 162; Vol. 48, p. 32; Müller E et al. Methoden der Organischen Chemie (Houben-Weyl), $4^{th}$ ed., Vol. 8, G. Thieme, Stuttgart, 1952, p. 137) to obtain compound 1.

The sequence of steps can be interchanged to obtain the final compound. For example, fragment BC can be prepared at first stage and then the sequential coupling with fragments A and D afford the carbon skeleton of compound 1. Likewise, compound 1 can be prepared by the sequential coupling of fragments A, B, C, and D in any order. Another option is to perform the formation of the lactone moiety on fragment A previous to its coupling with any other fragment.

Analogues of compound 1 can be synthesized by an equivalent process as those described for compound 1, by choosing the appropriate substituents of the intermediate compounds in each case.

When necessary, appropriate protecting groups can be used on the substituents to ensure that reactive groups are not affected. The synthesis can be designed to employ precursor substituents which can be converted at the appropriate stage to a desired substituent. Saturation or unsaturation in the ring-structure can be introduced or removed as part of the synthesis. Starting materials and reagents can be modified as desired to ensure synthesis of the intended compound. In addition, analogues can also be synthesized from compound 1 by usual procedures in synthetic organic chemistry which are known by a person skilled in the art.

The synthetic routes above mentioned can be modified as desired to give stereospecific compounds as well as mixtures of stereoisomers. It is possible to synthesize specific stereoisomers or specific mixtures by various methods including the use of stereospecific reagents or by introducing chiral centers into the compounds during the synthesis. It is possible to introduce one or more stereocenters during synthesis and also invert existing stereocenters. In addition, it is possible to separate stereoisomers once the compound has been synthesized by standard resolution techniques known to the skilled reader.

An important feature of the above described compounds of formula I and II is their bioactivity and in particular their cytotoxic and antimitotic activity.

With this invention we provide novel pharmaceutical compositions of compounds of general formula I and II that possess cytotoxic and antimitotic activities and their use as antitumor agents. Thus the present invention further provides pharmaceutical compositions comprising a compound of this invention, a pharmaceutically acceptable salt, derivative, tautomer, prodrug or stereoisomer thereof with a pharmaceutically acceptable carrier.

Examples of pharmaceutical compositions include any solid (tablets, pills, capsules, granules, etc.) or liquid (solutions, suspensions or emulsions) compositions for oral, topical or parenteral administration.

Administration of the compounds or compositions of the present invention may be by any suitable method, such as intravenous infusion, oral preparations, and intraperitoneal and intravenous administration.

We prefer that infusion times of up to 24 hours are used, more preferably 1-12 hours, with 1-6 hours most preferred.

Short infusion times which allow treatment to be carried out without an overnight stay in hospital are especially desirable. However, infusion may be 12 to 24 hours or even longer if required. Infusion may be carried out at suitable intervals of say 1 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds and compositions of this invention may be used with other drugs to provide a combination therapy. The other drugs may form part of the same composition, or be provided as a separate composition for administration at the same time or at different time.

Antitumoral activities of these compounds include, but are not limited, lung cancer, colon cancer, breast cancer and cervix cancer.

EXAMPLES

Example 1

Description of the Marine Organism and Collection Side

*Lithoplocamia lithistoides* was collected by hand using SCUBA diving in Madagascar (S 17° 06.071'/E 49° 51.385') at a depth ranging between 6 and 20 m. The animal material was identified by José Luis Carballo (Universidad Autónoma de Méjico). A sample of the specimen was deposited in the "Instituto de Ciencias del Mar y Limnología" of the Universidad Nacional Autónoma de México in Mazatlan, in Mexico, with the reference code LEB-ICML-UNAM-11-2004.

Example 2

Isolation of Compound 1

The frozen specimen of Example 1 (61 g) was diced and extracted with $H_2O$ (3×200 mL) and then with a mixture of MeOH:Dichloromethane (1:1, 3×200 mL) at room temperature. The combined organic extracts were concentrated to yield a crude of 1.11 g. This material was subjected to VLC on Lichroprep RP-18 with a stepped gradient from $H_2O$ to MeOH.

Compound 1 (1.6 mg) was isolated from fractions eluting with MeOH by semipreparative reversed phase HPLC (SymmetryPrep C18 7 µm, 7.8×150 mm, gradient $H_2O$:MeCN from 35 to 100% MeCN in 30 min, UV detection, flow 2.5 mL/min, rt 14.4 min.).

Compound 1: amorphous white solid. (+)HRESIMS m/z 606.2940 $[M+H]^+$ (Calcd. for $C_{31}H_{45}{}^{35}ClN_3O_7$ 606.2946); $^1H$ (500 MHz) and $^{13}C$ NMR (125 MHz) see Table 1.

TABLE 1

| | $^1H$ and $^{13}C$ NMR data of Compound 1 ($CDCl_3$) | |
|---|---|---|
| N° | $^1H$ (Multiplicity, J) | $^{13}C$ |
| 1 | — | 161.6 |
| 2 | — | 145.2 |
| 3 | 5.63 (dd, 6.5, 2.6) | 108.2 |
| 4 | 2.45 (ddd, 17.3, 11.5, 2.6) | 26.1 |
|   | 2.37 (ddd, 17.3, 6.5, 4.1) | |
| 5 | 4.24 (ddd, 11.5, 7.1, 4.1) | 81.9 |
| 6 | 2.85 (ddq, 9.8, 7.1, 6.7) | 37.1 |
| 7 | 5.29 (d, 9.8) | 134.1 |
| 8 | — | 133.7 |
| 9 | 6.17 (d, 11.6) | 140.2 |
| 10 | 7.30 (dd, 11.6, 11.6) | 124.6 |
| 11 | 6.91 (dd, 11.6, 11.6) | 137.6 |
| 12 | 5.70 (d, 11.6) | 120.7 |
| 13 | — | 166.3 |
| 14 | 6.51 (d, 9.5) | — |
| 15 | 4.41 (d, 9.5) | 60.8 |
| 16 | — | 168.2 |
| 17 | 8.78 (d, 10.8) | — |
| 18 | 6.84 (br dd, 10.8, 9.7) | 124.5 |
| 19 | 4.80 (m) | 105.0 |
| 20 | 2.46 (m) | 30.7 |
|   | 2.09 (ddd, 14.1, 8.4, 8.1) | |
| 21 | 4.41 (m) | 74.9 |
| 22 | 2.33 (m), 2.H | 33.0 |
| 23 | 5.61 (br t, 6.8) | 122.4 |
| 24 | — | 132.0 |
| 25 | 2.06 (s), 3H | 21.0 |
| 26 | 3.66 (s), 3H | 55.4 |
| 27 | 1.15 (d, 6.7), 3H | 16.3 |
| 28 | 1.82 (s), 3H | 17.1 |
| 29 | — | 34.7 |
| 30 | 1.04 (s), 3H | 26.7 |
| 31 | 1.04 (s), 3H | 26.7 |
| 32 | 1.04 (s), 3H | 26.7 |
| 33 | — | 157.2 |

TABLE 1-continued

¹H and ¹³C NMR data of Compound 1 (CDCl₃)

| N° | ¹H (Multiplicity, J) | ¹³C |
|---|---|---|

Compound 1

Example 3

Isolation of Compounds 2, 3, 4, 5, 6 and 7

A second group of samples of *Lithoplocamia lithistoides* (7.66 kg) was triturated and exhaustively extracted with a mixture of MeOH:Dichloromethane (1:1, 14 L, 2×5 L, 4 L). The solvent was removed in vacuo and the remaining aqueous solution was extracted with EtOAc (12 L, 3×8 L). The organic layer was evaporated to yield a crude of 21.71 g.

This material was subjected to RP-18 column chromatography with a stepped gradient from H₂O:MeOH (4:6) to MeOH. Fractions eluted with H₂O:MeOH (2:8, 430 mg) were pooled and subjected to preparative HPLC (Atlantis dC₁₈, OBD, 5 μm, 19×150 mm, isocratic H₂O:MeOH (39:61), flow: 20 mL/min, UV detection) to yield pure compounds 1 (160.8 mg), 2 (13.2 mg), and 7 (1.8 mg), and mixtures of 3 and 4 (11.4 mg) and 5 and 6 (10.0 mg). Pure compounds 3 (5.1 mg) and 4 (2.6 mg) were obtained after a final purification of the mixture by semipreparative HPLC (X-Terra Prep RP-18, 10 μm, 10×150 mm, gradient H₂O:MeOH for 50 to 70% MeOH in 70 min, flow: 2.5 mL/min, UV detection). Compounds 5 (3.6 mg) and 6 (1.0 mg) were separated in a similar manner by semipreparative HPLC (X-Terra Prep RP-18, 10 μm, 10×150 mm, isocratic H₂O:MeOH (45:55), flow: 2.5 mL/min, UV detection).

Compound 2: amorphous white solid. MS (ES) m/z 606.3 [M+H]⁺, 628.3 [M+Na]⁺; ¹H (500 MHz) and ¹³C NMR (125 MHz) see Table 2.

Compound 3: amorphous white solid. (+)HRESIMS m/z 628.2774 [M+Na]⁺ (Calcd. for $C_{31}H_{44}{}^{35}ClN_3O_7Na$ 628.2760); ¹H (500 MHz) and ¹³C NMR (125 MHz) see Table 3.

Compound 4: amorphous white solid. (+)HRESIMS m/z 594.3152 [M+Na]⁺ (Calcd. for $C_{31}H_{45}N_3O_7Na$ 594.3150); ¹H (500 MHz) and ¹³C NMR (125 MHz) see Table 4.

Compound 5: amorphous white solid. MS (ES) m/z 592.3 [M+H]⁺, 614.3 [M+Na]⁺; ¹H (500 MHz) and ¹³C NMR (125 MHz) see Table 5.

Compound 6: amorphous white solid. MS (ES) m/z 592.3 [M+H]⁺, 614.3 [M+Na]⁺; ¹H (500 MHz) and ¹³C NMR (125 MHz) see Table 6.

Compound 7: amorphous white solid. (+)HRESIMS m/z 427.2207 [M+Na]⁺ (Calcd. for $C_{22}H_{32}N_2O_5Na$ 427.2203); ¹H (500 MHz) and ¹³C NMR (125 MHz) see Table 7.

TABLE 2

¹H and ¹³C NMR data of Compound 2 (CDCl₃)

| N° | ¹H (Multiplicity, J) | ¹³C |
|---|---|---|
| 1 | — | 161.5 |
| 2 | — | 145.2 |
| 3 | 5.61 (dd, 6.4, 3.1) | 108.1 |
| 4 | 2.41 (ddd, 17.1, 11.3, 3.0) 2.34 m | 26.6 |
| 5 | 4.18 (ddd, 11.3, 7.8, 4.3) | 81.6 |
| 6 | 2.88 (ddq, 10.0, 7.8, 6.7) | 37.4 |
| 7 | 5.46 (br d, 10.0) | 136.5 |
| 8 | — | 135.6 |
| 9 | 6.41 (d, 15.5) | 145.0 |
| 10 | 7.60 (dd, 15.5, 11.4) | 124.2 |
| 11 | 6.49 (dd, 11.4, 11.3) | 142.5 |
| 12 | 5.63 (d, 11.3) | 119.0 |
| 13 | — | 166.5 |
| 14 | 6.39 (d, 9.4) | — |
| 15 | 4.44 (d, 9.4) | 60.7 |
| 16 | — | 168.3 |
| 17 | 8.50 (br d, 10.8) | — |
| 18 | 6.83 (ddd, 10.8, 8.9, 1.2) | 124.4 |
| 19 | 4.80 (m) | 105.5 |
| 20 | 2.43 (m) 2.12 (m) | 30.6 |
| 21 | 4.50 (m) | 74.9 |
| 22 | 2.36 (m), 2H | 33.2 |

TABLE 2-continued
$^1$H and $^{13}$C NMR data of Compound 2 (CDCl$_3$)
| N° | $^1$H (Multiplicity, J) | $^{13}$C |
|---|---|---|
| 23 | 5.61 (br t, 6.5) | 122.2 |
| 24 | — | 132.1 |
| 25 | 2.07 (d, 1.0), 3H | 21.0 |
| 26 | 3.65 (s), 3H | 55.4 |
| 27 | 1.16 (d, 6.7), 3H | 16.5 |
| 28 | 1.86 (d, 1.0), 3H | 13.1 |
| 29 | — | 34.6 |
| 30 | 1.05 (s), 3H | 26.6 |
| 31 | 1.05 (s), 3H | 26.6 |
| 32 | 1.05 (s), 3H | 26.6 |
| 33 | — | 157.0 |
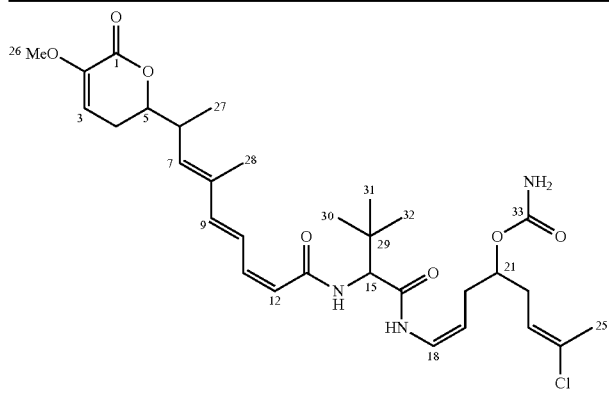
Compound 2
TABLE 3
$^1$H and $^{13}$C NMR data of Compound 3 (CDCl$_3$)
| N° | $^1$H (Multiplicity, J) | $^{13}$C |
|---|---|---|
| 1 | — | 161.5 |
| 2 | — | 145.3 |
| 3 | 5.61 (dd, 6.3, 3.0) | 108.1 |
| 4 | 2.39 (m) | 26.3 |
|   | 2.37 (m) |  |
| 5 | 4.21 (ddd, 10.9, 7.6, 4.7) | 81.7 |
| 6 | 2.90 (ddq, 10.0, 7.6, 6.6) | 37.4 |
| 7 | 5.46 (br d, 10.0) | 136.4 |
| 8 | — | 135.1 |
| 9 | 6.51 (d, 15.3) | 144.1 |
| 10 | 6.27 (dd, 15.3, 11.1) | 125.2 |
| 11 | 7.25 (dd, 14.8, 11.1) | 141.9 |
| 12 | 5.96 (d, 14.8) | 122.9 |
| 13 | — | 166.0 |
| 14 | 6.39 (d, 9.3) | — |
| 15 | 4.43 (d, 9.3) | 60.8 |
| 16 | — | 168.3 |
| 17 | 8.82 (d, 10.7) | — |
| 18 | 6.83 (br dd, 10.7, 9.6) | 124.4 |
| 19 | 4.81 (m) | 105.4 |
| 20 | 2.47 (m) | 30.8 |
|   | 2.10 (m) |  |
| 21 | 4.43 (m) | 75.0 |
| 22 | 2.34 (m), 2H | 33.0 |
| 23 | 5.62 (br t, 6.5) | 122.4 |
| 24 | — | 132.0 |
| 25 | 2.07 (s), 3H | 21.0 |
| 26 | 3.65 (s), 3H | 55.4 |
| 27 | 1.15 (d, 6.6), 3H | 16.6 |
| 28 | 1.83 (d, 1.0), 3H | 12.9 |
| 29 | — | 35.1 |
| 30 | 1.03 (s), 3H | 26.6 |
| 31 | 1.03 (s), 3H | 26.6 |

TABLE 3-continued
| $^1$H and $^{13}$C NMR data of Compound 3 (CDCl$_3$) | | |
|---|---|---|
| N° | $^1$H (Multiplicity, J) | $^{13}$C |
| 32 | 1.03 (s), 3H | 26.6 |
| 33 | — | 157.9 |
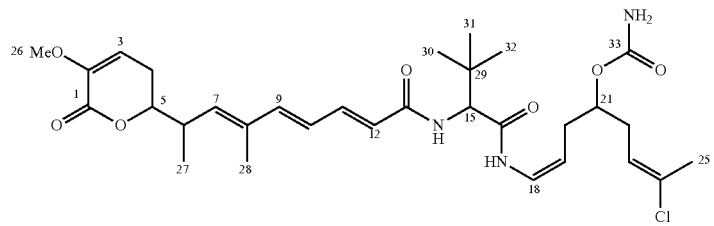
Compound 3
TABLE 4
| $^1$H and $^{13}$C NMR data of Compound 4 (CDCl$_3$) | | |
|---|---|---|
| N° | $^1$H (Multiplicity, J) | $^{13}$C |
| 1 | — | 161.6 |
| 2 | — | 145.2 |
| 3 | 5.63 (dd, 6.6, 2.7) | 108.2 |
| 4 | 2.44 (m) | 26.1 |
|   | 2.39 (m) |   |
| 5 | 4.25 (ddd, 11.3, 7.0, 4.0) | 81.9 |
| 6 | 2.85 (ddq, 9.9, 7.0, 6.7) | 37.1 |
| 7 | 5.29 (d, 9.9) | 134.1 |
| 8 | — | 133.8 |
| 9 | 6.15 (d, 11.6) | 140.2 |
| 10 | 7.31 (dd, 11.6, 11.6) | 124.4 |
| 11 | 6.90 (dd, 11.6, 11.6) | 137.5 |
| 12 | 5.72 (br d, 11.6) | 120.8 |
| 13 | — | 166.3 |
| 14 | 6.53 (d, 9.6) | — |
| 15 | 4.44 (d, 9.6) | 60.7 |
| 16 | — | 168.2 |
| 17 | 8.69 (d, 10.4) | — |
| 18 | 6.82 (ddd, 10.4, 9.1, 0.9) | 124.2 |
| 19 | 4.82 (m) | 105.8 |
| 20 | 2.46 (m) | 30.9 |
|   | 2.12 (ddd, 14.1, 8.0, 8.0) |   |
| 21 | 4.45 (m) | 75.6 |
| 22 | 2.35 (m), 2H | 31.4 |
| 23 | 5.40 (m) | 124.9 |
| 24 | 5.60 (m) | 127.1 |
| 25 | 1.63 (dd, 6.8, 1.0), 3H | 13.0 |
| 26 | 3.66 (s), 3H | 55.4 |
| 27 | 1.15 (d, 6.7), 3H | 16.4 |
| 28 | 1.82 (s), 3H | 17.1 |
| 29 | — | 34.8 |
| 30 | 1.04 (s), 3H | 26.7 |
| 31 | 1.04 (s), 3H | 26.7 |
| 32 | 1.04 (s), 3H | 26.7 |
| 33 | — | 157.6 |
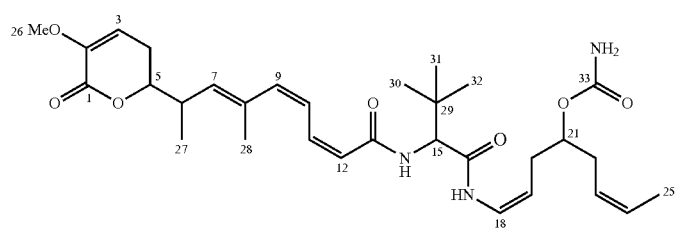
Compound 4

TABLE 5
$^1$H and $^{13}$C NMR data of Compound 5 (CDCl$_3$)
| N° | $^1$H (Multiplicity, J) | $^{13}$C |
|---|---|---|
| 1 | — | 161.7 |
| 2 | — | 145.1 |
| 3 | 5.64 (dd, 6.6, 2.6) | 108.3 |
| 4 | 2.48 (ddd, 17.4, 12.0, 2.6) | 26.0 |
|   | 2.37 (ddd, 17.4, 6.6, 3.9) |  |
| 5 | 4.28 (ddd, 12.0, 6.6, 3.9) | 81.9 |
| 6 | 2.85 (ddq, 9.7, 6.6, 6.7) | 37.0 |
| 7 | 5.31 (d, 9.7) | 134.1 |
| 8 | — | 133.6 |
| 9 | 6.17 (d, 11.5) | 140.3 |
| 10 | 7.31 (dd, 11.5, 11.5) | 124.5 |
| 11 | 6.93 (dd, 11.5, 11.5) | 137.6 |
| 12 | 5.73 (d, 11.5) | 120.5 |
| 13 | — | 166.5 |
| 14 | 6.54 (d, 9.2) | — |
| 15 | 4.46 (dd, 9.2, 6.4) | 58.5 |
| 16 | — | 169.1 |
| 17 | 8.69 (d, 10.7) | — |
| 18 | 6.84 (ddd, 10.7, 9.8, 0.9) | 124.5 |
| 19 | 4.80 (m) | 105.2 |
| 20 | 2.45 (m) | 30.7 |
|   | 2.10 (ddd, 15.0, 7.1, 6.2) |  |
| 21 | 4.44 (m) | 74.8 |
| 22 | 2.33 (m), 2H | 33.0 |
| 23 | 5.60 (br t, 7.1) | 122.4 |
| 24 | — | 132.0 |
| 25 | 2.06 (s), 3H | 21.0 |
| 26 | 3.66 (s), 3H | 55.4 |
| 27 | 1.15 (d, 6.7), 3H | 16.2 |
| 28 | 1.82 (br s), 3H | 17.1 |
| 29 | 2.22 (m) | 31.1 |
| 30 | 1.00 (d, 6.8), 3H | 19.3 |
| 31 | 0.96 (d, 6.8), 3H | 18.0 |
| 32 | — | 157.4 |
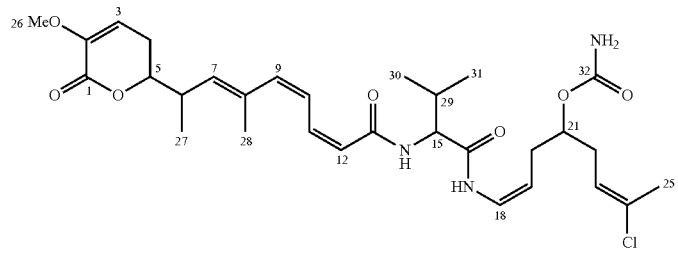
Compound 5
TABLE 6
$^1$H and $^{13}$C NMR data of Compound 6 (CDCl$_3$)
| N° | $^1$H (Multiplicity, J) | $^{13}$C |
|---|---|---|
| 1 | — | 161.5 |
| 2 | — | 145.2 |
| 3 | 5.61 (dd, 6.8, 2.8) | 108.2 |
| 4 | 2.41 (m), 2H | 26.6 |
| 5 | 4.18 (ddd, 11.6, 7.7, 4.2) | 81.6 |
| 6 | 2.88 (ddq, 10.0, 7.7, 6.6) | 37.4 |
| 7 | 5.47 (br d, 10.0) | 136.5 |
| 8 | — | 135.5 |
| 9 | 6.41 (d, 15.4) | 145.0 |
| 10 | 7.61 (dd, 15.4, 11.3) | 124.2 |
| 11 | 6.49 (dd, 11.3, 11.3) | 142.5 |
| 12 | 5.63 (d, 11.3) | 118.9 |
| 13 | — | 166.6 |
| 14 | 6.34 (d, 8.9) | — |
| 15 | 4.42 (dd, 8.9, 7.1) | 58.6 |
| 16 | — | 169.0 |

TABLE 6-continued

<sup>1</sup>H and <sup>13</sup>C NMR data of Compound 6 (CDCl<sub>3</sub>)

| N° | $^1$H (Multiplicity, J) | $^{13}$C |
|---|---|---|
| 17 | 8.59 (d, 10.8) | — |
| 18 | 6.84 (br dd, 10.8, 8.7) | 124.5 |
| 19 | 4.81 (m) | 105.5 |
| 20 | 2.42 (m) | 30.6 |
|    | 2.13 (ddd, 14.1, 7.5, 7.2) | |
| 21 | 4.49 (m) | 74.7 |
| 22 | 2.35 (m), 2H | 33.1 |
| 23 | 5.61 (m) | 122.3 |
| 24 | — | 132.1 |
| 25 | 2.07 (s), 3H | 21.0 |
| 26 | 3.65 (s), 3H | 55.4 |
| 27 | 1.15 (d, 6.6), 3H | 16.5 |
| 28 | 1.86 (s), 3H | 13.1 |
| 29 | 2.20 (m) | 30.9 |
| 30 | 1.01 (d, 6.7), 3H | 19.3 |
| 31 | 0.98 (d, 6.8), 3H | 18.2 |
| 32 | — | 157.0 |

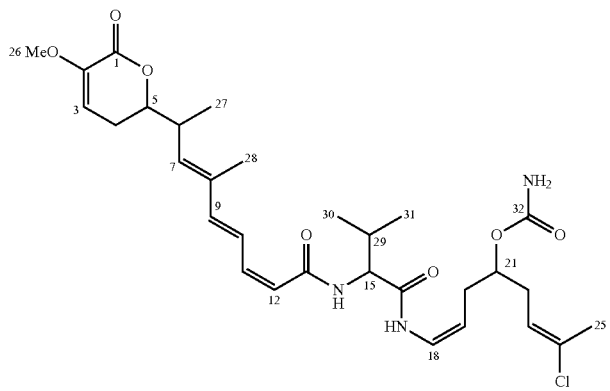

Compound 6

TABLE 7

$^1$H and $^{13}$C NMR data of Compound 7 (CDCl$_3$)

| N° | $^1$H (Multiplicity, J) | $^{13}$C |
|---|---|---|
| 1 | — | 161.5 |
| 2 | — | 145.3 |
| 3 | 5.62 (dd, 6.1, 3.2) | 108.1 |
| 4 | 2.43 (m) | 26.3 |
|   | 2.38 (m) | |
| 5 | 4.21 (ddd, 12.0, 7.0, 4.8) | 81.8 |
| 6 | 2.86 (ddq, 9.9, 7.0, 6.6) | 37.4 |
| 7 | 5.29 (d, 9.9) | 134.2 |
| 8 | — | 134.1 |
| 9 | 6.17 (d, 11.6) | 140.2 |
| 10 | 7.26 (dd, 11.6, 11.5) | 124.1 |
| 11 | 6.90 (dd, 11.5, 11.5) | 137.4 |
| 12 | 5.67 (d, 11.5) | 120.8 |
| 13 | — | 166.2 |
| 14 | 6.22 (d, 9.2) | — |
| 15 | 4.34 (d, 9.2) | 59.8 |
| 16 | — | 172.5 |
| 17 | 3.66 (s), 3H | 55.4 |
| 18 | 1.17 (d, 6.6), 3H | 16.7 |
| 19 | 1.85 (s), 3H | 17.2 |
| 20 | — | 34.5 |
| 21 | 1.05 (s), 3H | 26.6 |
| 22 | 1.05 (s), 3H | 26.6 |
| 23 | 1.05 (s), 3H | 26.6 |

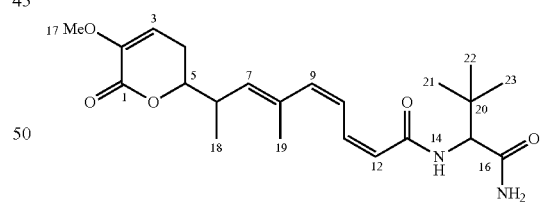

Compound 7

Example 4

Isolation of Compound 8

A fraction containing compound 1 (61.6 mg) coming from the extraction procedure disclosed in Example 3 was further purified by semipreparative HPLC (Symmetryprep C-18, 7 μm, 7.8×150 mm, isocratic H$_2$O:CH$_3$CN (55:45), flow: 2.3 mL/min, UV detection) and 0.9 mg of compound 8 were obtained in a pure form.

Compound 8: amorphous white solid. MS (ES) m/z 606.2 [M+H]$^+$, 628.3 [M+Na]$^+$; $^1$H (500 MHz) and $^{13}$C NMR (125 MHz) see Table 8.

TABLE 8
$^1$H and $^{13}$C NMR data of Compound 8 (CDCl$_3$)
| N° | $^1$H (Multiplicity, J) | $^{13}$C |
|---|---|---|
| 1 | — | 161.6 |
| 2 | — | 145.2 |
| 3 | 5.66 (br t, 4.6) | 108.4 |
| 4 | 2.45 (m), 2H | 26.6 |
| 5 | 4.21 (ddd, 7.7, 7.7, 7.7) | 81.7 |
| 6 | 2.85 (ddq, 10.0, 7.7, 6.7) | 37.4 |
| 7 | 5.35 (d, 10.0) | 135.1 |
| 8 | — | 134.6 |
| 9 | 6.16 (d, 11.7) | 140.6 |
| 10 | 6.06 (dd, 11.7, 11.7) | 125.6 |
| 11 | 7.71 (dd, 14.7, 11.7) | 137.9 |
| 12 | 5.95 (d, 14.7) | 124.5 |
| 13 | — | 166.0 |
| 14 | 6.35 (d, 9.5) | — |
| 15 | 4.47 (d, 9.5) | 61.0 |
| 16 | — | 168.3 |
| 17 | 8.65 (d, 10.8) | — |
| 18 | 6.83 (ddd, 10.8, 8.7, 1.0)) | 124.4 |
| 19 | 4.80 (m) | 105.2 |
| 20 | 2.11 (ddd, 14.2, 8.1, 7.8) 2.45 (m) | 30.7 |
| 21 | 4.46 (m) | 75.0 |
| 22 | 2.34 (t, 6.7), 2H | 33.0 |
| 23 | 5.60 (td, 7.8, 1.2) | 122.3 |
| 24 | — | 132.0 |
| 25 | 2.06 (s), 3H | 21.0 |
| 26 | 3.66 (s), 3H | 55.4 |
| 27 | 1.17 (d, 6.7), 3H | 16.6 |
| 28 | 1.91 (d, 0.7), 3H | 17.0 |
| 29 | — | 34.8 |
| 30 | 1.04 (s), 3H | 26.6 |
| 31 | 1.04 (s), 3H | 26.6 |
| 32 | 1.04 (s), 3H | 26.6 |
| 33 | — | 157.1 |
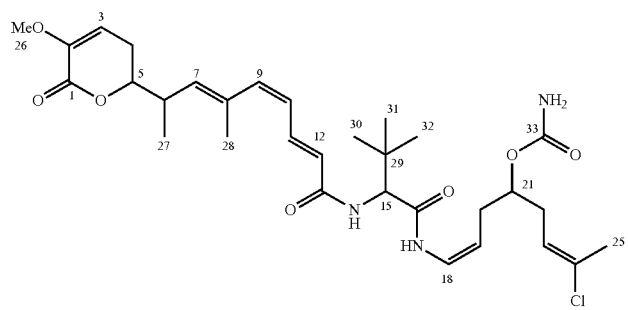
Compound 8
Example 5
Synthesis of Fragment A
Scheme 2 provides several examples of synthesis of fragment A, in accordance with the nomenclature provided in Scheme 1.
Scheme 2
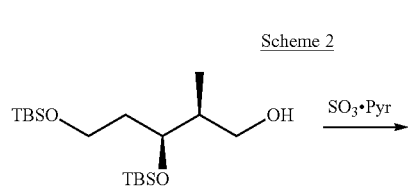
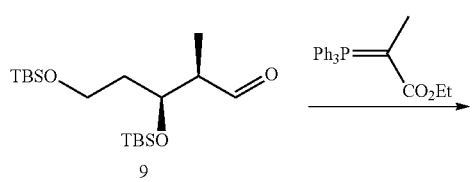
-continued
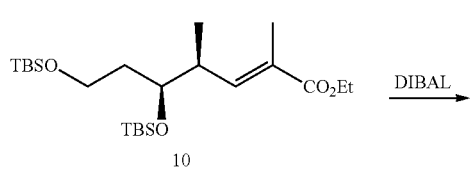

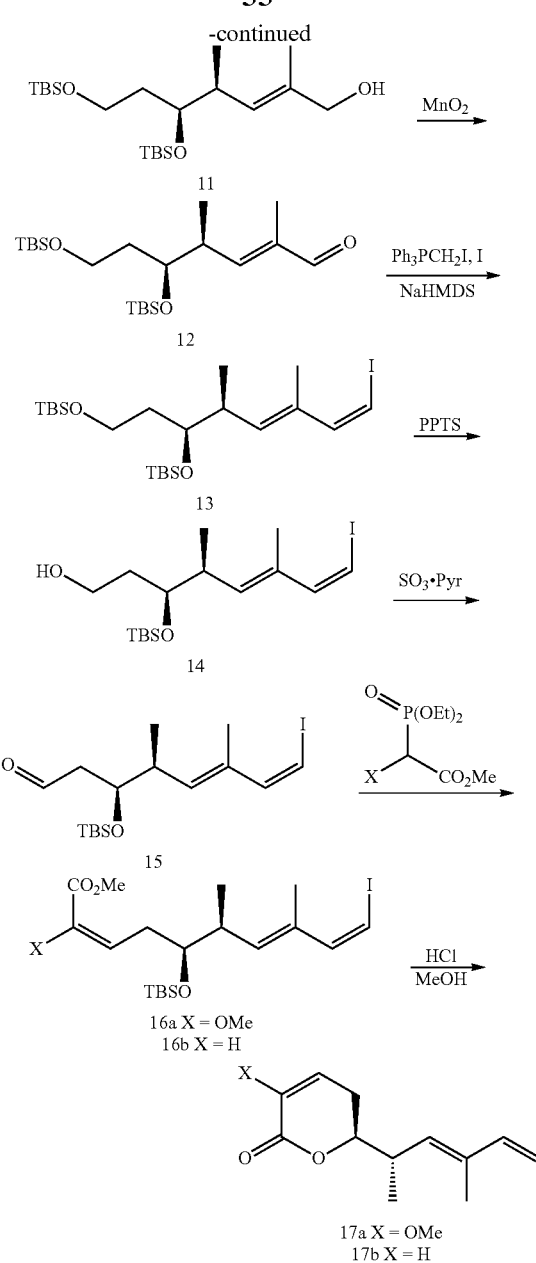

Synthesis of Intermediate 9

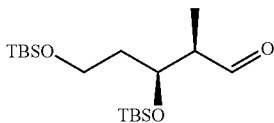 [SMILES: C[C@@H](C=O)[C@H](CCO[Si](C)(C)C(C)(C)C)O[Si](C)(C)C(C)(C)C]

To a 0° C. solution of (2S,3S)-3,5-Bis{[(tert-butyl)dimethylsilyl]oxy}-4-methylpentan-1-ol (P. Phukan, S. Sasmal and M. E. Maier *Eur. J. Org. Chem.* 2003, 1733-1740) (50 g, 0.14 mol) in a mixture of Dichloromethane/DMSO (331 mL/149 mL), Et$_3$N (96.1 mL, 0.69 mol) was added via addition funnel. After 10 min, SO$_3$·Pyr (54.8 g, 0.34 mol) was added portionwise and the solution was stirred for another 2 h at 0° C. Then, it was diluted with dichloromethane (800 ml) and quenched with HCl (0.5N, 800 mL). The organic layer was decanted, dried over MgSO$_4$ and concentrated in vacuo. Purification by column chromatography (hexane/EtOAc 100:0 to 10:1) afforded 45 g (yield: 90%) of aldehyde 9.

$^1$H-RMN (CDCl$_3$, 300 MHz) δ: 9.79 (s, 1H), 4.30 (m, 1H), 3.65 (m, 2H), 2.51 (m, 1H), 1.69 (m, 2H), 1.04 (d, 3H, J=6.9 Hz), 0.85-0.88 (m, 18H), 0.03-0.07 (m, 12H).

$^{13}$C-RMN (CDCl$_3$, 75 MHz) δ: 205.4, 69.4, 59.6, 51.7, 37.5, 26.1, 26.0, 18.4, 18.2, 8.0, −4.3, −4.5, −5.2.

Synthesis of Intermediate 10

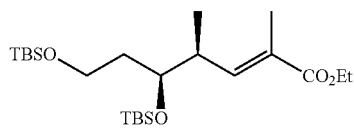 [SMILES: CCOC(=O)/C(C)=C/[C@H](C)[C@H](CCO[Si](C)(C)C(C)(C)C)O[Si](C)(C)C(C)(C)C]

Over a solution of aldehyde 9 (45 g, 0.12 mol) in toluene (625 mL) Carboethoxyethylidene-triphenylphosphorane (113 g, 0.31 mol) was added and the mixture was heated at 60° C. over 17 h. Then, the solvent was removed under reduced pressure and the resulting oil was purified by column chromatography (hexane/EtOAc 100:0 to 10:1) affording 53.3 g (yield: 96%) of ester compound 10.

1H-RMN (CDCl$_3$, 300 MHz) δ: 6.71 (dd, 1H, J=1.5, 10.2 Hz), 4.19 (m, 2H), 3.77 (m, 1H), 3.66 (m, 2H), 2.61 (m, 1H), 1.85 (d, 3H, J=1.5 Hz), 1.68 (m, 2H), 1.30 (t, 3H, J=7.2 Hz), 0.98 (d, 3H, 6.9 Hz), 0.90 (m, 18H), 0.05 (m, 12H).

$^{13}$C-RMN (CDCl$_3$, 75 MHz) δ: 168.3, 145.4, 126.7, 72.2, 60.4, 59.7, 38.4, 38.0, 25.9, 18.2, 18.1, 14.3, 14.3, 12.6, −4.4, −4.6, −5.4.

Synthesis of Intermediate 11

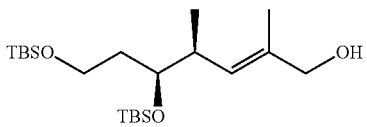 [SMILES: C/C(=C\[C@H](C)[C@H](CCO[Si](C)(C)C(C)(C)C)O[Si](C)(C)C(C)(C)C)CO]

Over a −78° C. cooled solution of ester 10 (46.7 g, 0.105 mol) in anhydrous THF (525 mL) under argon atmosphere, Diisobutylaluminum hydride (DIBAL) 1M in toluene (231 mL, 0.231 mol) was added over a period of 10 min and the mixture was stirred at −78° C. After 4 hours the reaction was quenched with MeOH (10 mL) and a saturated solution of sodium potassium tartrate was added (800 mL) and diluted with EtOAc (1000 mL). This mixture was stirred for 2 h and then the organic layer was decanted. The aqueous residue was extracted with additional EtOAc (2×400 mL) and the combined organic layers were dried (Na$_2$SO$_4$) and the solvent was evaporated. The resulting oil was purified by column chromatography (hexane/EtOAc 20:1 to 10:1) affording 32.5 g (yield: 77%) of alcohol 11.

$^1$H-RMN (CDCl$_3$, 300 MHz) δ: 5.31 (d, 1H, J=9.6 Hz), 3.98 (m, 2H), 3.66 (m, 3H), 2.49 (m, 1H), 1.67 (s, 3H), 1.70-1.62 (m, 2H), 0.91 (d, 3H, J=6.9 Hz), 0.88 (m, 18H), 0.03 (m, 12H).

$^{13}$C-RMN (CDCl$_3$, 75 MHz) δ: 133.9, 129.8, 73.1, 69.1, 59.9, 37.8, 37.5, 25.9, 18.3, 18.1, 15.9, 13.9, −4.4, −4.4, −5.3.

Synthesis of Intermediate 12

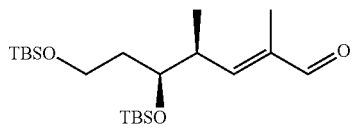 [SMILES: C/C(C=O)=C\[C@H](C)[C@H](CCO[Si](C)(C)C(C)(C)C)O[Si](C)(C)C(C)(C)C]

Over a solution of alcohol 11 (31.2 g, 77.5 mmol) in ethyl ether (387 mL) under argon atmosphere, MnO$_2$ (101 g, 1.16 mol) were added and the mixture was stirred at room temperature for 2 hours. This mixture was filtrated over a silica gel column eluting with EtOAc (3 L) and the resulting solution was dried under reduced pressure to afford 29.1 g (yield: 94%) of aldehyde 12.

$^1$H-RMN (CDCl$_3$, 300 MHz) δ: 9.37 (s, 1H), 6.44 (d, 1H, J=9.6 Hz), 3.82 (dd, 1H, J=6.3, 10.8 Hz), 3.65 (m, 2H), 2.82 (m, 1H), 1.74 (s, 3H), 1.67 (m, 2H), 1.02 (d, 3H, J=6.9 Hz), 0.86 (s, 18H), 0.04-0.01 (m, 12H).

$^{13}$C-RMN (CDCl$_3$, 75 MHz) δ: 195.4, 157.8, 138.3, 134.5, 72.0, 59.5, 36.7, 37.5, 25.8, 18.2, 18.1, 14.3, 9.4, −4.4, −4.5, −5.4.

Synthesis of Intermediate 13

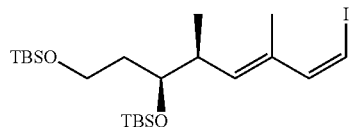 [SMILES: CC(/C=C\I)=C\[C@H](C)[C@H](CCO[Si](C)(C)C(C)(C)C)O[Si](C)(C)C(C)(C)C]

To a suspension of iodomethyl triphenylphosphonium iodide (Gilbert Stork, KZ. *Tetrahedron letters* 1989, 30(17), 2173) (96.3 g, 181.7 mmol) in THF (727 mL) at 0° C., a 1M solution of sodium hexamethyldisilazane (NaHMDS) (181.7 mL, 181.7 mmol) was slowly added, via addition funnel, over a period of 10 min. After stirring for an additional 5 min, the solution was cooled to −78° C. and 1,3-Dimethyl-3,4,5,6-tetrahydro-2(1H)-pyrimidinone (DMPU) (43.9 mL, 363.4 mmol) was then added via cannula, followed by the addition of aldehyde 12 (29.1 g, 72.7 mmol) dissolved in THF (727 mL). The temperature was kept at −78° C. while the reaction mixture was stirred for 2 hours. Hexane (1 L) was added and the resulting slurry was filtrated over celite and washed with additional hexane (3 L). The filtrate was evaporated under reduced pressure and the resulting oil was purified by column chromatography (hexane/EtOAc 100:0 to 20:1) affording 32 g (yield: 84%) of iodide 13.

$^1$H-RMN (CDCl$_3$, 300 MHz) δ: 6.73 (d, 1H, J=8.4 Hz), 6.09 (dd, 1H, J=8.4, 1.2 Hz), 5.57 (dd, 1H, J=9.6, 1.2 Hz), 3.63-3.71 (m, 3H), 2.58 (m, 1H), 1.90 (s, 3H), 1.70 (m, 2H), 0.96 (dd, 3H, J=6.6, 1.2 Hz), 0.88 (s, 18H), 0.04 (m, 12H).

$^{13}$C-RMN (CDCl$_3$, 75 MHz) δ: 142.3, 138.1, 131.8, 74.6, 72.9, 59.8, 38.1, 37.9, 26.0, 18.3, 18.2, 15.7, 15.7, −4.4, −5.2, −5.2.

Synthesis of Intermediate 14

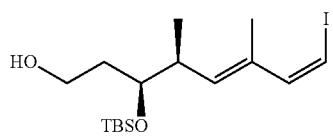 [SMILES: CC(/C=C\I)=C\[C@H](C)[C@H](CCO)O[Si](C)(C)C(C)(C)C]

To a solution of iodide 13 (12 g, 22.9 mmol) in EtOH (114 mL) pyridinium p-toluenesulfonate (PPTS) (2.01 g, 8.0 mmol) was added and the reaction mixture was stirred at room temperature for 25 hours. Then the solvent was removed under reduced pressure and the resulting oil was purified by column chromatography (hexane/EtOAc 10:1) affording 8.7 g (yield: 93%) of alcohol 14.

$^1$H-RMN (CDCl$_3$, 300 MHz) δ: 6.69 (d, 1H, J=8.4 Hz), 6.12 (d, 1H, J=8.4 Hz), 5.47 (d, 1H, J=9.9 Hz), 3.67-3.87 (m, 4H), 2.71 (m, 1H), 1.89 (s, 3H), 1.73-1.86 (m, 2H), 1.01 (d, 3H, J=6.9 Hz), 0.91 (s, 9H), 0.087-0.115 (m, 6H).

$^{13}$C-RMN (CDCl$_3$, 75 MHz) δ: 142.4, 136.4, 132.6, 75.8, 75.2, 60.0, 38.1, 36.4, 26.1, 18.2, 17.1, 16.0, −4.1, −4.2.

Synthesis of Intermediate 15

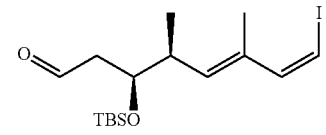 [SMILES: CC(/C=C\I)=C\[C@H](C)[C@H](CC=O)O[Si](C)(C)C(C)(C)C]

To a 0° C. solution of alcohol 14 (8.7 g, 21.2 mmol) in a mixture of Dichloromethane/DMSO (50.9 mL/22.9 mL), Et$_3$N (14.8 mL, 106 mmol) was added via addition funnel. After 10 min, SO$_3$.Pyr (8.43 g, 53.0 mol) was added portionwise and the solution was stirred for another 2 h at 0° C. Then, it was diluted with Dichloromethane (800 mL) and quenched with HCl (0.5N, 50 mL). The organic layer was decanted, dried over MgSO$_4$ and concentrated in vacuo. Purification by column chromatography (hexane/EtOAc 10:1) afforded 6.9 g (yield: 80%) of aldehyde 15.

$^1$H-RMN (CDCl$_3$, 300 MHz) δ: 9.89 (t, 1H, J=1.5 Hz), 6.67 (d, 1H, J=8.4 Hz), 6.13 (d, 1H, J=8.4 Hz), 5.43 (d, 1H, J=10.2 Hz), 3.98 (m, 1H), 2.59-2.69 (m, 3H), 1.85 (s, 3H), 1.01 (d, 3H, J=6.6 Hz), 0.86 (s, 9H), 0.06 (s, 3H), 0.03 (s, 3H).

$^{13}$C-RMN (CDCl$_3$, 75 MHz) δ: 201.8, 141.9, 135.2, 133.3, 76.3, 71.9, 49.3, 39.3, 25.8, 18.0, 16.7, 15.9, −4.4, −4.5.

Synthesis of Intermediate 16a

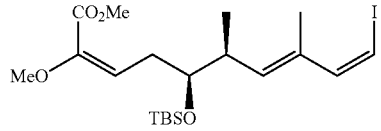 [SMILES: COC(=O)/C(=C\C[C@H](O[Si](C)(C)C(C)(C)C)[C@@H](C)/C=C(C)/C=C\I)OC]

To a solution of Diethyl(methoxy[methoxycarbonyl]methyl)phosphonate (5.51 g, 14.45 mmol) and 18-crown-6 (11.5 g, 43.34 mmol) in dry THF (390 mL) stirred under argon atmosphere at −78° C., a 0.5 M Potassium bis(trimethylsilyl)amide solution (KHMDS) (43.34 mL, 21.67 mmol) was added dropwise. After 15 min aldehyde 15 (5.9 g, 14.45 mmol) in dry THF was added dropwise over a period of 30 min and stirred at −78° C. for 90 min. Then, the reaction was quenched with a saturated NH$_4$Cl solution (200 mL), warmed to room temperature and diluted with Dichloromethane (1000 mL). The organic phase was dried (Na$_2$SO$_4$) and evaporated at reduced pressure. Purification by column chromatography (hexane/Et$_2$O 20:1) afforded pure 4.2 g (59%) of (E)-16a.

$^1$H-RMN (CDCl$_3$, 300 MHz) δ: 6.70 (d, 1H, J=8.4 Hz), 6.08 (d, 1H, J=8.4 Hz), 5.47 (d, 1H, J=9.9 Hz), 5.37 (t, 1H, J=7.2 Hz), 3.78 (s, 3H), 3.60 (s, 3H), 3.60 (m, 1H), 2.79 (m, 1H), 2.52-2.67 (m, 2H), 1.83 (s, 3H), 0.99 (d, 3H, J=6.6 Hz), 0.89 (s, 9H), 0.05 (s, 3H), 0.04 (s, 3H).

$^{13}$C-RMN (CDCl$_3$, 75 MHz) δ: 163.7, 145.9, 142.1, 137.3, 132.1, 110.4, 75.4, 74.8, 55.4, 51.9, 38.1, 32.3, 25.9, 18.1, 16.5, 15.7, −4.3, −4.5.

Synthesis of Intermediate 16b

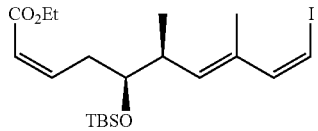 [SMILES: CCOC(=O)/C=C\C[C@H](O[Si](C)(C)C(C)(C)C)[C@@H](C)/C=C(C)/C=C\I]

To a solution of Ethyl[bis(2,2,2-trifluoroethoxy)phosphinyl]acetate (0.16 mL, 0.66 mmol) and 18-crown-6 (350 mg, 1.32 mmol) in dry THF (2.4 mL) stirred under argon atmosphere at 0° C., KHMDS (1.23 mL, 0.62 mmol) was added dropwise. After 30 min aldehyde 15 (180 mg, 0.44 mmol) in dry THF was added dropwise and stirred at −78° C. for 60 min. Then, the reaction was quenched with saturated NH$_4$Cl solution, warmed to room temperature and diluted with EtOAc. The organic phase was dried (Na$_2$SO$_4$) and evaporated at reduced pressure. Purification by column chromatography (hexane/EtOAc 100:1 to 15:1) afforded 172 mg (yield: 82%) of (Z)-16b.

$^1$H-RMN (CDCl$_3$, 300 MHz) δ: 6.70 (d, 1H, J=8.7 Hz), 6.44-6.36 (m, 1H), 6.09 (d, 1H, J=8.7 Hz), 5.86-5.81 (m, 1H), 5.47 (d, 1H, J=9.9 Hz), 4.14 (q, 2H, J=7.2 Hz), 3.69-3.64 (m, 1H), 3.06-3.00 (m, 1H), 2.85-2.75 (m, 1H), 2.59-2.51 (m, 1H), 1.84 (s, 3H), 1.28 (t, 3H, J=7.2 Hz), 1.00 (d, 3H, J=6.6 Hz), 0.89 (s, 9H), 0.06 (s, 3H), 0.05 (s, 3H).

MS (ES) m/z 501.0 [M+Na]$^+$

Synthesis of Intermediate 17a

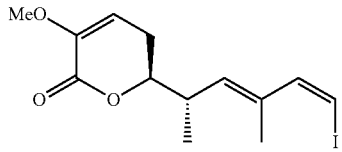 [SMILES: COC1=CC[C@@H]([C@@H](C)/C=C(C)/C=C\I)OC1=O]

To a solution of ester 16a (4.15 g, 8.39 mmol) in MeOH (125 mL) at room temperature, HCl 37% (1.04 mL) was added and the reaction mixture was stirred for 6 hours. Then the mixture was neutralized with a saturated solution of NaHCO$_3$ (pH 7-8) and the organic solvent was evaporated under reduced pressure. The resulting suspension was extracted with Dichloromethane (3×200 mL), dried and evaporated. Filtration by column chromatography (hexane/EtOAc 10:1 to 2:1) afforded 2.76 g (yield: 94%) of lactone 17a.

$^1$H-RMN (500 MHz, CDCl$_3$) δ: 6.68 (d, 1H, J=9.0 Hz), 6.20 (d, 1H, J=8.5 Hz), 5.63 (dd, 1H, J=2.5, 6.5 Hz), 5.43 (d, 1H, J=10.0 Hz), 4.19 (m, 1H), 3.65 (s, 3H), 2.84 (m, 1H), 2.55 (m, 1H), 2.43 (dc, J=1H, 3.0, 12.0, 15.0, 18.0 Hz), 1.87 (s, 3H), 1.16 (d, 3H, J=6.5 Hz).

$^{13}$C-RMN (125 MHz, CDCl$_3$) δ: 161.6, 145.2, 141.8, 134.4, 132.7, 108.3, 81.7, 77.4, 55.4, 37.1, 26.6, 16.5, 16.1.

Synthesis of Intermediate 17b

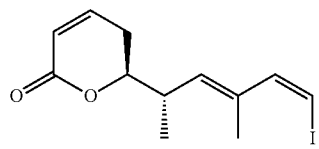

To a solution of ester 16b (172 mg, 0.36 mmol) in MeOH (4.5 mL) at room temperature, HCl 37% (0.03 mL) was added and the reaction mixture was stirred for 3 hours. Then the mixture was neutralized with a saturated solution of NaHCO$_3$ (pH 7-8) and the organic solvent was evaporated under reduced pressure. The resulting suspension was extracted with dichloromethane, dried and evaporated. Filtration by column chromatography (hexane/EtOAc 10:1 to 5:1) afforded 70 mg (yield: 61%) of lactone 17b.

$^1$H-RMN (CDCl$_3$, 300 MHz) δ: 6.91-6.85 (m, 1H), 6.68 (d, 1H, J=8.4 Hz), 6.62 (d, 1H, J=8.4 Hz), 6.02 (dd, 1H, J=2.7, 9.6 Hz), 5.45 (d, 1H, J=9.9 Hz), 4.19 (m, 1H), 3.65 (s, 3H), 4.26-4.18 (m, 1H), 2.92-2.79 (m, 1H), 2.57-2.48 (m, 1H), 2.39-2.28 (m, 1H), 1.88 (s, 3H), 1.17 (d, 3H, J=6.6 Hz).

Example 6

Synthesis of Fragment D

Scheme 3 provides several examples of synthesis of fragment D, in accordance with the nomenclature provided in Scheme 1.

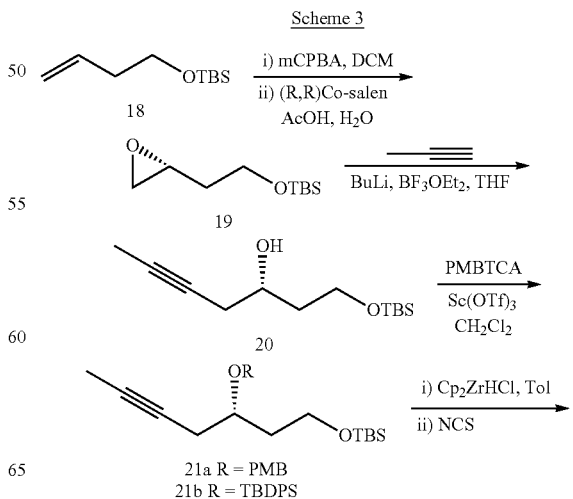

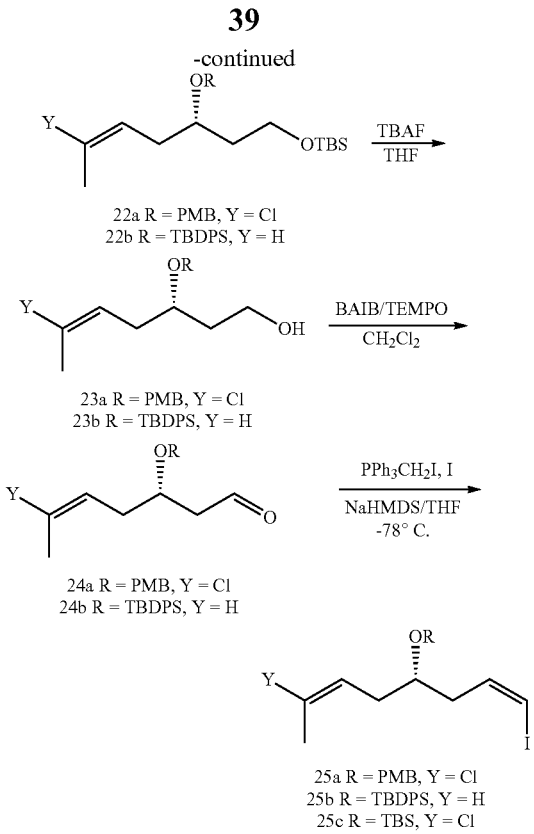

22a R = PMB, Y = Cl
22b R = TBDPS, Y = H

23a R = PMB, Y = Cl
23b R = TBDPS, Y = H

24a R = PMB, Y = Cl
24b R = TBDPS, Y = H

25a R = PMB, Y = Cl
25b R = TBDPS, Y = H
25c R = TBS, Y = Cl

Synthesis of Intermediate 19

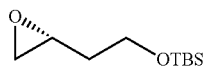

To a solution of intermediate 18 (72.3 g) in dichloromethane (DCM) (918 mL) at room temperature 3-Chloroperbenzoic acid (m-CPBA) (100 g, 0.58 mol) was added in portionwise, and the mixture was stirred at room temperature for 18 h. The white precipitate was quenched with saturated solution of NaHCO$_3$, extracted with DCM (3×250 mL) and washed again with saturated aqueous solution of NaHCO$_3$ (3×250 mL). The organic layers were combined, dried over Na$_2$SO$_4$ and concentrated in vacuo. The resulting oil was purified on silica gel (Hexane-AcOEt; 15:1) to provide epoxide as a colourless oil (64.5 g, 82%). To a solution of racemic epoxide (30 g) in anhydrous THF (7.5 mL) (R,R)Co (II) complex (448 mg, 0.74 mmol) was added, followed by AcOH (0.14 mL). The solution was cooled to 0° C. and water (1.2 mL) was added dropwise. The reaction was allowed to warm to room temperature and stir 18 h. After that time the volatile materials were concentrated in vacuo and the crude was directly loaded on a silica gel column. Flash chromatography using Hexane/EtOAc (15:1 to 12:1) as eluant, provided chiral epoxide (+)-19 (13.6 g, yield: 46%) as a colourless oil.

[α]$_D$=+14.1 (c=1, CHCl$_3$).

$^1$H NMR (CDCl$_3$, 300 MHz) δ: 3.74 (t, 2H, J=6.3 Hz), 3.01 (m, 1H), 2.74 (t, 1H, J=4.6 Hz), 2.48 (dd, 1H, J=5.1, 3.1 Hz), 1.70 (m, 2H), 0.87 (s, 9H), 0.04 (s, 6H).

$^{13}$C RMN (CDCl$_3$, 75 MHz) δ: 60.2, 50.2, 47.3, 36.1, 26.1, 18.4, −5.2.

Synthesis of Intermediate 20

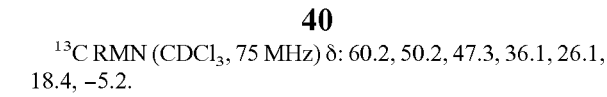

Propyne was condensed at −78° C. and dissolved in anhydrous THF (165 mL). n-Butyllithium was added dropwise under Ar over 30 min, and the resultant white suspension was stirred for an additional 30 min at −78° C. A solution of (+)(R)-2-[2-(tert-butyldimethylsilyloxy)ethyl]oxirane 19 (23.7 g) in anhydrous THF (125 mL) was then added dropwise followed by addition of BF$_3$OEt$_2$. The mixture was stirred for 1 h at −78° C. and for an additional hour at 0° C. The reaction was quenched with saturated aqueous solution of NH$_4$Cl (150 mL) and extracted with Et$_2$O (3×150 mL). The combined organic layers were dried over NaSO$_4$, filtered and concentrated. Flash chromatography (hexane/EtOAc 10:1 to 1:1) provided 22.7 g, (yield: 80%) of alcohol 20 as a colourless oil. [α]$_D$=+5.6 (c=0.1, CHCl$_3$).

$^1$H-RMN (500 MHz, CDCl$_3$) δ: 3.75-3.90 (m, 3H), 3.47 (d, 1H, J=2.7 Hz OH), 2.34 (m, 2H), 1.79, (t, 3H, J=2.4 Hz), 1.75 (m, 2H), 0.89 (s, 9H), 0.07 (s, 6H).

$^{13}$C-RMN (125 MHz, CDCl$_3$) δ: 77.8, 75.8, 70.7, 62.4, 37.6, 27.6, 26.1, 18.3, 3.7, −5.3, −5.4.

MS (ES) m/z 243.2 [M+H]$^+$, 265.2 [M+Na]$^+$

Synthesis of Intermediate 21a

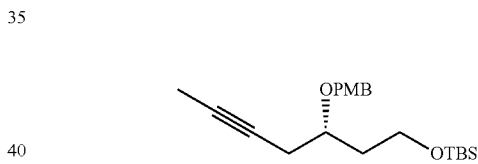

A solution of intermediate 20 (22.7 g) and p-methoxybenzyltrichloroacetimidate (PMBTCA) in DCM was treated with Sc(OTf)$_3$. The mixture was stirred at room temperature for 2 h (TLC checking) and the reaction was concentrated in vacuo and purified by column chromatography (hexane/EtOAc 50:1 to 15:1) to give 21a as yellow oil (18.3 g; yield: 55%).

$^1$H NMR (CDCl$_3$, 300 MHz) δ: 7.25 (d, 2H, J=8.7 Hz), 6.90 (d, 2H, J=8.7 Hz), 4.45 (m, 2H), 3.80 (s, 3H), 3.65 (m, 3H), 2.40 (m, 2H), 1.82 (m, 2H), 1.79 (t, 3H, J=2.4 Hz), 0.92 (s, 9H), 0.05 (s, 6H).

Synthesis of Intermediate 21b

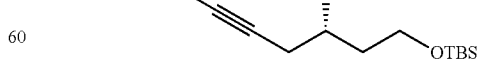

A solution of alcohol 20 (2.88 g, 11.9 mmol), tert-butyldiphenylsilyl chloride (4.39 mL, 16.89 mmol), and 4-(dimethylamino)pyridine (43.6 mg) in N,N-dimethylformamide (DMF) (14 mL) was stirred overnight at room temperature. The mixture was diluted with water and extracted with Et$_2$O, and the organic phase was washed with brine, dried over Na₂SO₄, filtered and concentrated. Flash chromatography (Hex/EtOAc, 95:1) gave the silyl ester 21b (5.3 g, yield: 93%) as a colourless liquid.

¹H NMR (CDCl₃, 300 MHz) δ: 7.70-7.66 (m, 4H), 7.40-7.34 (m, 6H), 3.99-3.95 (m, 1H), 3.70-3.62 (m, 2H), 2.23-2.22 (m, 2H), 1.84-1.81 (m, 2H), 1.69 (t, 3H, J=2.7 Hz), 1.05 (s, 9H), 0.84 (s, 9H), 0.01 (s, 6H).

¹³C-RMN (CDCl₃, 75 MHz) δ: 136.1; 134.6; 129.7; 127.8; 77.8; 76.2; 69.9; 60.1; 39.6; 27.5; 27.2; 26.2; 19.6; 18.5; 3.7; −5.1.

Synthesis of Intermediate 22a

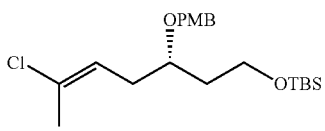

To a solution of 21a in anhydrous toluene, under Ar and at 0° C. Schwartz's reagent (Bis(cyclopentadienyl)zirconium (IV) chloride hydride, Cp₂ZrHCl) was added and the reaction was stirred 5 min at room temperature. The reaction temperature was increased to 50° C. over a period of 20 min and stirred at 50° C. for 2.30 h. During this time the reaction solution turned of orange colour. The reaction was cooled to 0° C. and N-chlorosuccinimide was added in one portion. Stirring was continued for 30 min at room temperature and the reaction was diluted with Hexane/EtOAc (95:5; 500 mL). Removing of the solid by filtration and evaporation of volatiles provided 22a as yellow oil which was used without further purification (15.1 g; yield: 86%).

[α]_D=+20.5 (c=1, CHCl₃).

¹H NMR (CDCl₃, 300 MHz) δ: 7.25 (d, 2H, J=8.7 Hz), 6.87 (d, 2H, J=8.7 Hz), 5.64 (td, 1H, J=7.8, 0.9 Hz), 4.45 (q, 2H, J=11.1 Hz), 3.80 (s, 3H), 3.70 (m, 2H), 3.62 (m, 1H), 2.27 (t, 2H, J=6.9 Hz), 2.03 (s, 3H), 1.70 (m, 2H), 0.89 (s, 9H), 0.05 (s, 6H).

¹³C RMN (75 MHz, CDCl₃) δ: 159.4, 130.9, 130.7, 129.6, 124.2, 114.0, 75.2, 71.4, 59.8, 55.5, 37.7, 33.8, 26.1, 21.2, 18.5, −5.1.

Synthesis of Intermediate 22b

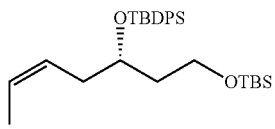

A flask containing a mixture of 21b (4.73 g, 9.85 mmol), quinoline (0.582 mL, 4.92 mmol) and lindlar catalyst (2.18 g) in ethyl acetate was evacuated and flushed with H₂. The reaction mixture was stirred at room temperature under H₂ (1 atm) for 2 h and then filtered through a plug of celite. The plug was rinsed with ethyl acetate and the combined filtrates were washed with 0.1% HCl. The organic layer was dried over Na₂SO₄, filtered and concentrated to afford intermediate 22b (4.27 g, yield: 90%) as a colourless oil that was used without further purification.

¹H NMR (CDCl₃, 300 MHz) δ: 7.70-7.67 (m, 4H), 7.44-7.36 (m, 6H), 5.48 (m, 1H), 5.36-5.27 (m, 1H), 3.95-3.87 (m, 1H), 3.71-3.55 (m, 2H), 2.16 (dd, 2H, J=6.9, 6.3 Hz), 1.73-1.66 (m, 2H), 1.41 (dd, 3H, J=6.6, 1.2 Hz), 1.05 (s, 9H), 0.84 (s, 9H), −0.02 (s, 6H).

¹³C-RMN (CDCl₃, 75 MHz) δ: 136.2; 134.8; 129.8; 127.8; 126.4; 125.8; 70.9; 60.4; 39.6; 34.8; 27.3; 26.2; 19.7; 18.5; 13.1; −5.1.

Synthesis of Intermediate 23a

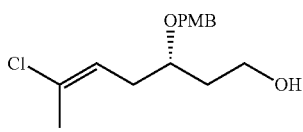

To a solution of 22a (23 g) in anhydrous THF under Ar and at 0° C. a solution of Tetrabutylammonium fluoride (TBAF) was added dropwise over a period of 20 min (the solution turned red). The reaction mixture was stirred at room temperature for 2 h, and then was quenched with saturated aqueous solution of NH₄Cl (200 mL). The combined layers were separated and the aqueous phase was extracted thoroughly with EtOAc (3×150 mL). The combined organic layers were dried over NaSO₄, filtered and concentrated. Flash chromatography (hexane/EtOAc 4:1 to 1:1) provided 23a as a colourless oil (11.9 g; yield: 73%).

¹H NMR (CDCl₃, 300 MHz) δ: 7.25 (d, 2H, J=8.7 Hz), 6.86 (d, 2H, J=8.7 Hz), 5.62 (t, 1H, J=7.8 Hz), 4.45 (m, 2H), 3.80 (s, 3H), 3.70 (m, 3H), 2.35 (m, 2H), 2.03 (s, 3H), 1.75 (m, 2H).

Synthesis of Intermediate 23b

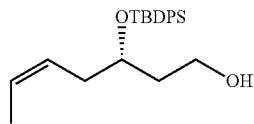

PPTS (837.7 mg, 3.33 mmol) was added in one portion to a solution of 22b (4 g, 8.33 mmol) in ethanol (80 mL). The reaction mixture was stirred at room temperature for 7 h and then was concentrated. The residue was diluted in DCM and washed with a saturated solution of NaHCO₃. The organic layer was extracted, dried over Na₂SO₄, filtered and concentrated. Flash chromatography (Hex/EtOAc, 95:1) gave the silyl eter 23b (2.12 g, yield: 69%) as a colourless oil.

¹H NMR (CDCl₃, 300 MHz) δ: 7.73-7.69 (m, 4H), 7.44-7.36 (m, 6H), 5.44-5.38 (m, 1H), 5.21-5.17 (m, 1H), 4.01-3.94 (m, 1H), 3.84-3.76 (m, 1H), 3.69-3.64 (m, 1H), 2.32-2.14 (m, 2H), 1.89-1.78 (m, 1H), 1.70-1.60 (m, 1H), 1.37 (d, 3H, J=6.9 Hz), 1.07 (s, 9H).

¹³C-RMN (CDCl₃, 75 MHz) δ: 136.2; 134.1; 130.0; 127.8; 126.3; 125.9; 72.3; 60.1; 37.7; 34.3; 27.2; 19.5; 13.0.

Synthesis of Intermediate 24a

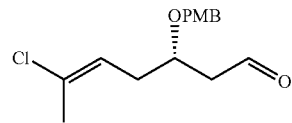

(Diacetoxyiodo)benzene (BAIB) (11.5 g, 35.7 mmol) was added to a solution of alcohol 23a (9.2 g, 32 4 mmol) and 2,2,6,6-Tetramethylpiperidine 1-oxyl (TEMPO) (515 mg, 3.3 mmol) in dichloromethane anhydrous (92 mL). The reaction mixture was stirred at room temperature for 20 h until the alcohol was no longer detectable (TLC), and then it was quenched with a saturated aqueous solution of NH$_4$Cl and extracted with DCM (3×100 mL). The combined organic phases were dried over Na$_2$SO$_4$, filtered and concentrated. The residue was purified by flash chromatography (Hexane/EtOAc 4:1 to 1:1) to afford 24a as colourless oil (6.3 g; yield: 70%)

$^1$H NMR (CDCl$_3$, 300 MHz) δ: 9.78 (s, 1H), 7.25 (d, 2H, J=8.7 Hz), 6.85 (d, 2H, J=8.7 Hz), 5.64 (t, 1H, J=7.8 Hz), 4.45 (q, 2H, J=11.1 Hz), 4.02 (m, 1H), 3.80 (s, 3H), 2.60 (m, 2H), 2.35 (m, 2H), 2.03 (s, 3H).

$^{13}$C RMN (CDCl$_3$, 75 MHz) δ: 201, 159.6, 132.1, 130.1, 129.7, 122.8, 114.1, 73.3, 71.5, 55.5, 48.3, 33.5, 21.3.

Synthesis of Intermediate 24b

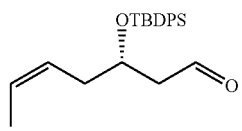

BAIB (1.97 g, 6.11 mmol) was added to a solution of alcohol 23b (2.05 g, 5.56 mmol) and TEMPO (86.87 mg, 0.56 mmol) in 25 mL of DCM. The reaction mixture was stirred at room temperature for 16-18 h until the alcohol was no longer detectable (TLC), and then it was quenched with a saturated aqueous solution of NH$_4$Cl, and extracted with DCM. The combined organic phases were dried over Na$_2$SO$_4$, filtered and concentrated. The residue was purified by flash chromatography (Hexane/DCM 5:1 to 1:2) to give 24b (1.733 mg, yield: 79%) as a colourless oil.

$^1$H NMR (CDCl$_3$, 300 MHz) δ: 9.72 (t, 1H, J=2.7 Hz), 7.74-7.67 (m, 4H), 7.48-7.37 (m, 6H), 5.56-5.45 (m, 1H), 5.32-5.23 (m, 1H), 4.29-4.20 (m, 1H), 2.51-2.48 (m, 2H), 2.31-2.27 (m, 2H), 1.43 (dd, 3H, J=6.9, 1.5 Hz), 1.06 (s, 9H).

$^{13}$C-RMN (CDCl$_3$, 75 MHz) δ: 202.3; 136.1; 134.0; 130.1; 127.9; 127.4; 125.1; 69.4; 50.1; 35.1; 27.2; 19.5; 13.1.

Synthesis of Intermediate 25a

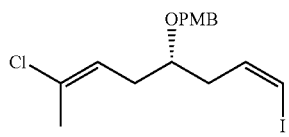

To a suspension of iodomethyltriphenylphosphonium iodide (16.6 g; 31 mmol) in anhydrous THF (126 mL), at room temperature, a 1M solution of NaHMDS in THF (31.27 mL) was slowly added. After stirring for 2 min, the yellow mixture was cooled to −78° C. and a solution of 24a (6.3 g, 22 mmol) in THF (82 mL) was then added. The reaction mixture was stirred at −78° C. for 2 h, and at room temperature for 5 min, diluted with hexane and filtered through a plug of celite. The plug was rinsed with hexane and the combined filtrates were evaporated under reduced pressure and the resulting oil was purified by column chromatography (Hexane/EtOAc 12:1 to 8:1) affording 25a as yellow oil (5.6 g; yield: 62%).

$^1$H NMR (CDCl$_3$, 300 MHz) δ: 7.25 (d, 2H, J=8.7 Hz), 6.85 (d, 2H, J=8.7 Hz), 6.25 (m, 2H) 5.64 (t, 1H, J=7.8 Hz), 4.42 (m, 2H), 3.80 (s, 3H), 3.55 (m, 1H), 2.40 (m, 2H), 2.25 (m, 2H), 2.03 (s, 3H).

Synthesis of Intermediate 25b

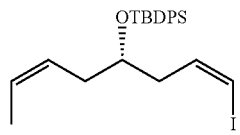

To a suspension of iodomethyltriphenylphosphorane (3.32 g, 6.38 mmol) in THF (60 mL) at room temperature 6.83 mL of a 1M solution of NaHMDS (6.38 mmol) in THF was slowly added. After stirring for 2 min, the yellow mixture was cooled to −78° C. and a solution of 24b (1.67 g, 4.56 mmol) in THF (40 mL) was then added. The reaction mixture was stirred at −78° C. for 90 min, then at room temperature for 5 min, diluted with hexane and filtered through a plug celite/SiO$_2$. The plug was rinsed with Hexane/EtOAc (10:1 to 5:1) to afford compound 25b (2 g, yield: 89%) as a colourless oil that was used without further purification.

$^1$H NMR (CDCl$_3$, 300 MHz) δ: 7.70-7.66 (m, 4H), 7.45-7.34 (m, 6H), 6.21-6.31 (m, 2H), 5.49-5.43 (m, 1H), 5.35-5.27 (m, 1H), 3.94-3.75 (m, 1H), 2.30-2.27 (m, 2H), 2.24-2.04 (m, 2H), 1.43 (d, 3H, J=6.6 Hz), 1.06 (s, 9H).

$^{13}$C-RMN (CDCl$_3$, 75 MHz) δ: 138.2; 136.2; 134.3; 129.9; 127.8; 126.4; 126.0; 84.1; 71.9; 41.6; 34.5; 27.2; 19.6; 13.2.

Synthesis of Intermediate 25c

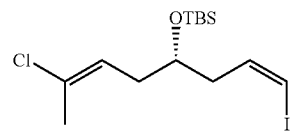 [SMILES: C/C(Cl)=C\C[C@@H](C/C=C\I)O[Si](C)(C)C(C)(C)C]

2,3-Dichloro-5,6-dicyano-p-benzoquinone (DDQ) (3.6 g, 16 mmol) was added to a solution of 25a (5 g; 12 mmol) in DCM-H$_2$O (20:1) under Ar atmosphere at room temperature. After 1:30 h (TLC Hexane/EtOAc 4:1 showed no starting material) the reaction was quenched by pouring into Et$_2$O (200 mL) and washing with 1M NaOH (3×50 mL) and brine (50 mL). The organic phase was dried over Na$_2$SO$_4$, filtered and concentrated. Chromatographic separation of p-methoxybenzaldehyde was facilitated by reduction to p-methoxybenzyl alcohol. Towards this end, a solution of the residue obtained in MeOH with NaBH$_4$ under Ar atmosphere was maintained at room temperature for 1 h. The reaction mixture was then quenched by pouring into Et$_2$O (100 mL) and washing with 1 M HCl (40 mL) and brine (40 mL). The organic phase was dried over Na$_2$SO$_4$, filtered and concentrated. The resulting oil was purified on silica gel (Hexane/EtOAc 10:1 to 4:1) to provide the secondary alcohol as colourless oil. (2.8 g; yield: 80%).

To a solution of secondary alcohol (2.8 g; 10 mmol) in anhydrous DCM, under Ar and at 0° C. 2,6-lutidine was added dropwise, followed by addition of tert-Butyldimethylsilyl trifluoromethanesulfonate (TBSOTf) (TLC Hexane/DCM 4:1 showed no starting material). At this point the crude mixture was quenched with 0.5M HCl (25 mL) and extracted with DCM (2×25 mL). The combined organic layers were washed with a saturated aqueous solution of NaHCO₃ and brine. The organic phase was dried over NaSO₄, filtered and concentrated. Flash chromatography (Hexane/EtOAc 100:1 to 20:1) provided 25c as a colourless oil (3.14 g; yield: 80%).

¹H NMR (CDCl₃, 300 MHz) δ: 6.25 (m, 2H) 5.64 (t, 1H, J=7.8 Hz), 3.82 (m, 1H), 2.38 (t, 2H, J=6.0 Hz), 2.20 (t, 2H, J=6.3 Hz), 2.03 (s, 3H), 0.86 (s, 9H), 0.05 (s, 6H).

¹³C RMN (CDCl₃, 75 MHz) δ: 137.7, 130.9, 124.3, 84.6, 70.6, 42.5, 36.6, 25.9, 21.3, 18.2, −4.4.

Example 7

Synthesis of Fragment BCD

Scheme 4 provides several examples of synthesis of fragment BCD, in accordance with the nomenclature provided in Scheme 1.

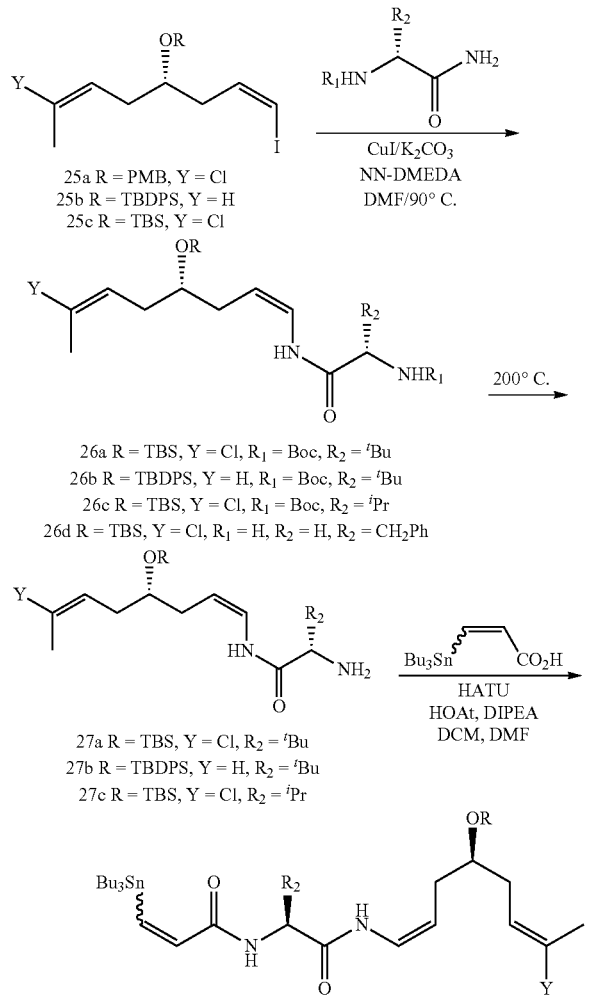

Synthesis of Intermediate 26a

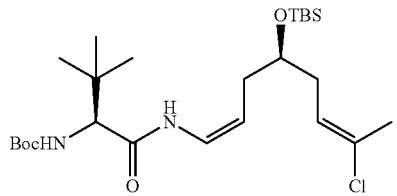 [SMILES: C/C(Cl)=C\C[C@@H](C/C=C\NC(=O)[C@@H](NC(=O)OC(C)(C)C)C(C)(C)C)O[Si](C)(C)C(C)(C)C]

A resealable Schlenk tube was charged with copper (I) iodide (148 mg, 0.78 mmol), potassium carbonate (1.076 g, 7.78 mmol) and Boc-tert-LeuCONH₂ (prepared following the procedure described in Pozdnev, V. F., *Tetrahedron Letters* 1995, 36, 7115-7118) (0.96 g, 4.15 mmol), evacuated and filled with argon. N,N'-Dimethylethylenediamine (DMEDA) (0.166 mL, 1.55 mmol), vinyl iodide 25c (1.04 g, 2.59 mmol) and dry DMF (15 mL) were added under argon. The Schlenk tube was sealed, heated at 90° C. for 16-18 h and cooled to room temperature. The resultant mixture was diluted with EtOAc and quenched with water. The organic layer was washed with water and dried over Na₂SO₄. The solvent was removed under reduced pressure and the residue was purified by flash chromatography on silica gel (Hexane/EtOAc, 20:1 to 15:1). Intermediate 26a (670 mg, yield, 53%) was obtained as an oil.

¹H NMR (CDCl₃, 300 MHz) δ: 7.72 (d, 1H, J=9.9 Hz), 6.70 (t, 1H, J=9.6 Hz), 5.54 (t, 1H, J=7.8 Hz), 5.35 (d, 1H, J=9.0 Hz), 4.76 (q, 1H, J=7.8 Hz), 3.89 (d, 1H, J=9.0 Hz), 3.73-3.68 (m, 1H), 2.12 (m, 4H), 1.98 (s, 3H), 0.971 (s, 9H), 0.84 (s, 9H), 0.02 (s, 3H), 0.01 (s, 3H).

¹³C NMR (CDCl₃, 75 MHz) δ: 168.9, 156.0 131.1, 123.9, 122.6, 108.2, 79.9, 71.6, 62.5, 36.5, 34.8, 33.8, 28.1, 26.7, 25.9, 21.2, 18.3, −4.3, −4.4

Synthesis of Intermediate 26b

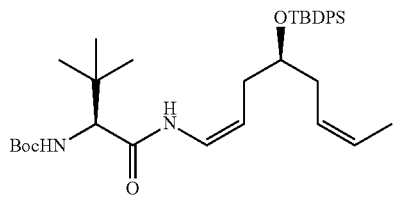

A resealable Schlenk tube was charged with copper (I) iodide (232.4 mg, 1.22 mmol), potassium carbonate (1.688 g, 12.23 mmol) and Boc-tert-LeuCONH₂ (2.474 g, 6.12 mmol), evacuated and filled with argon. N,N-Dimethylethylenediamine (0.26 mL, 2.45 mmol), vinyl iodide 25b (2 g, 4.08 mmol) and dry DMF (35 mL) were added under argon. The Schlenk tube was sealed, heated at 90° C. for 16-18 h and cooled to room temperature. The resultant mixture was diluted with EtOAc and quenched with water. The organic layer was washed with water and dried over Na₂SO₄. The solvent was removed under reduced pressure and the residue was purified by flash chromatography on silica gel (Hexane/EtOAc, 20:1 to 15:1). Intermediate 26b (1.06 g, yield: 44%) was obtained as an oil.

¹H NMR (CDCl₃, 300 MHz) δ: 7.70-7.67 (m, 4H), 7.43-7.35 (m, 6H), 7.13 (d, 1H, J=10.5 Hz), 6.67 (dd, 1H, J=10.2, 9.6 Hz), 5.56-5.45 (m, 1H), 5.36-5.28 (m, 2H), 4.86-4.78 (m,

2H), 3.88-3.77 (m, 1H), 2.26-2.04 (m, 4H), 1.44 (d, 3H, J=6.9 Hz), 1.43 (s, 9H), 1.06 (s, 9H), 0.96 (s, 9H).

Synthesis of Intermediate 26c

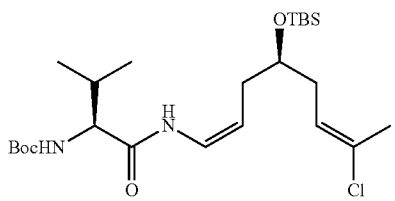 [SMILES: C/C(Cl)=C\C[C@@H](C/C=C\NC(=O)[C@@H](NC(=O)OC(C)(C)C)C(C)C)O[Si](C)(C)C(C)(C)C]

A resealable Schlenk tube was charged with copper (I) iodide (40.4 mg, 0.213 mmol), potassium carbonate (294 mg, 2.13 mmol) and Boc-Val-CONH$_2$ (prepared following the procedure described in Pozdnev, V. F., *Tetrahedron Letters* 1995, 36, 7115-7118) (230 mg, 1.06 mmol), evacuated and filled with argon. N,N-Dimethylethylenediamine (45 μL, 0.426 mmol), vinyl iodide 25c (283 mg, 0.71 mmol) and dry DMF (35 mL) were added under argon. The Schlenk tube was sealed, heated at 90° C. for 16-18 h and cooled to room temperature. The resultant mixture was diluted with EtOAc and quenched with water. The organic layer was washed with water and dried over Na$_2$SO$_4$. The solvent was removed under reduced pressure and the residue was purified by flash chromatography on silica gel (Hexane/EtOAc, 7:1 to 3:1). Intermediate 26c (270 g, yield: 77%) was obtained as an oil.

$^1$H NMR (CDCl$_3$, 300 MHz) δ: 7.80 (d, 1H, J=9.3), 6.79-6.73 (m, 1H), 5.58 (t, 1H, J=7.5 Hz), 5.02 (br s, 1H), 4.85-4.76 (m, 1H), 3.93 (dd, 1H, J=8.4, 6.0 Hz), 3.80-3.73 (m, 1H), 2.12-2.22 (m, 5H), 2.02 (s, 3H), 1.45 (s, 9H), 0.98 (d, 3H, J=6.9 Hz), 0.93 (d, 3H, J=6.9 Hz), 0.89 (s, 9H), 0.07 (s, 3H), 0.06 (s, 3H).

$^{13}$C NMR (CDCl$_3$, 75 MHz) δ: 169.3, 131.1, 124.0, 122.7, 108.9, 71.6, 36.5, 33.8, 30.6, 28.5, 26.1, 21.3, 19.6, 18.3, 17.9, −4.3, −4.4.

Synthesis of Intermediate 26d

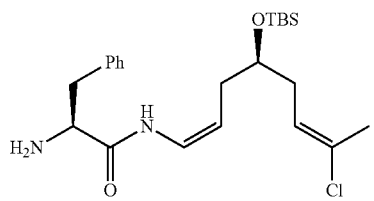 [SMILES: C/C(Cl)=C\C[C@@H](C/C=C\NC(=O)[C@@H](N)Cc1ccccc1)O[Si](C)(C)C(C)(C)C]

A resealable Schlenk tube was charged with copper (I) iodide (14.2 mg, 0.075 mmol), potassium carbonate (104 mg, 0.75 mmol) and Fmoc-Phe-CONH$_2$ (prepared following the procedure described in Pozdnev, V. F., *Tetrahedron Letters* 1995, 36, 7115-7118) (145 mg, 0.375 mmol), evacuated and filled with argon. N,N'-Dimethylethylenediamine (16 μL, 0.15 mmol) vinyl iodide 25c (100 mg, 0.25 mmol) and dry DMF (2.5 mL) were added under argon. The Schlenk tube was sealed, heated at 90° C. for 16-18 h and cooled to room temperature. The resultant mixture was diluted with EtOAc and quenched with water. The organic layer was washed with water and dried over Na$_2$SO$_4$. The solvent was removed under reduced pressure and the residue was purified by flash chromatography on silica gel (Hexane/EtOAc, 4:1 to 1:1). Intermediate 26d (46 mg, yield: 42%) was obtained as an oil.

1H NMR (CDCl$_3$, 300 MHz) δ: 9.19 (d, 1H, J=11.1 Hz), 7.36-7.21 (m, 5H), 6.77 (ddd, 1H, J=10.2, 9.3, 0.9), 5.60 (br t, 1H, J=7.8 Hz), 4.82-4.78 m, 1H), 3.79-3.71 (m, 1H), 3.67 (dd, 1H, J=9.6, 3.9 Hz), 3.32 (dd, 1H, J=13.8, 3.9 Hz), 2.69 (dd, 1H, J=13.8, 9.6 Hz), 2.20-2.11 (m, 4H), 1.99 (s, 3H), 0.89 (s, 9H), 0.05 (s, 3H), 0.04 (s, 3H).

13C NMR (CDCl$_3$, 75 MHz) δ: 171.9, 137.9, 130.9, 129.5, 129.1, 127.2, 124.1, 122.5, 107.9, 71.4, 56.6, 40.9, 36.3, 33.6, 26.1, 21.3, 18.3, −4.4, −4.5.

MS (ES) m/z 437.1 [M+H]$^+$, 459.0 [M+Na]$^+$

Synthesis of Intermediate 27a

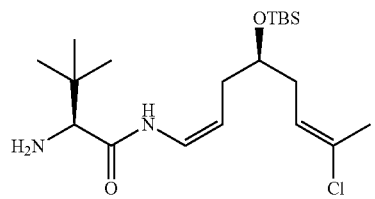

A solution of amino protected derivative 26a (670 mg, 1.33 mmol) in ethylene-glycol (30 mL) was heated at 200° C. for 10-20 min. The reaction mixture was then cooled at room temperature, diluted with DCM, quenched with brine and poured into water. A few drops of 3M NaOH were added until the solution reached pH 14 and then was extracted thoroughly with DCM. The combined organic phases were dried over Na$_2$SO$_4$, filtrated and concentrated in vacuo to afford the primary amine 27a (510 mg, yield: 95%) as a yellow oil which was used without further purification.

$^1$H NMR (CDCl$_3$, 300 MHz) δ: 8.77 (d, 1H, J=9.9 Hz), 6.71 (t, 1H, J=9.6 Hz), 5.56 (t, 1H, J=7.8 Hz), 4.71 (m, 1H), 3.72 (m, 1H), 3.14 (s, 1H), 2.14 (m, 4H), 1.97 (s, 3H), 0.97 (s, 9H), 0.84 (s, 9H), 0.02 (s, 6H).

$^{13}$C RMN (CDCl$_3$, 75 MHz) δ: 171.2, 131.0, 124.1, 122.5, 107.1, 71.5, 64.3, 36.2, 34.5, 33.8, 26.5, 26.0, 21.2, 18.2, −4.4, −4.5.

Synthesis of Intermediate 27b

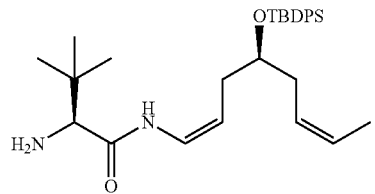

A solution of amino protected derivative 26b (847 mg, 1.43 mmol) in ethylene-glycol (50 mL) was heated at 200° C. for 10-20 min. The reaction mixture was then cooled at room temperature, diluted with DCM, quenched with brine and poured into water. A few drops of 3M NaOH were added until the solution reached pH 14 and then was extracted thoroughly with DCM. The combined organic phases were dried over Na$_2$SO$_4$, filtrated and concentrated in vacuo to afford the primary amine 27b (435 mg, 62%) as a white foam after purification by flash chromatography (Hexane/EtOAc 10:1 to 1:2).

¹H NMR (CDCl₃, 300 MHz) δ: 8.50 (d, 1H, J=10.8 Hz), 7.70-7.66 (m, 4H), 7.45-7.33 (m, 6H), 6.67 (dd, 1H, J=11.1, 9.3 Hz), 5.48-5.40 (m, 1H), 5.36-5.28 (m, 1H), 4.79 (dd, 1H, J=16.2, 7.5 Hz), 3.87-3.79 (m, 1H), 3.08 (s, 1H), 2.22-2.14 (m, 4H), 1.43 (d, 3H, J=6.9 Hz), 1.05 (s, 9H), 0.97 (s, 9H).

¹³C-RMN (CDCl3, 75 MHz) δ: 171.0; 136.1; 134.5; 129.8; 127.8; 126.3; 126.2; 122.1; 107.6; 72.6; 64.4; 34.0; 34.4; 32.8; 27.2; 26.9; 19.6; 13.2.

Synthesis of Intermediate 27c

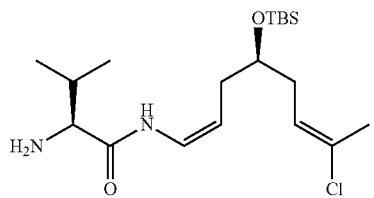 [SMILES: C/C(Cl)=C\C[C@@H](C/C=C\NC(=O)[C@@H](N)C(C)C)O[Si](C)(C)C(C)(C)C]

A solution of amino protected derivative 26c (255 mg, 0.52 mmol) in ethylene-glycol (15 mL) was heated at 200° C. for 10-20 min. The reaction mixture was then cooled at room temperature, diluted with DCM, quenched with brine and poured into water. A few drops of 3M NaOH were added until the solution reached pH 14 and then was extracted thoroughly with DCM. The combined organic phases were dried over Na₂SO₄, filtrated and concentrated in vacuo to afford the primary amine 27c (170 mg, 85%) as a yellow oil which was used without further purification.

¹H NMR (CDCl₃, 300 MHz) δ: 9.27 (d, 1H, J=10.2), 6.76 (dd, 1H, J=11.1, 9.6 Hz), 5.61 (t, 1H, J=7.8 Hz), 4.80-4.72 (m, 1H), 3.81-3.73 (m, 1H), 3.31 (d, 1H, J=3.6 Hz) 2.44-2.33 (m, 1H), 2.20-2.16 (m, 4H), 2.03 (s, 3H), 1.59 (br s, 2H), 1.00 (d, 3H, J=6.9 Hz), 0.89 (s, 9H), 0.82 (d, 3H, J=6.9 Hz), 0.05 (s, 6H).

¹³C NMR (CDCl₃, 75 MHz) δ: 172.1, 131.1, 124.1, 122.5, 107.4, 71.5, 36.5, 33.7, 30.8, 26.0, 21.3, 20.0, 16.1, −4.3, −4.4.

Synthesis of Intermediate 28a

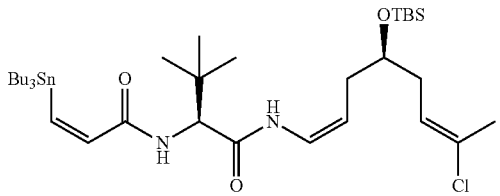

To a solution of amine 27a (918 mg, 2.27 mmol) in DCM/DMF (10:1, 39.6 mL), a solution of (Z)-3-tributylstannylpropenoic acid (1028 mg, 2.84 mmol) in dry DCM was added, under argon atmosphere, and then was cooled at 0° C. Diisopropylethylamine (DIPEA) (0.6 mL, 3.4 mmol), 1-Hydroxy-7-azabenzotriazole (HOAt) (310 mg, 2.27 mmol), and N,N,N',N'-Tetramethyl-O-(7-azabenzotriazol-1-yl)uronium hexafluorophosphate (HATU) (860 mg, 2.27 mmol) were added to the solution and after 30 min the cold bath was removed. The reaction mixture was stirred at room temperature for 2 h, quenched with a saturated aqueous solution of NH₄Cl, poured into water and extracted with DCM. The combined organic phases were dried over Na₂SO₄, filtered and concentrated. The residue was purified by flash chromatography (Hexane/EtOAc 20:1 to 15:1) to give amide 28a (1110 mg; yield: 66%) as an oil.

¹H NMR (CDCl₃, 300 MHz) δ: 7.63 (d, 1H, J=10.5 Hz), 6.97 (d, 1H, J=12.3 Hz), 6.75 (d, 1H, J=12.3 Hz), 6.72 (t, 1H, J=9.5 Hz), 6.50 (d, 1H, J=9.0 Hz), 5.56 (t, 1H, J=6.6 Hz), 4.83 (q, 1H, J=9.0 Hz), 4.41 (d, 1H, J=9.6 Hz) 3.76 (m, 1H), 2.17 (m, 4H), 2.01 (s, 3H), 1.45 (m, 6H), 1.25 (m, 8H), 1.0 (s, 9H), 0.88 (s, 9H), 0.84 (m, 13H), 0.06 (s, 6H).

Synthesis of Intermediate 28b

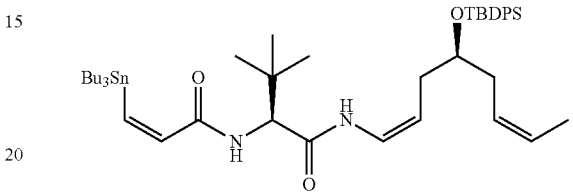

To a solution of amine 27b (575 mg, 1.17 mmol) in DCM/DMF (4:1, 12.5 mL), a solution of (Z)-3-tributylstannylpropenoic acid (505.6 mg, 1.4 mmol) in dry DCM was added, under argon atmosphere, and then was cooled at 0° C. DIPEA (0.243 mL, 1.76 mol), 7-hydroxybenzotriazole (HOBt) (189.2 mg, 1.4 mmol), and HATU (532.28 mg, 1.4 mmol) were added to the solution and after 30 min the cold bath was removed. The reaction mixture was stirred at room temperature for 2 h, quenched with a saturated aqueous solution of NH₄Cl, poured into water and extracted with DCM. The combined organic phases were dried over Na₂SO₄, filtered and concentrated. The residue was purified by flash chromatography (Hexane/EtOAc 20:1 to 15:1) to give amide 28b (780.4 mg; yield: 77%) as a white foam.

¹H NMR (CDCl₃, 300 MHz) δ: 7.70-7.68 (m, 4H), 7.43-7.36 (m, 6H), 7.02 (d, 1H, J=12.3 Hz), 7.00 (d, 1H, J=10.8 Hz), 6.75 (d, 1H, J=12.3 Hz), 6.66 (t, 1H, J=9.3 Hz), 6.26 (d, 1H, J=9.6 Hz), 5.57-5.34 (m, 1H), 5.38-5.28 (m, 1H), 4.83 (dd, 1H, J=16.5, 7.8 Hz), 4.31 (d, 1H, J=9.6 Hz), 3.89-3.82 (m, 1H), 2.26-2.02 (m, 4H), 1.50-1.42 (m, 6H), 1.43 (d, 3H, J=6.9 Hz), 1.33-1.20 (m, 6H), 1.06 (s, 9H), 0.96 (s, 9H), 0.95-0.83 (m, 15H).

¹³C-RMN (CDCl₃, 75 MHz) δ: 168.0; 166.2; 153.8; 136.3; 136.1; 134.3; 130.0; 127.8; 126.7; 126.0; 121.6; 109.0; 72.6; 60.7; 35.7; 34.0; 32.7; 29.5; 27.7; 27.2; 26.7; 19.5; 14.0; 13.2; 11.8.

Synthesis of Intermediate 28c

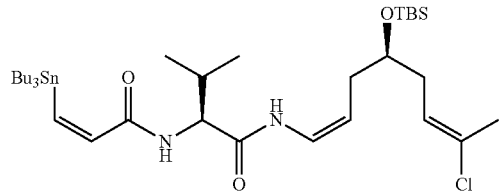

To a solution of amine 27c (170 mg, 0.437 mmol) in DCM/DMF (10:1, 7.7 mL), a solution of (Z)-3-tributylstannylpropenoic acid (197.2 mg, 0.546 mmol) in dry DCM was added, under argon atmosphere, and then was cooled at 0° C. DIPEA (0.11 mL, 0.655 mmol), HOAt (59.4 mg, 0.437 mmol), and HATU (166 mg, 0.437 mmol) were added to the solution and after 30 min the cold bath was removed. The reaction mixture was stirred at room temperature for 2 h, quenched with a saturated aqueous solution of NH$_4$Cl, poured into water and extracted with DCM. The combined organic phases were dried over Na$_2$SO$_4$, filtered and concentrated. The residue was purified by flash chromatography (Hexane/EtOAc 20:1 to 15:1) to give amide 28c (250 mg, yield: 78%) as a white foam.

$^1$H NMR (CDCl$_3$, 300 MHz) δ: 7.94 (d, 1H, J=10.8 Hz), 7.00 (d, 1H, J=12.3 Hz), 6.75 (d, 1H, J=12.3 Hz), 6.72 (t, 1H, J=9.5 Hz), 6.50 (d, 1H, J=9.0 Hz), 5.56 (t, J=6.6 Hz, 1H), 4.83 (q, 1H, J=9.0 Hz), 4.41 (t, 1H, J=9.0 Hz), 3.76 (m, 1H), 2.17 (m, 4H), 2.01 (s, 3H), 1.45 (m, 7H), 1.25 (m, 8H), 0.88 (s, 9H), 0.84 (m, 19H), 0.06 (s, 6H).

$^{13}$C-RMN (CDCl$_3$, 75 MHz) δ: 169.2, 166.8, 153.8, 136.2, 131.1, 123.9, 122.6, 108.7, 71.6, 59.2, 36.5, 33.7, 31.4, 29.5, 29.4, 27.6, 26.1, 21.3, 19.5, 18.5, 18.3, 14.0, 11.8, −4.3, −4.4.

Synthesis of Intermediate 28d

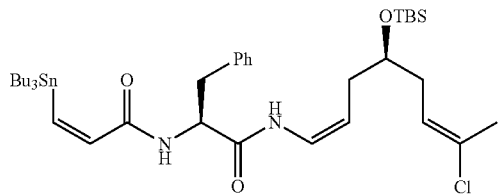

To a solution of amine 26d (44 mg, 0.1 mmol) in DCM/DMF (10:1, 1.3 mL), a solution of (Z)-3-tributylstannylpropenoic acid (45 mg, 0.125 mmol) in dry DCM was added, under argon atmosphere, and then was cooled at 0° C. DIPEA (26 μL, 0.15 mmol), HOAt (13.6 mg, 0.1 mmol), and HATU (38 mg, 0.1 mmol) were added to the solution and after 30 min the cold bath was removed. The reaction mixture was stirred at room temperature for 2 h, quenched with a saturated aqueous solution of NH$_4$Cl, poured into water and extracted with DCM. The combined organic phases were dried over Na$_2$SO$_4$, filtered and concentrated. The residue was purified by flash chromatography (Hexane/EtOAc 20:1 to 15:1) to give amide 28d (60 mg, yield: 80%) as an oil.

$^1$H NMR (CDCl$_3$, 300 MHz) δ: 7.43 (d, 1H, J=10.8 Hz), 7.34-7.22 (m, 5H), 7.02 (d, 1H, J=12.3 Hz), 6.70 (d, 1H, J=12.3 Hz), 6.66 (dd, 1H, J=9.9, 9.3 Hz), 6.34 (d, 1H, J=7.8 Hz), 5.51 (dd, 1H, J=8.1, 7.5 Hz), 4.81-4.71 (m, 2H), 3.68-3.59 (m, 1H), 3.18 (dd, 1H, J=13.5, 6 Hz), 2.69 (dd, 1H, J=13.5, 8.4 Hz), 2.11-2.04 (m, 2H), 2.01 (s, 3H), 1.96-1.87 (m, 1H), 1.80-1.70 (m, 1H), 1.53-1.43 (m, 8H), 1.31-1.24 (m, 10H), 0.89-0.85 (m, 9H), 0.88 (s, 9H), 0.04 (s, 3H), 0.01 (s, 3H).

$^{13}$C NMR (CDCl$_3$, 75 MHz) δ: 168.5, 166.5, 154.4, 136.7, 135.9, 131.0, 129.5, 129.1, 127.4, 124.0, 122.3, 108.8, 71.5, 55.1, 38.8, 36.6, 33.3, 29.5, 29.4, 27.6, 26.0, 21.3, 18.2, 14.0, 11.8, −4.3, −4.5.

MS (ES) m/z 781.2 [M+H]$^+$, 803.2 [M+Na]$^+$

Synthesis of Intermediate 28e

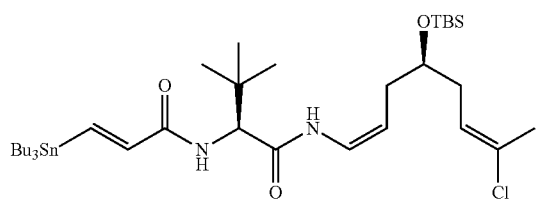

To a solution of amine 27a (30 mg, 0.075 mmol) in DCM/DMF (10:1, 1 mL), a solution of (E)-3-tributylstannylpropenoic acid (33.5 mg, 0.095 mmol) in dry DCM was added, under argon atmosphere, and then was cooled at 0° C. DIPEA (19 μL, 0.11 mol), HOAt (10 mg, 0.075 mmol), and HATU (27.5 mg, 0.075 mmol) were added to the solution and after 30 min the cold bath was removed. The reaction mixture was stirred at room temperature for 2 h, quenched with a saturated aqueous solution of NH$_4$Cl, poured into water and extracted with DCM. The combined organic phases were dried over Na$_2$SO$_4$, filtered and concentrated. The residue was purified by flash chromatography (Hexane/EtOAc 6:1) to give amide 28e (25 mg, yield: 45%) as an oil.

$^1$H NMR (CDCl$_3$, 300 MHz) δ: 7.68 (d, 1H, J=9.2 Hz), 7.52 (d, 1H, J=18.9 Hz), 6.73 (t, 1H, J=9.2 Hz), 6.28 (d, 1H, J=10.8 Hz), 6.25 (d, 1H, J=18.9 Hz), 5.60 (t, 1H, J=7.2 Hz), 4.83 (q, 1H, J=9.2 Hz), 4.40 (d, 1H, J=9.6 Hz), 3.77 (m, 1H), 2.17 (m, 4H), 2.01 (s, 3H), 1.45 (m, 6H), 1.25 (m, 8H), 1.0 (s, 9H), 0.88 (s, 9H), 0.84 (m, 13H), 0.06 (s, 6H).

Example 8

Scheme 5 provides the synthesis of several compounds of the invention.

Scheme 5

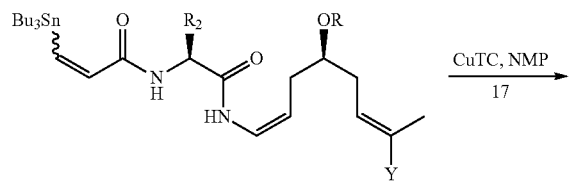

(Z)-28a R = TBS, Y = Cl, R$_2$ = $^t$Bu
(Z)-28b R = TBDPS, Y = H, R$_2$ = $^t$Bu
(Z)-28c R = TBS, Y = Cl, R$_2$ = $^i$Pr
(Z)-28d R = TBS, Y = Cl, R$_2$ = CH$_2$Ph
(E)-28e R = TBS, Y = Cl, R$_2$ = $^t$Bu

-continued

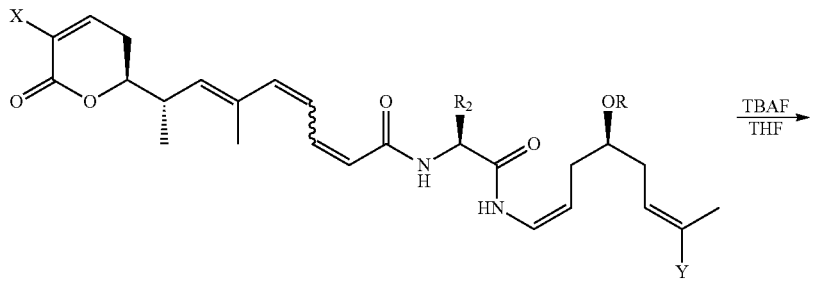

(7E,9Z,11Z)-29a R = TBS, R$_2$ = $^t$Bu, X = OMe, Y = Cl
(7E,9Z,11Z)-29b R = TBDPS, R$_2$ = $^t$Bu, X = OMe, Y = H
(7E,9Z,11Z)-29c R = TBS, R$_2$ = $^i$Pr, X = OMe, Y = Cl
(7E,9Z,11Z)-29d R = TBS, R$_2$ = CH$_2$Ph, X = OMe, Y = Cl
(7E,9Z,11E)-29e R = TBS, R$_2$ = $^t$Bu, X = OMe, Y = Cl
(7E,9Z,11Z)-29f R = TBS, R$_2$ = $^t$Bu, X = H, Y = Cl

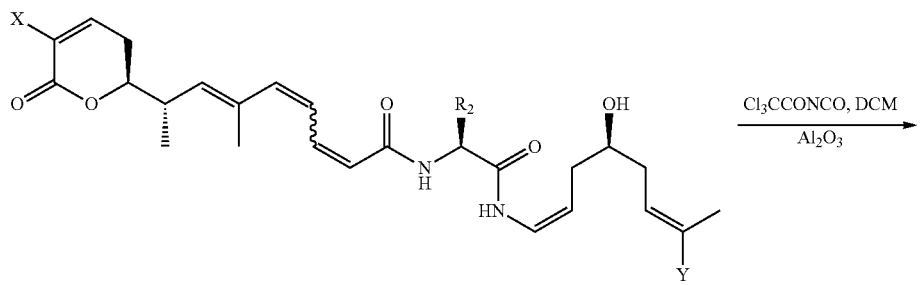

(7E,9Z,11Z)-30a R$_2$ = $^t$Bu, X = OMe, Y = Cl
(7E,9Z,11Z)-30b R$_2$ = $^t$Bu, X = OMe, Y = H
(7E,9Z,11Z)-30c R$_2$ = $^i$Pr, X = OMe, Y = Cl
(7E,9Z,11Z)-30d R$_2$ = CH$_2$Ph, X = OMe, Y = Cl
(7E,9Z,11E)-30e R$_2$ = $^t$Bu, X = OMe, Y = Cl
(7E,9Z,11Z)-30f R$_2$ = $^t$Bu, X = H, Y = Cl

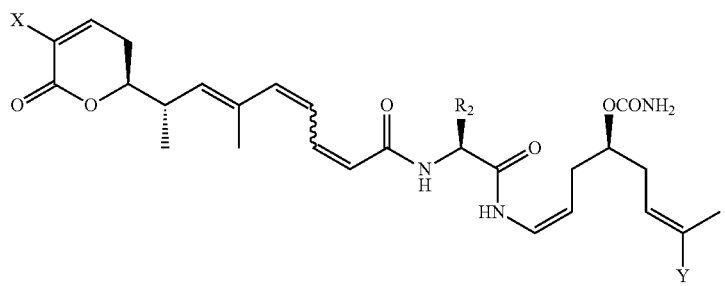

(7E,9Z,11Z)-Compound 1 R$_2$ = $^t$Bu, X = OMe, Y = Cl
(7E,9Z,11Z)-Compound 4 R$_2$ = $^t$Bu, X = OMe, Y = H
(7E,9Z,11Z)-Compound 5 R$_2$ = $^i$Pr, X = OMe, Y = Cl
(7E,9Z,11Z)-Compound 31 R$_2$ = CH$_2$Ph, X = OMe, Y = Cl
(7E,9Z,11Z)-Compound 8 R$_2$ = $^t$Bu, X = OMe, Y = Cl

Synthesis of Compound 29a

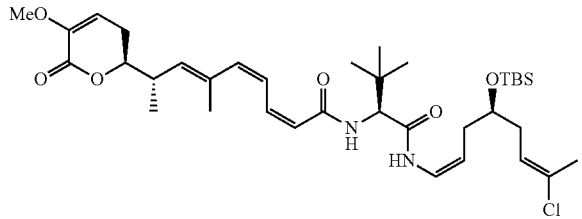 [SMILES: COC1=CC[C@@H]([C@@H](C)/C=C(C)/C=C\C=C/C(=O)N[C@H](C(=O)N/C=C\C[C@H](C/C=C(\C)Cl)O[Si](C)(C)C(C)(C)C)C(C)(C)C)OC1=O]

To a solution of alkenylstannane 28a (1.1 g, 1.47 mmol) and 17a (0.62 g, 1.77 mmol in 1-methyl-2-pyrrolidinone (NMP) (14.7 mL) at 0° C., Copper thiophenecarboxylate (CuTC) (422 mg, 2.2 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×15 mL). The organic solution was dried and evaporated to give the crude product which was purified by column chromatography (Hexane/EtOAc 5:1 to 1:1) to give triene 29a (0.66 g, yield: 66%) as an oil.

$^1$H NMR (CDCl$_3$, 300 MHz) δ: 7.89 (d, 1H, J=10.8 Hz), 7.22 (dd, 1H, J=12.3, 11.4 Hz), 6.86 (dd, 1H, J=11.7, 11.4 Hz), 6.70 (dd, 1H, J=9.9, 9.3 Hz), 6.35 (d, 1H, J=9.3 Hz), 6.13 (d, 1H, J=11.4 Hz), 5.66 (d, 1H, J=11.4 Hz), 5.60 (dd, 1H, J=5.4, 3.9 Hz), 5.55 (br t, 1H, J=7.8 Hz), 5.26 (d, 1H, J=10.2 Hz), 4.84-4.76 (m, 1H), 4.3 (d, 1H, J=9.3 Hz), 4.20-4.16 (m, 1H), 3.77-3.69 (m, 1H), 3.63 (s, 3H), 2.89-2.77 (m, 1H), 2.41-2.33 (m, 2H), 2.19-2.13 (m, 4H), 2.00 (s, 3H), 1.82 (s, 3H), 1.13 (d, 3H, J=6.9 Hz), 1.02 (s, 9H), 0.86 (s, 9H), 0.4 (s, 3H), 0.03 (s, 3H).

$^{13}$C-RMN (CDCl$_3$, 75 MHz) δ: 168.5; 166.4; 161.8; 145.4; 140.3; 137.3; 134.4; 134.3; 131.0; 124.3; 124.1; 122.4; 121.2; 108.7; 108.4; 82.0; 71.6; 60.6; 55.6; 37.5; 36.5; 35.1; 33.8; 26.5; 26.0; 21.3; 18.3; 17.4; 16.9; −4.3; −4.4.

Synthesis of Compound 29b

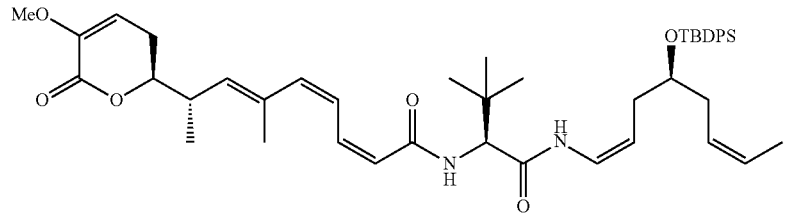

To a solution of alkenylstannane 28b (780.4 mg, 0.904 mmol) and 17a (377.4 mg, 1.085 mmol) in NMP (9 mL) at 0° C., Copper thiophenecarboxylate (258.5 mg, 1.36 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×10 mL). The organic solution was dried and evaporated to give the crude product which was purified by column chromatography (Hexane/EtOAc 5:1 to 1:1) to give triene 29b (459.7 mg, yield: 66%) as an oil.

$^1$H NMR (CDCl$_3$, 300 MHz) δ: 7.66-7.64 (m, 4H), 7.43-7.32 (m, 7H), 7.23 (t, 1H, J=11.7 Hz), 6.85 (t, 1H, J=11.7 Hz), 6.62 (dd, 1H, J=10.5, 9.3 Hz), 6.41 (d, 1H, J=9.3 Hz), 6.11 (d, 1H, J=11.7 Hz), 5.66 (d, 1H, J=11.4 Hz), 5.60 (dd, 1H, J=5.7, 5.1 Hz), 5.49-5.41 (m, 1H), 5.32-5.27 (m, 1H), 5.25 (d, 1H, J=9.9 Hz), 4.83-4.75 (m, 1H), 4.32 (d, 1H, J=9.3 Hz), 4.22-4.15 (m, 1H), 3.83-3.78 (m, 1H), 3.62 (s, 3H), 2.86-2.78 (m, 1H), 2.40-2.35 (m, 2H), 2.20-2.04 (m, 4H), 1.81 (s, 3H), 1.40 (d, 3H, J=6.9 Hz), 1.13 (d, 3H, J=6.9 Hz), 1.03 (s, 9H), 0.97 (s, 9H).

$^{13}$C-RMN (CDCl$_3$, 75 MHz) δ: 168.3; 166.3; 161.8; 145.4; 140.2, 137.3; 136.1; 134.8; 134.4; 134.3; 129.9; 127.8; 126.4; 126.1; 124.4; 121.7; 121.2; 108.4; 109.1; 82.0; 72.6; 60.6; 55.6; 37.5; 35.2; 32.7; 31.1; 27.2; 26.8, 26.5; 19.5; 17.4; 16.9; 13.1.

Synthesis of Compound 29c

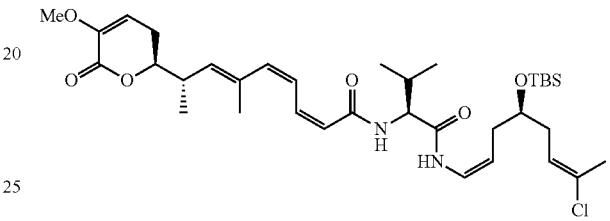

To a solution of alkenylstannane 28c (250 mg, 0.34 mmol) and 17a (142 mg, 0.409 mmol) in NMP (2.5 mL) at 0° C., Copper thiophenecarboxylate (97 mg, 0.51 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×10 mL). The organic solution was dried and evaporated to give the crude product which was purified by column chromatography (Hexane/EtOAc 10:1 to 6:1) to give triene 29c (150 mg, yield: 67%) as an oil.

$^1$H NMR (CDCl$_3$, 300 MHz) δ: 8.21 (d, 1H, J=10.8 Hz), 7.28 (t, 1H, J=11.7 Hz), 6.88 (dd, 1H, J=11.7, 11.4 Hz), 6.72 (dd, 1H, J=10.2, 9.3 Hz), 6.42 (d, 1H, J=8.4 Hz), 6.15 (d, 1H, J=11.7 Hz), 5.66 (d, 1H, J=11.4 Hz), 5.61 (dd, 1H, J=5.7, 3.6 Hz), 5.56 (br t, 1H, J=8.1 Hz), 5.27 (d, 1H, J=9.9 Hz), 4.85-4.77 (m, 1H), 4.30 (dd, 1H, J=8.1, 7.5 Hz), 4.24-4.16 (m, 1H), 3.79-3.72 (m, 1H), 3.66 (s, 3H), 2.88-2.80 (m, 1H), 2.42-2.37 (m, 2H), 2.18-2.14 (m, 5H), 2.00 (s, 3H), 1.83 (s, 3H), 1.14 (d, 3H J=6.9 Hz), 0.97 (d, 3H, J=6.6 Hz), 0.96 (d, 3H, J=6.6 Hz), 0.86 (s, 9H), 0.4 (s, 6H).

$^{13}$C-RMN (CDCl$_3$, 75 MHz) δ: 169.2 166.8; 161.8; 145.4; 140.5, 137.7; 134.6; 134.3; 131.0, 124.3; 124.2, 122.6; 121.2; 108.6; 108.4; 82.0; 71.5; 58.9; 55.6; 37.5; 36.4; 33.8; 30.8, 26.5; 26.1; 21.3, 19.6, 18.5, 18.3, 17.4, 16.9, −4.3, −4.4.

Synthesis of Compound 29d

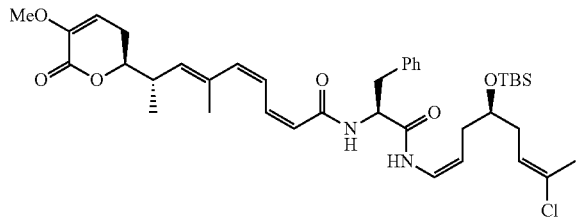 [SMILES: COC1=CC[C@@H]([C@@H](C)/C=C(C)/C=C\C=C/C(=O)N[C@@H](Cc2ccccc2)C(=O)N/C=C\C[C@H](C/C=C(\C)Cl)O[Si](C)(C)C(C)(C)C)OC1=O]

To a solution of alkenylstannane 28d (60 mg, 0.08 mmol) and 17a (32.4 mg, 0.09 mmol) in NMP (1 mL) at 0° C., Copper thiophenecarboxylate (22 mg, 0.12 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×10 mL). The organic solution was dried and evaporated to give the crude product which was purified by column chromatography (Hexane/EtOAc 4:1 to 1:1) to give triene 29d (13 mg, yield: 25%) as an oil.

$^1$H NMR (CDCl$_3$, 300 MHz) δ: 7.59 (d, 1H, J=11.1 Hz), 7.33-7.24 (m, 5H), 7.23 (t, 1H, J=11.7 Hz), 6.90 (dd, 1H, J=11.7, 11.4 Hz), 6.66 (dd, 1H, J=10.5, 9 Hz), 6.24 (d, 1H, J=7.2 Hz), 6.17 (d, 1H, J=12.0 Hz), 5.63-5.58 (m, 2H), 5.51 (td, 1H, J=7.8, 1.2 Hz), 5.28 (d, 1H, J=10.8 Hz), 4.79-4.67 (m, 2H), 4.24-4.17 (m, 1H), 3.66 (s, 3H), 3.65-3.62 (m, 1H), 3.22 (dd, 1H, J=13.5, 6.3 Hz), 3.04 (dd, 1H, J=13.8, 8.4 Hz), 2.89-2.81 (m, 1H), 2.43-2.37 (m, 2H), 2.11-2.04 (m, 2H), 2.00 (s, 3H), 1.84 (s, 3H), 1.93-1.72 (m, 2H), 1.16 (d, 3H, J=6.9 Hz), 0.86 (s, 9H), 0.03 (s, 3H), 0.01 (s, 3H).

$^{13}$C NMR (CDCl$_3$, 75 MHz) δ: 168.4, 166.5, 161.7, 145.5, 140.8, 138.1, 136.8, 134.5, 134.3, 131.0, 129.5, 129.1, 127.4, 124.2, 124.1, 122.3, 120.4, 108.7, 108.3, 82.0, 71.4, 55.7, 54.9, 38.3, 37.5, 36.6, 33.4, 26.5, 26.0, 21.3, 18.2, 17.4, 16.9, −4.3, −4.4.

MS (ES) m/z 711.2 [M+H]$^+$

Synthesis of Compound 29e

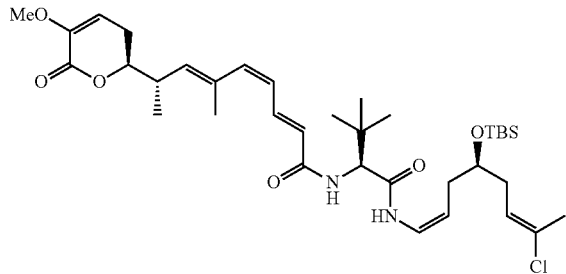 [SMILES: COC1=CC[C@@H]([C@@H](C)/C=C(C)/C=C\C=C\C(=O)N[C@H](C(=O)N/C=C\C[C@H](C/C=C(\C)Cl)O[Si](C)(C)C(C)(C)C)C(C)(C)C)OC1=O]

To a solution of alkenylstannane 28e (50 mg, 0.067 mmol) and 17a (28 mg, 0.08 mmol) in NMP (1 mL) at 0° C., Copper thiophenecarboxylate (19.1 mg, 0.10 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×10 mL). The organic solution was dried and evaporated to give the crude product which was purified by column chromatography (Hexane/EtOAc 5:1 to 1:1) to give triene 29e (33 mg, yield: 50%) as an oil.

$^1$H NMR (CDCl$_3$, 300 MHz) δ: 7.73 (d, 1H, J=11.4 Hz), 7.70 (dd, 1H, J=14.1, 11.7 Hz), 6.71 (dd, 1H J=9.9, 9.7 Hz), 6.30 (d, 1H, J=9.3 Hz), 6.13 (d, 1H, J=12.9 Hz), 6.04 (dd, 1H, J=11.7, 11.4 Hz), 5.93 (d, 1H, J=15.0 Hz), 5.63 (br t, 1H, J=4.5 Hz), 5.58-5.53 (m, 1H), 5.34 (d, 1H, J=9.9 Hz), 4.85-4.78 (m, 1H), 4.41 (d, 1H, J=9.3), 4.24-4.16 (m, 1H), 3.77-3.72 (m, 1H), 3.64 (s, 3H), 2.90-2.78 (m, 1H), 2.45-2.41 (m, 2H), 2.19-2.12 (m, 4H), 2.01 (s, 3H), 1.91 (s, 3H), 1.16 (d, 3H, J=6.6 Hz), 1.02 (s, 9H), 0.87 (s, 9H), 0.06 (s, 3H), 0.04 (s, 3H).

$^{13}$C NMR (CDCl$_3$, 75 MHz) δ: 168.5, 166.1, 161.8, 145.4, 140.7, 138.0, 135.3, 134.9, 131.1, 125.8, 124.9, 124.0, 122.4, 108.7, 108.5, 81.9, 71.6, 60.9, 55.6, 37.6, 36.5, 35.2, 33.8, 29.9, 26.8, 26.1, 21.3, 18.3, 17.3, 16.9, −4.3, −4.4.

Synthesis of Compound 29f

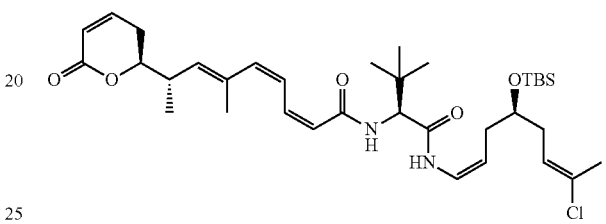

To a solution of alkenylstannane 28a (60 mg, 0.083 mmol) and 17b (29 mg, 0.09 mmol) in NMP (0.9 mL) at 0° C., Copper thiophenecarboxylate (24 mg, 0.12 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.5N (3×10 mL). The organic solution was dried and evaporated to give the crude product which was purified by column chromatography (Hexane/EtOAc 5:1 to 1:1) to give amide 29f (27 mg, yield: 50%) as an oil.

$^1$H NMR (CDCl$_3$, 300 MHz) δ: 7.62 (d, 1H, J=10.5 Hz), 7.25 (dd, 1H, J=12.6, 11.4 Hz), 6.94-6.84 (m, 2H), 6.73 (dd, 1H, J=10.5, 9.0 Hz), 6.23 (d, 1H, J=9.3 Hz), 6.17 (d, 1H, J=11.4 Hz), 6.06-6.01 (m, 1H), 5.66 (d, 1H, J=11.4 Hz), 5.60-5.55 (m, 1H), 5.29 (d, 1H, J=9.9 Hz), 4.88-4.80 (m, 1H), 4.34 (d, 1H, J=9.3 Hz), 4.27-4.19 (m, 1H), 3.79-3.72 (m, 1H), 2.90-2.81 (m, 1H), 2.36-2.30 (m, 2H), 2.21-2.13 (m, 4H), 2.03 (s, 3H), 1.85 (s, 3H), 1.17 (d, 3H, J=6.6 Hz), 1.03 (s, 9H), 0.89 (s, 9H), 0.08 (s, 3H), 0.06 (s, 3H).

Synthesis of Compound 30a

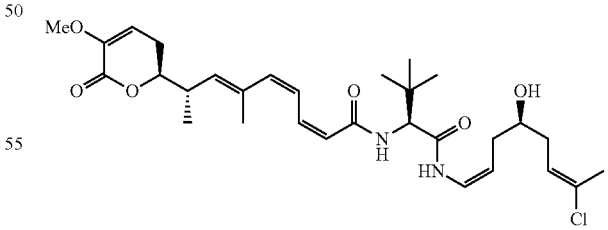

To a solution of 29a (275 mg, 0.41 mmol) in THF (6 mL) under N$_2$ and at room temperature, TBAF 1M in THF (0.82 mL, 0.82 mmol) was added. The reaction was stirred at room temperature for 18 hours and then quenched with a saturated aqueous solution of NH$_4$Cl and extracted with EtOAc. The combined organic phases were dried over Na$_2$SO$_4$, filtered and concentrated. The residue was purified by flash chromatography (Hexane/EtOAc 3:1 to 1:2) to give alcohol 30a (175 mg; yield: 76%) as a white solid.

¹H NMR (CDCl₃, 300 MHz) δ: 9.00 (d, 1H, J=10.2 Hz), 7.25 (dd, 1H, J=12.0, 11.4 Hz), 6.86 (dd, 1H, J=11.7, 11.4 Hz), 6.72 (dd, 1H, J=9.6, 8.7 Hz), 6.68 (d, 1H, J=8.7 Hz), 6.13 (d, 1H, J=11.7 Hz), 5.68 (d, 1H, J=11.4 Hz), 5.63-5.58 (m, 2H), 5.27 (d, 1H, J=10.2 Hz), 4.85-4.76 (m, 1H), 4.42 (d, 1H, J=9.3 Hz), 4.25-4.17 (m, 1H), 3.70-3.69 (m, 1H), 3.63 (s, 3H), 3.48 (br s, 1H), 2.89-2.75 (m, 1H), 2.42-2.36 (m, 2H), 2.22-2.11 (m, 4H), 2.04 (s, 3H), 1.82 (s, 3H), 1.14 (d, 3H, J=6.6 Hz), 1.03 (s, 9H).

The isomer (21S)- of Compound 30a was obtained when the synthetic process was performed starting from racemic fragment D. The final mixture of isomers [(21S)-Compound 30a and (21R)-Compound 30a] was separated by semi-preparative reversed phase HPLC (SymmetryPrep C18 7 μm, 7.8×150 mm, gradient H₂O:MeCN from 50 to 60% MeCN in 30 min, UV detection, flow 2.5 mL/min, [rt ((21S)-30a): 15.4 min, rt ((21R)-30a):14.7 min]) and (21S)-Compound 30a was obtained in pure form:

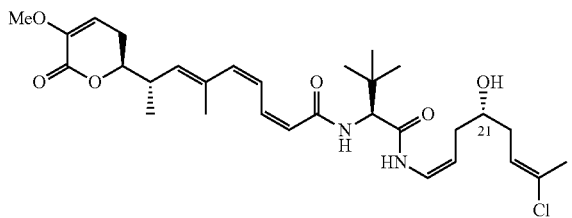 [SMILES: COC1=CC[C@@H]([C@@H](C)/C=C(C)/C=C\C=C/C(=O)N[C@H](C(=O)N/C=C\C[C@H](O)C/C=C(\C)Cl)C(C)(C)C)OC1=O]

¹H NMR (CDCl₃, 300 MHz) δ: 8.62 (d, 1H, J=10.2 Hz), 7.28-22 (m, 1H), 6.93-6.86 (m, 1H), 6.81-6.75 (m, 1H), 6.32 (d, 1H, J=9.0 Hz), 6.17 (d, 1H, J=11.7 Hz), 5.68-5.58 (m, 3H), 5.28 (d, 1H, J=10.2 Hz), 4.93-4.84 (m, 1H), 4.32 (d, 1H, J=9.3 Hz), 4.25-4.17 (m, 1H), 3.78-3.67 (m, 1H), 3.66 (s, 3H), 2.89-2.81 (m, 1H), 2.43-2.38 (m, 2H), 2.28-2.20 (m, 4H), 2.08 (s, 3H), 1.84 (s, 3H), 1.16 (d, 3H J=6.9 Hz), 1.02 (s, 9H).

Synthesis of Compound 30b

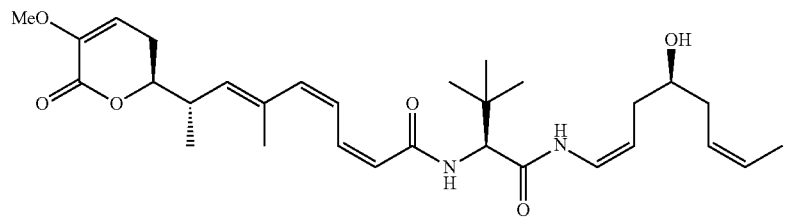 [SMILES: C/C=C\C[C@H](O)C/C=C\NC(=O)[C@@H](NC(=O)\C=C/C=C\C(C)=C\[C@H](C)[C@@H]1CC=C(OC)C(=O)O1)C(C)(C)C]

To a solution of 29b (586 mg, 0.76 mmol) in THF (7.5 mL) under N₂ and at room temperature, TBAF 1M in THF (1.53 mL, 2 mmol) was added. The reaction was stirred at room temperature for 18 hours and then quenched with a saturated aqueous solution of NH₄Cl and extracted with EtOAc. The combined organic phases were dried over Na₂SO₄, filtered and concentrated. The residue was purified by flash chromatography (Hexane/EtOAc 3:1 to 1:2) to give alcohol 30b (320 mg, yield: 80%) as a white solid.

¹H NMR (CDCl₃, 300 MHz) δ: 8.95 (d, 1H, J=10.2 Hz), 7.25 (t, 1H, J=12.0 Hz), 6.85 (t, 1H, J=11.7 Hz), 6.73 (t, 1H, J=9.6 Hz), 6.57 (d, 1H, J=8.7 Hz), 6.12 (d, 1H, J=11.4 Hz), 5.67 (d, 1H, J=11.4 Hz), 5.61 (dd, 1H, J=5.4, 3.9 Hz), 5.63-5.58 (m, 1H), 5.44-5.35 (m, 1H), 5.26 (d, 1H, J=9.9 Hz), 4.86 (q, 1H, J=8.1 Hz), 4.38 (d, 1H, J=9.3 Hz), 4.24-4.16 (m, 1H), 3.81-3.71 (m, 1H), 3.64 (s, 3H), 2.96-2.92 (m, 1H), 2.86-2.79 (m, 1H), 2.41-2.37 (m, 2H), 2.28-2.14 (m, 4H), 1.82 (s, 3H), 1.61 (d, 3H, J=6.6 Hz), 1.14 (d, 3H, J=6.6 Hz), 1.02 (s, 9H).

¹³C-RMN (CDCl₃, 75 MHz) δ: 168.7; 166.6; 161.8; 145.4; 140.3; 137.5; 134.4; 134.3; 127.7; 126.0; 124.4; 123.7; 121.1; 108.9; 108.4; 82.0; 72.1; 60.9; 55.7; 37.6; 35.0; 34.8; 33.2; 26.9; 26.5; 17.4; 16.9; 13.3.

Synthesis of Compound 30c

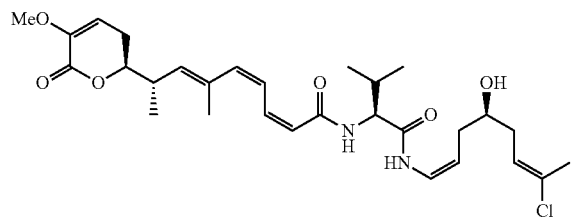 [SMILES: COC1=CC[C@@H]([C@@H](C)/C=C(C)/C=C\C=C/C(=O)N[C@H](C(=O)N/C=C\C[C@@H](O)C/C=C(\C)Cl)C(C)C)OC1=O]

To a solution of 29c (150 mg, 0.23 mmol) in THF (4.8 mL) under N₂ and at room temperature, TBAF 1M in THF (0.45 mL, 0.45 mmol) was added. The reaction was stirred at room temperature for 18 hours and then quenched with saturated aqueous solution of NH₄Cl and extracted with EtOAc. The combined organic phases were dried over Na₂SO₄, filtered and concentrated. The residue was purified by flash chromatography (Hexane/EtOAc 3:1 to 1:2) to give alcohol 30c (90 mg, yield: 73%) as a white solid.

¹H NMR (CDCl₃, 300 MHz) δ: 9.16 (d, 1H, J=10.2 Hz), 7.26 (dd, 1H, J=12.0, 11.1 Hz), 6.87 (dd, 1H, J=11.7, 11.4 Hz), 6.79-6.70 (m, 2H), 6.14 (d, 1H, J=11.7 Hz), 5.68 (d, 1H, J=11.7 Hz), 5.63-5.58 (m, 2H), 5.27 (d, 1H, J=9.6 Hz), 4.85-4.76 (m, 1H), 4.35 (dd, 1H, J=8.4, 7.5 Hz), 4.24-4.17 (m, 1H), 3.70-3.69 (m, 1H), 3.63 (s, 3H), 3.43 (br s, 1H), 2.89-2.76 (m, 1H), 2.42-2.36 (m, 2H), 2.21-2.14 (m, 4H), 2.03 (s, 3H), 1.82 (s, 3H), 1.13 (d, 3H J=6.9 Hz), 0.96 (d, 6H, J=6.6 Hz).

¹³C-RMN (CDCl₃, 75 MHz) δ: 169.7, 167.1, 161.8, 145.4, 140.5, 137.8, 134.6, 134.2, 131.6, 124.4, 123.9, 123.8, 120.7, 108.5, 108.4, 82.0, 59.1, 55.7, 37.5, 36.4, 33.5, 31.0, 26.5, 21.3, 19.5, 18.7, 17.4, 16.8.

MS (ES) m/z 549.0 [M+H]⁺, 571.1 [M+Na]⁺

Synthesis of Compound 30d

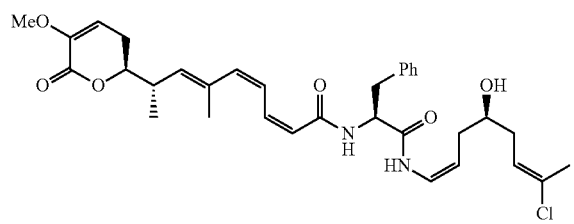 [SMILES: COC1=CC[C@@H]([C@@H](C)/C=C(C)/C=C\C=C/C(=O)N[C@@H](Cc2ccccc2)C(=O)N/C=C\C[C@@H](O)C/C=C(\C)Cl)OC1=O]

To a solution of 29d (11 mg, 0.02 mmol) in THF (0.32 mL) under N₂ and at room temperature, TBAF 1M in THF (0.03 mL, 0.03 mmol) was added. The reaction was stirred at room temperature for 18 hours and then quenched with saturated aqueous solution of NH₄Cl and extracted with EtOAc. The combined organic phases were dried over Na$_2$SO$_4$, filtered and concentrated. The residue was purified by flash chromatography (Hexane/EtOAc 3:1 to 1:2) to give alcohol 30d (6 mg, yield: 65%) as a white solid.

$^1$H NMR (CDCl$_3$, 300 MHz) δ: 8.54 (d, 1H, J=9.9 Hz), 7.34-7.23 (m, 5H), 7.20 (t, 1H, J=11.7 Hz), 6.89 (dd, 1H, J=11.7, 11.4 Hz), 6.72 (dd, 1H, J=9.9, 9.3 Hz), 6.27 (d, 1H, J=8.1 Hz), 6.17 (d, 1H, J=11.7 Hz), 5.63-5.53 (m, 3H), 5.28 (d, 1H, J=10.2 Hz), 4.84-4.76 (m, 1H), 4.75-4.68 (m, 1H), 4.25-4.17 (m, 1H), 3.66 (s, 3H), 3.67-3.65 (m, 1H), 3.18 (dd, 1H, J=13.8, 6.3 Hz), 3.06 (dd, 1H, J=13.8, 8.1 Hz), 2.89-2.81 (m, 1H), 2.43-2.38 (m, 2H), 2.15-2.10 (m, 3H), 2.06 (s, 3H), 1.92-1.87 (m, 1H), 1.84 (s, 3H), 1.16 (d, 3H, J=6.6 Hz).

$^{13}$C NMR (CDCl$_3$, 75 MHz) δ: 168.6, 166.6, 160.8, 145.8, 140.8, 138.1, 136.8, 134.6, 134.2, 129.6, 129.0, 127.2, 124.1, 124.0, 123.4, 120.4, 108.3, 108.2, 82.0, 71.6, 55.7, 55.0, 38.4, 37.5, 36.4, 33.0, 26.5, 21.3, 17.4, 16.9.

MS (ES) m/z 597.2 [M+H]$^+$.

Synthesis of Compound 30e

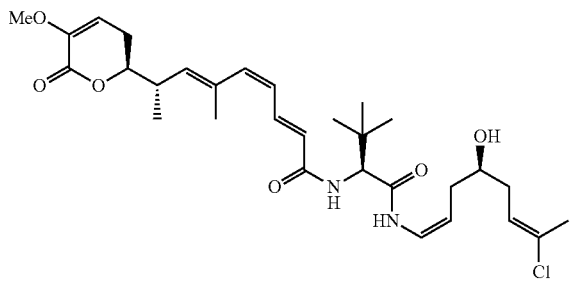 [SMILES: COC1=CC[C@@H]([C@@H](C)/C=C(C)/C=C\C=C\C(=O)N[C@H](C(=O)N/C=C\C[C@@H](O)C/C=C(\C)Cl)C(C)(C)C)OC1=O]

To a solution of 29e (32 mg, 0.047 mmol) in THF (1 mL) under N$_2$ and at room temperature, TBAF 1M in THF (0.094 mL, 0.094 mmol) was added. The reaction was stirred at room temperature for 18 hours and then quenched with saturated aqueous solution of NH$_4$Cl and extracted with EtOAc. The combined organic phases were dried over Na$_2$SO$_4$, filtered and concentrated. The residue was purified by flash chromatography (Hexane/EtOAc 3:1 to 1:2) to give alcohol 30e (14 mg, yield: 55%) as a white foam.

$^1$H NMR (CDCl$_3$, 500 MHz) δ: 8.97 (d, 1H, J=10.2 Hz), 7.71 (dd, 1H J=14.7, 11.7 Hz), 6.74 (dd, 1H J=9.3, 9.9 Hz), 6.57 (d, 1H, J=9.0 Hz), 6.15 (d, 1H, J=11.7 Hz), 6.03 (dd, 1H, J=11.7, 11.4 Hz), 5.95 (d, 1H, J=14.7 Hz), 5.65-5.58 (m, 2H), 5.35 (d, 1H, J=9.9 Hz), 4.87-4.78 (m, 1H), 4.42 (d, 1H, J=9.3), 4.25-4.18 (m, 1H), 3.72-3.68 (m, 1H), 3.65 (s, 3H), 3.25 (br s, 1H), 2.87-2.79 (m, 1H), 2.45-2.40 (m, 2H), 2.23-2.12 (m, 4H), 2.04 (s, 3H), 1.89 (s, 3H), 1.15 (d, 3H, J=6.6 Hz). 1.03 (s, 9H).

$^{13}$C NMR (CDCl$_3$, 75 MHz) δ: 168.8, 166.5, 161.68, 145.3, 140.9, 138.2, 135.4, 134.7, 132.0, 125.68, 124.6, 123.9, 123.6, 108.6, 108.4, 81.9, 71.7, 61.3, 55.7, 37.5, 36.5, 36.3, 34.9, 33.3, 26.9, 26.7, 21.3, 17.0, 16.7.

MS (ES) m/z 563.3 [M+H]$^+$, 585.2 [M+Na]$^+$

Synthesis of Compound 30f

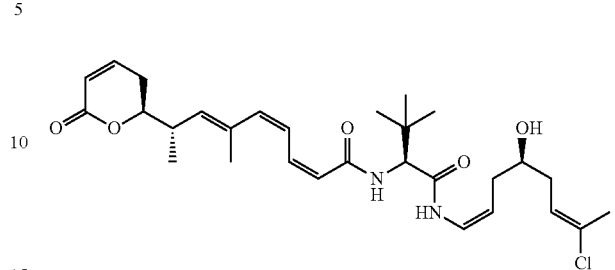

To a solution of 29f (28 mg, 0.04 mmol) in THF (1 mL) under N$_2$ and at room temperature, TBAF 1M in THF (0.09 mL, 0.09 mmol) was added. The reaction was stirred at room temperature for 18 hours and then quenched with saturated aqueous solution of NH$_4$Cl and extracted with EtOAc. The combined organic phases were dried over Na$_2$SO$_4$, filtered and concentrated. The residue was purified by flash chromatography (Hexane/EtOAc 3:1 to 1:2) to give alcohol 30f (17 mg; yield: 75%) as a white solid.

$^1$H NMR (CDCl$_3$, 300 MHz) δ: 9.05 (d, 1H, J=10.2 Hz), 7.35 (m, 2H), 7.0 (dd, 1H, J=11.7, 11.4 Hz), 6.73 (dd, 1H, J=9.6, 8.7 Hz), 6.56 (d, 1H, J=8.7 Hz), 6.05 (m, 3H), 5.63-5.58 (m, 2H), 5.30 (d, 1H, J=10.2 Hz), 4.78 (m, 1H), 4.50 (d, 1H, J=9.3 Hz), 3.68 (m, 1H), 3.48 (br s, 1H), 2.45 (m, 1H), 2.42-2.36 (m, 2H), 2.22-2.11 (m, 4H), 2.04 (s, 3H), 1.82 (s, 3H), 1.14 (d, 3H J=6.6 Hz), 1.03 (s, 9H).

Synthesis of Compound 1

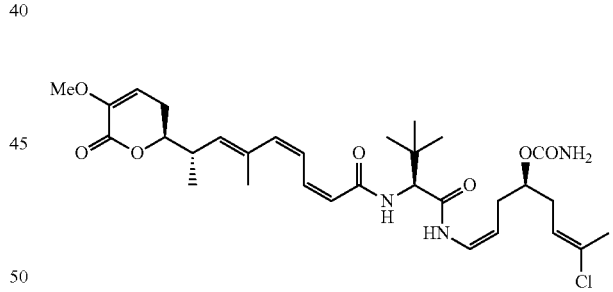

To a solution of 30a (300 mg, 0.53 mmol) in Dichloromethane (7.5 mL) at 0° C., trichloroacetyl isocyanate (TCAI) (76 μl, 0.64 mmol) was added. The reaction was stirred at 0° C. for 30 min and then neutral aluminium oxide was added. The mixture was stirred for 5-30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 2:1 to 1:2). Compound 1 (0.26 g, yield: 81%) was obtained as a white solid and exhibited physical and spectroscopic characteristics ($^1$H, $^{13}$C RMN and MS) equivalent to those reported in Example 2.

The isomer (21S)- of Compound 1 was obtained by either of these two methods:
A.—following the same procedure starting from the mixture of isomers (21R)- and (21S)-Compound 30a and final separation of (21S)-Compound 1 by semipreparative reversed phase HPLC (SymmetryPrep C18 7 μm, 7.8×150 mm, gradient H$_2$O:MeOH from 50 to 100% MeOH in 30 min, UV detection, flow 2.5 mL/min, [rt ((21S)-1): 19.2 min, rt ((21R)-1): 19.8 min]).
B.—following the same procedure as disclose for compound 1, but starting from pure (21S)-Compound 30a.

(21S)-Compound 1

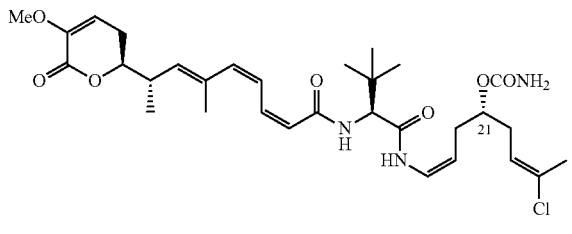

$^1$H NMR (CDCl$_3$, 500 MHz) δ: 8.69 (d, 1H, J=10.5 Hz), 7.30 (t, 1H, J=11.5 Hz), 6.90 (t, 1H, J=11.5 Hz), 6.86-6.82 (m, 1H), 6.34 (d, 1H, J=9.0 Hz), 6.17 (d, 1H, J=11.5 Hz), 5.66 (d, 1H, J=11.5 Hz), 5.64-5.62 (m, 1H), 5.59-5.56 (m, 1H), 5.29 (d, 1H, J=9.5 Hz), 4.81-4.77 (m, 1H), 4.50-4.45 (m, 1H), 4.42 (d, 1H, J=9.5 Hz), 4.25-4.20 (m, 1H), 3.66 (s, 3H), 2.89-2.81 (m, 1H), 2.44-2.31 (m, 5H), 2.24-2.17 (m, 1H), 2.06 (s, 3H), 1.84 (s, 3H), 1.16 (d, 3H, J=6.5 Hz), 1.04 (s, 9H).

$^{13}$C-RMN (125 MHz, CDCl$_3$) δ: 168.4, 166.1, 157.2, 148.3, 145.2, 140.2, 137.4, 134.1, 134.0, 132.0, 124.7, 124.2, 122.4, 120.7, 108.1, 104.7, 81.8, 75.0, 60.8, 55.4, 37.2, 34.8, 32.5, 30.3, 26.7, 26.2, 21.0, 17.1, 16.6.

Synthesis of Compound 4

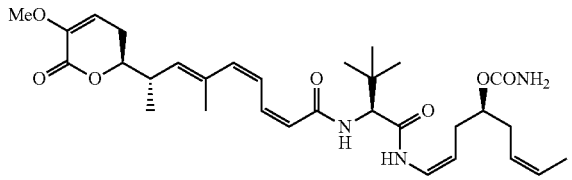

To a solution of 30b (56 mg, 0.105 mmol) in Dichloromethane (1 mL) at 0° C., trichloroacetyl isocyanate (15 μL, 0.126 mmol) was added. The reaction was stirred at 0° C. for 30 min and then neutral aluminium oxide was added. The mixture was stirred for 5-30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 3:1 to 1:2). Compound 4 (57.6 mg, yield: 96%) was obtained as a white foam and exhibited physical and spectroscopic characteristics ($^1$H, $^{13}$C RMN and MS) equivalent to those reported in Example 3.

Synthesis of Compound 5

MeO

OCONH$_2$

Cl

To a solution of 30c (115 mg, 0.21 mmol) in Dichloromethane (2 mL) at 0° C., trichloroacetyl isocyanate (27 μl, 0.23 mmol) was added. The reaction was stirred at 0° C. for 30 min and then neutral aluminium oxide was added. The mixture was stirred for 5-30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 3:1 to 1:2). Compound 5 (71 mg, yield: 57%) was obtained as a white foam and exhibited physical and spectroscopic characteristics ($^1$H, $^{13}$C RMN and MS) equivalent to those reported in Example 3.

The final mixture of isomers (15 mg) was separated by semipreparative reversed phase HPLC (SymmetryPrep C18 7 μm, 7.8×150 mm, gradient H$_2$O:MeOH from 50 to 70% MeOH in 75 min, UV detection, flow 2.5 mL/min, [rt ((15R)-7): 18.15 min, rt ((15S)-7]): 19.62 min) and it was obtained 3.1 mg of pure (15R)-Compound 7 and 2.9 mg of pure (15S)-Compound 7:

The isomer (21S)- of Compound 5 was isolated when 5 was purified by semipreparative reversed phase HPLC (SymmetryPrep C8, gradient H$_2$O:MeCN from 45 to 50% MeCN in 30 min, UV detection, flow 4.7 mL/min, [rt ((21S)-5):21.6 min, rt ((21R)-5): 23.6 min). Starting from a sample (50 mg) which was containing both isomers, after the above mentioned separation it was obtained 39 mg of pure (21R)-Compound 5 and 6.1 mg of pure (21S)-Compound 5.

(21S)-Compound 5

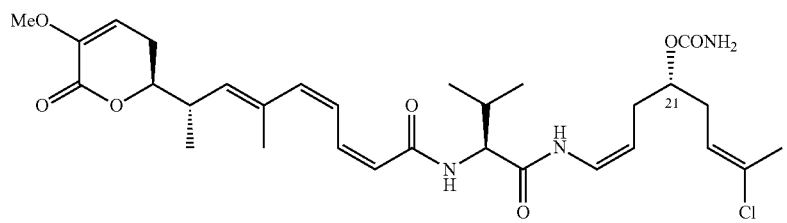

1H NMR (CDCl$_3$, 500 MHz) δ: 8.74 (d, 1H, J=10.5 Hz), 7.29 (dd, 1H, J=11.7, 11.4 Hz), 6.94 (dd, 1H, J=11.7, 11.4 Hz), 6.84 (dd, 1H, J=10.5, 9.3 Hz), 6.22 (m, 2H), 5.68 (d, 1H, J=11.5 Hz), 5.63 (m, 2H), 5.42 (d, 1H, J=9.3 Hz), 4.81 (m, 1H), 4.52 (m, 1H), 4.41 (m, 1H), 4.23 (m, 1H), 3.66 (s, 3H), 2.91 (m, 1H), 2.49-2.38 (m, 3H), 2.35-2.31 (m, 2H), 2.24-2.17 (m, 2H), 2.05 (s, 3H), 1.82 (s, 3H), 1.15 (d, 3H J=6.6 Hz), 0.99 (d, 3H, J=6.9 Hz) 0.96 (d, 3H, J=6.9 Hz).

MS (ES) m/z 592.3 [M+H]$^+$

Synthesis of Compound 31

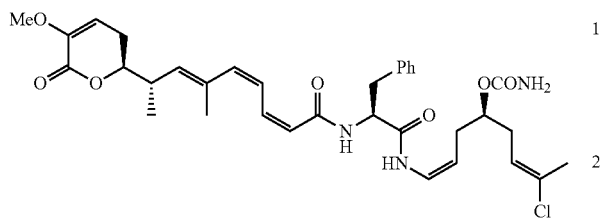

To a solution of 30d (5 mg, 0.008 mmol) in Dichloromethane (0.7 mL) at 0° C., trichloroacetyl isocyanate (1.1 µl, 0.009 mmol) was added. The reaction was stirred at 0° C. for 30 min and then neutral aluminium oxide was added. The mixture was stirred for 5-30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 3:1 to 1:2). Compound 31 (3.5 mg, yield: 66%) was obtained as a white solid $^1$H NMR (CDCl$_3$, 300 MHz) δ: 8.43 (d, 1H, J=10.5 Hz), 7.29-7.19 (m, 6H,), 6.91 (dd, 1H, J=11.7, 11.4 Hz), 6.77 (br dd, 1H, J=10.2, 9.6 Hz), 6.51 (d, 1H, J=8.1 Hz), 6.16 (d, 1H, J=11.4 Hz), 5.69-5.63 (m, 2H), 5.59-5.54 (m, 1H), 5.31 (d, 1H, J=9.3 Hz), 5.12 (br s, 1H,), 4.91-4.84 (m, 1H), 4.76-4.70 (m, 1H), 4.31-4.13 (m, 2H, CH-5), 3.66 (s, 3H), 3.20 (dd, 1H, J=13.5, 6.9 Hz), 3.09 (dd, 1H, J=13.5, 6.6 Hz), 2.89-2.81 (m, 1H), 2.48-2.35 (m, 2H), 2.28-2.23 (m, 3H), 2.05 (s, 3H), 2.01-1.90 (m, 1H), 1.81 (s, 3H), 1.15 (d, 3H, J=6.6 Hz).

$^{13}$C NMR (CDCl$_3$, 75 MHz) δ: 168.9, 166.5, 161.9, 157.1, 145.4, 140.6, 137.9, 136.4, 134.4, 133.9, 132.1, 129.7, 128.8, 127.2, 124.6, 124.6, 122.7, 120.7, 108.5, 105.6, 82.1, 74.8, 55.7, 54.6, 38.7, 37.2, 33.1, 30.5, 26.2, 21.2, 17.3, 16.4.

Synthesis of Compound 8

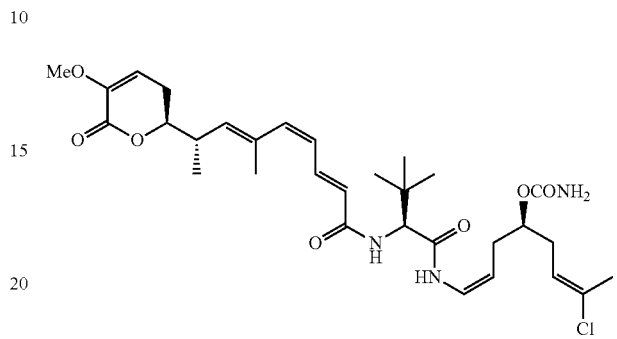

To a solution of 30e (13 mg, 0.023 mmol) in Dichloromethane (1.7 mL) at 0° C., trichloroacetyl isocyanate (3 µl, 0.025 mmol) was added. The reaction was stirred at 0° C. for 30 min and then neutral aluminium oxide was added. The mixture was stirred for 5-30 min and then was soaked into a pad of aluminium oxide. The product was washed out using a mixture of DCM/MeOH 50:1. The filtrate was evaporated in vacuo to to give the crude product which was purified by column chromatography (Hexane/EtOAc 3:1 to 1:2). Compound 8 (14.3 mg, yield: 100%) was obtained as a white solid and exhibited physical and spectroscopic characteristics ($^1$H, $^{13}$C RMN and MS) equivalent to those reported in Example 4.

Example 9

Scheme 6 depicts a synthetic process for several compounds of the invention.

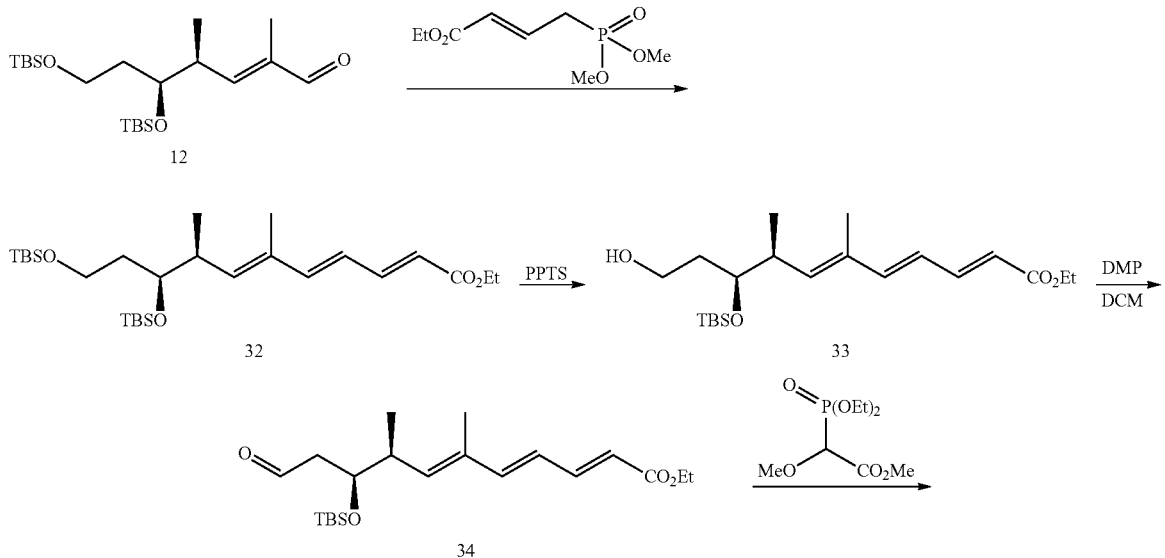

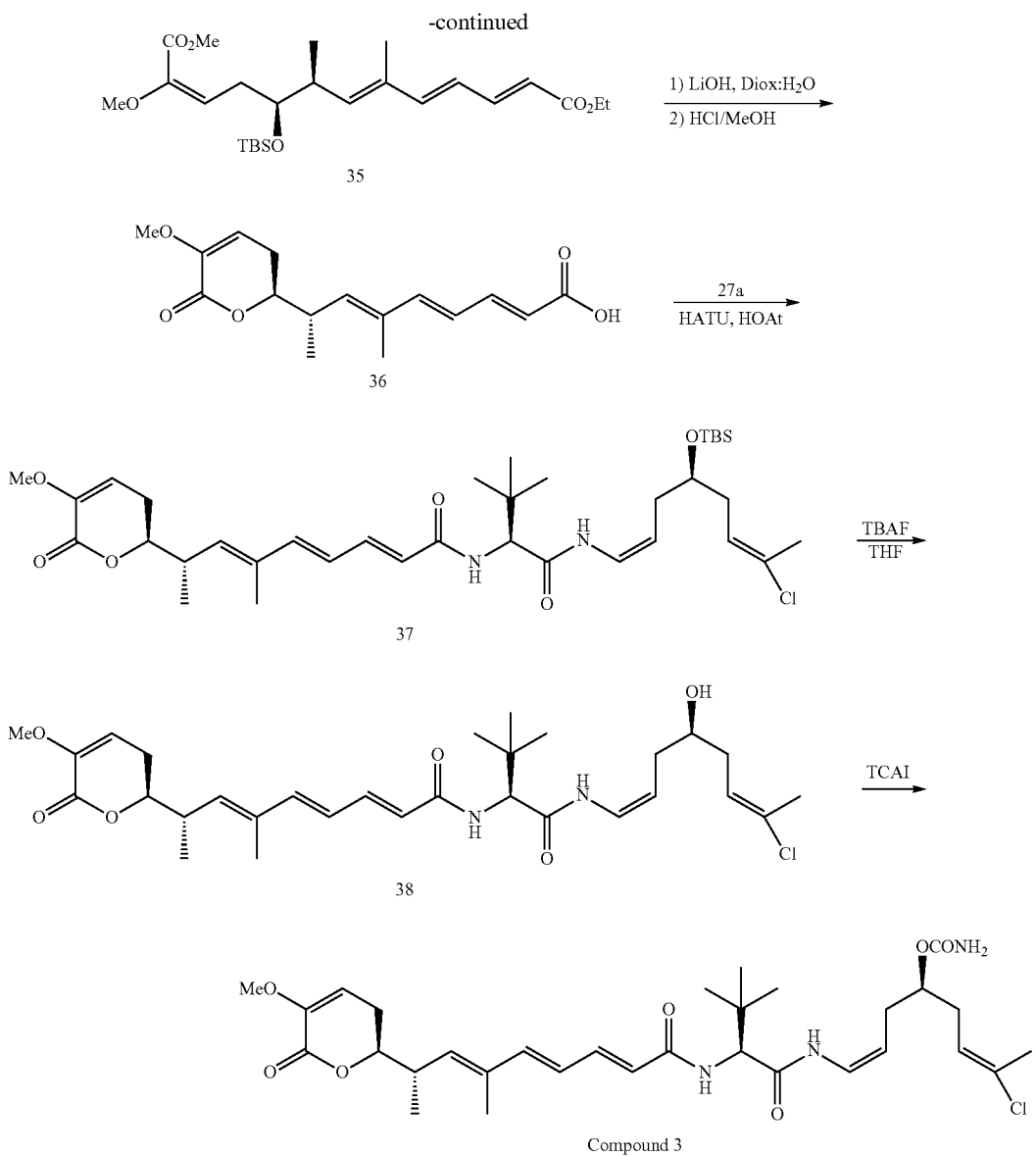

Compound 3

Synthesis of Intermediate 32

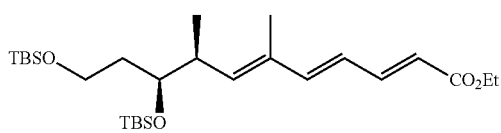 [SMILES: CCOC(=O)/C=C/C=C/C(C)=C/[C@H](C)[C@H](CCO[Si](C)(C)C(C)(C)C)O[Si](C)(C)C(C)(C)C]

To a solution of triethyl 4-phosphonocrotonate (3.7 g, 14.66 mmol) and 18-crown-6 (6.2 g, 23.46 mmol) in dry THF (59 mL) stirred under argon atmosphere at −78° C. KHMDS (28.1 ml, 14.07 mmol) was added dropwise. After 15 min aldehyde 12 (2.35 g, 5.86 mmol) was added dropwise and stirred for 20 hours at room temperature. Then, the reaction was quenched with saturated NH$_4$Cl solution (200 mL), and diluted with EtOAc. The organic phase was dried (Na$_2$SO$_4$) and evaporated at reduced pressure. Purification by column chromatography (Hexane/EtOAc 20:1 to 10:1) afforded 2.7 g (yield: 93%) of triene 32.

$^1$H-RMN (300 MHz, CDCl$_3$) δ: 7.31 (dd, 1H, J=11.2, 15.3 Hz), 6.53 (d, 1H, J=15.0 Hz), 6.21 (dd, 1H, J=11.7, 13.8 Hz), 5.84 (d, 1H, J=15.1 Hz), 5.61 (d, 1H, J=9.6 Hz), 4.17 (m, 2H), 3.72 (m, 1H), 3.63 (m, 2H), 2.61 (m, 1H), 1.78 (s, 3H), 1.67 (m, 2H), 1.26 (m, 3H), 0.94 (d, 3H, J=6.7 Hz), 0.87 (s, 18H), 0.01 (m, 12H).

Synthesis of Intermediate 33

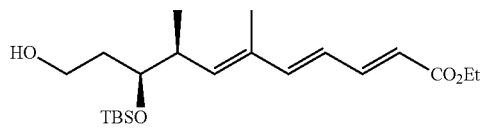 [SMILES: CCOC(=O)/C=C/C=C/C(C)=C/[C@H](C)[C@H](CCO)O[Si](C)(C)C(C)(C)C]

To a solution of 32 (3.75 g, 7.54 mmol) in EtOH (38 mL), pyridinium p-toluenesulfonate (663 mg, 2.64 mmol) was added. The reaction mixture was stirred at room temperature for 17 hours. Then the solvent was removed under reduced pressure and the resulting oil was purified by column chromatography (Hexane/EtOAc 4:1 to 1:1) affording 2.11 g (yield: 73%) of alcohol 33.

$^1$H-RMN (300 MHz, CDCl$_3$) δ: 7.31 (dd, 1H, J=10.8, 15.0 Hz), 6.52 (d, 1H, J=15.3 Hz), 6.23 (dd, 1H, J=11.1, 15.0 Hz), 5.86 (d, 1H, J=15.3 Hz), 5.52 (d, 1H, J=9.9 Hz), 4.18 (q, 2H, J=7.5 Hz), 3.72 (m, 3H), 2.73 (m, 1H), 1.82 (s, 3H), 1.68 (m, 2H), 1.28 (t, 3H, J=7.2 Hz), 0.98 (d, 3H, J=6.6 Hz), 0.88 (s, 9H), 0.08 (m, 6H).

Synthesis of Intermediate 34

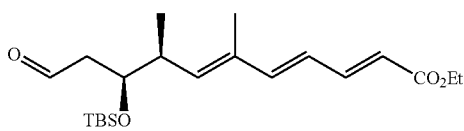 [SMILES: CCOC(=O)/C=C/C=C/C(C)=C/[C@H](C)[C@H](CC=O)O[Si](C)(C)C(C)(C)C]

The alcohol 33 (130 mg, 0.34 mmol) was stirred at room temperature in DCM (3.4 mL) under an inert atmosphere and periodinane (DMP) (288.5 mg, 0.68 mmol) was added in one portion. The reaction was stirred until completion (TLC, about 1 hour) and then was quenched with NaHCO$_3$ (saturated solution), extracted with DCM, washed with brine, dried over magnesium sulphate, filtered and concentrated in vacuum. The product was purified by column chromatography eluting with EtOAc/Hexane 1:4 to yield about 125 mg (yield: 96%) of aldehyde 34 as a colourless oil.

$^1$H-RMN (300 MHz, CDCl$_3$) δ: 9.79 (s, 1H), 7.31 (dd, 1H, J=11.1, 15.3 Hz), 6.52 (d, 1H, J=15.3 Hz), 6.25 (dd, 1H, J=11.1, 15.3 Hz), 5.87 (d, 1H, J=15.3 Hz), 5.48 (d, 1H, J=10.5 Hz), 4.19 (q, 2H, J=7.2 Hz), 4.03 (m, 1H), 2.69 (m, 1H), 2.54 (m, 2H), 1.80 (s, 3H), 1.29 (t, 3H, J=6.9 Hz), 1.01 (d, 3H, J=6.9 Hz), 0.88 (s, 9H), 0.06 (m, 6H).

Synthesis of Intermediate 35

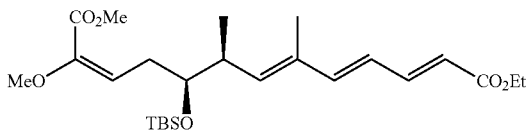 [SMILES: CCOC(=O)/C=C/C=C/C(C)=C/[C@H](C)[C@H](C/C=C(/OC)C(=O)OC)O[Si](C)(C)C(C)(C)C]

To a solution of phosphonate (170 mg, 0.67 mmol) and 18-crown-6 (357 mg, 1.35 mmol) in dry THF (10 mL) stirred under argon atmosphere at −78° C. KHMDS (1.34 ml, 0.67 mmol) was added dropwise. After 15 min a solution of aldehyde 34 (170 mg, 0.45 mmol) in dry THF (8.5 mL) was added dropwise over a period of 30 min and stirred at −78° C. for 90 min. Then, the reaction was quenched with saturated NH$_4$Cl solution, warmed to room temperature and diluted with Dichloromethane. The organic phase was dried (Na$_2$SO$_4$) and evaporated at reduced pressure. Purification by column chromatography (Hexane/EtOAc 20:1 to 10:2) afforded 170 mg (yield: 82%) of (E)-35.

$^1$H-RMN (300 MHz, CDCl$_3$) δ: 7.29 (dd, 1H, J=10.8, 15.3 Hz), 6.50 (d, 1H, J=15.3 Hz), 6.19 (dd, 1H, J=10.8, 15.0 Hz), 5.83 (d, 1H, J=15.3 Hz), 5.48 (d, 1H, J=10.2 Hz), 5.33 (t, 1H, J=7.2 Hz), 4.17 (m, 2H), 3.71 (s, 3H), 3.61 (m, 1H), 3.58 (s, 3H), 2.73 (m, 1H), 2.57 (m, 2H), 1.71 (s, 3H), 1.25 (m, 3H), 0.97 (d, 3H, J=6.7 Hz), 0.88 (s, 9H), 0.03 (m, 6H).

Synthesis of Intermediate 36

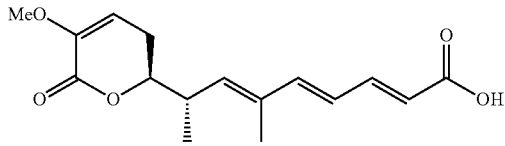 [SMILES: COC1=CC[C@@H]([C@@H](C)/C=C(C)/C=C/C=C/C(=O)O)OC1=O]

LiOH (15.8 mg, 0.66 mmol) was added to a solution of ester 35 (140 mg, 0.30 mmol) in 20% water/Dioxane (7 mL) and the mixture was stirred for 4 hours at 60° C. The mixture was cooled, diluted with DCM and washed with HCl (0.5N, 10 mL). The aqueous phase was repeatedly extracted with DCM and the combined organic layers were dried over Na$_2$SO$_4$, filtered and evaporated to afford the crude di-acid which was used in the next step without further purification.

Concentrated HCl (43 µL) was added to a solution of crude in MeOH (5.2 mL) and the resulting mixture was stirred for 1 hour at room temperature. Then the solvent was removed under reduced pressure and the resulting oil was purified by column chromatography (Hexane/EtOAc 1:4 to EtOAc/MeOH 5:1) affording 72 mg (yield: 70%) of acid 36 as a colourless oil.

$^1$H-RMN (300 MHz, CDCl$_3$) δ: 7.40 (dd, 1H, J=10.8, 15.0 Hz), 6.57 (d, 1H, J=15.0 Hz), 6.31 (dd, 1H, J=11.4, 15.3 Hz), 5.89 (d, 1H, J=15.0 Hz), 5.60 (m, 1H), 5.52 (d, 1H, J=10.2 Hz), 4.22 (m, 1H), 3.64 (s, 3H), 2.90 (m, 1H), 2.38 (m, 2H), 1.84 (s, 3H), 1.15 (d, 3H, J=6.9 Hz).

Synthesis of Compound 37

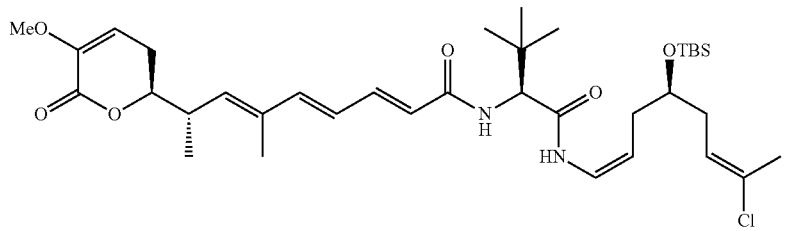 [SMILES: COC1=CC[C@@H]([C@@H](C)/C=C(C)/C=C/C=C/C(=O)N[C@H](C(=O)N/C=C\C[C@H](C/C=C(\C)Cl)O[Si](C)(C)C(C)(C)C)C(C)(C)C)OC1=O]

To a solution of amine 27a (37.6 mg, 0.093 mmol) in DCM/DMF (10:1, 1.3 mL), a solution of acid 36 (30 mg, 0.103 mmol) in dry DCM was added, under argon atmosphere, and then was cooled at 0° C. DIPEA (26 μL, 0.14 mmol), HOAt (12.7 mg, 0.093 mmol), and HATU (35.4 mg, 0.093 mmol) were added to the solution and after 30 min the cold bath was removed. The reaction mixture was stirred at room temperature for 3 h, quenched with a saturated aqueous solution of NH$_4$Cl, poured into water and extracted with DCM. The combined organic phases were dried over Na$_2$SO$_4$, filtered and concentrated. The residue was purified by flash chromatography (Hexane/EtOAc 2:1 to 1:4) to give amide 37 (34.7 mg, yield: 55%) as an oil.

$^1$H NMR (CDCl$_3$, 500 MHz) δ: 7.88 (d, 1H J=10.5 Hz), 7.26 (dd, 1H, J=14.4, 11.4 Hz), 6.72 (dd, 1H, J=9.9, 9.6 Hz), 6.50 (d, 1H, J=15.3 Hz), 6.31-6.22 (m, 2H), 5.94 (d, 1H, J=14.7 Hz), 5.61-5.54 (m, 2H), 5.44 (d, 1H, J=9.9 Hz), 4.87-4.79 (m, 1H), 4.45 (d, 1H, J=9.3), 4.24-4.16 (m, 1H), 3.77-3.44 (m, 1H), 3.64 (s, 3H), 2.96-2.2.81 (m, 1H), 2.39-2.35 (m, 2H), 2.16-2.15 (m, 4H), 2.01 (s, 3H), 1.82 (s, 3H), 1.14 (d, 3H, J=6.6 Hz).1.02 (s, 9H), 0.87 (s, 9H), 0.06 (s, 3H), 0.05 (s, 3H).

Synthesis of Compound 38

J=15.3, 11.1 Hz), 5.99 (d, 1H, J=14.7 Hz), 5.65-5.60 (m, 2H), 5.45 (d, 1H, J=9.9 Hz), 4.87-4.81 (m, 1H), 4.45 (d, 1H, J=9.3), 4.24-4.16 (m, 1H), 3.74-3.64 (m, 1H), 3.64 (s, 3H), 3.22-3.17 (m, 1H), 2.95-2.2.82 (m, 1H), 2.40-2.35 (m, 2H), 2.23-2.16 (m, 4H), 2.05 (s, 3H), 1.81 (s, 3H), 1.13 (d, 3H, J=6.6 Hz), 1.03 (s, 9H).

Synthesis of Compound 3

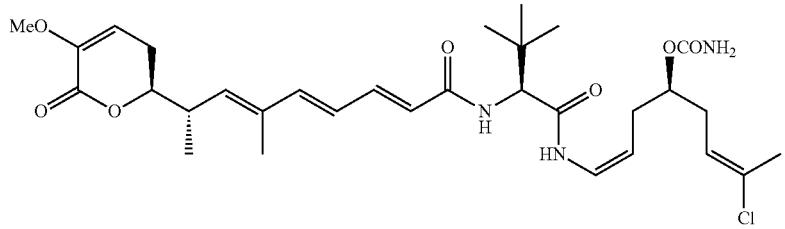

To a solution of compound 38 (20 mg, 0.04 mmol) in Dichloromethane (0.35 ml) at 0° C., trichloroacetyl isocyanate (5.1 μL, 0.04 mmol) was added. The reaction was stirred at 0° C. for 30 min and then neutral aluminium oxide was added. The mixture was stirred for 5-30 min and then was soaked into a pad of aluminium oxide. The product was washed out using a mixture of DCM/MeOH 50:1. The filtrate was evaporated in vacuo to give the crude product which was purified by column chromatography (Hexane/EtOAc 1:1 to 1:3). Compound 3 (13.6 mg, yield: 63%) was obtained as a white foam and exhibited physical and spectroscopic characteristics ($^1$H, $^{13}$C RMN and MS) equivalent to those reported in Example 3.

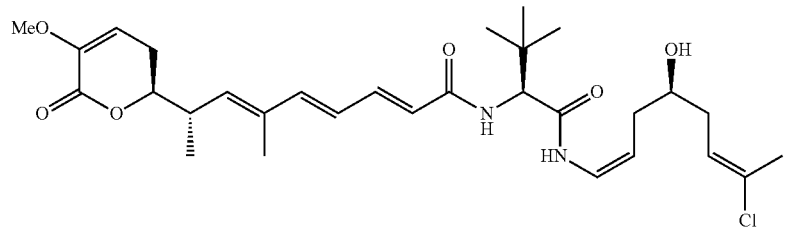 [SMILES: COC1=CC[C@@H]([C@@H](C)/C=C(C)/C=C/C=C/C(=O)N[C@H](C(=O)N/C=C\C[C@@H](O)C/C=C(\C)Cl)C(C)(C)C)OC1=O]

To a solution of 37 (28 mg, 0.04 mmol) in THF (0.6 mL) under N$_2$ and at room temperature, TBAF 1M in THF (83 μL, 0.08 mmol) was added. The reaction was stirred at room temperature for 18 hours and then quenched with saturated aqueous solution of NH$_4$Cl and extracted with EtOAc. The combined organic phases were dried over Na$_2$SO$_4$, filtered and concentrated. The residue was purified by flash chromatography (Hexane/EtOAc 3:1 to 1:2) to give alcohol 38 (22 mg, yield: 96%) as a white solid.

$^1$H NMR (CDCl$_3$, 500 MHz) δ: 9.06 (d, 1H, J=9.9 Hz), 7.24 (dd, 1H, J=14.7, 10.5 Hz), 6.76 (d, 1H, J=9.6 Hz), 6.74 (dd, 1H, J=9.6, 9.6 Hz), 6.50 (d, 1H, J=15.3 Hz), 6.25 (dd, 1H,

Example 10

Scheme 7 depicts a synthetic process for compound 7.

Scheme 7

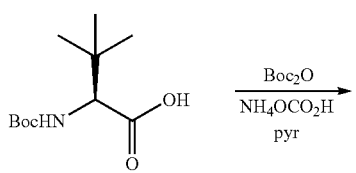

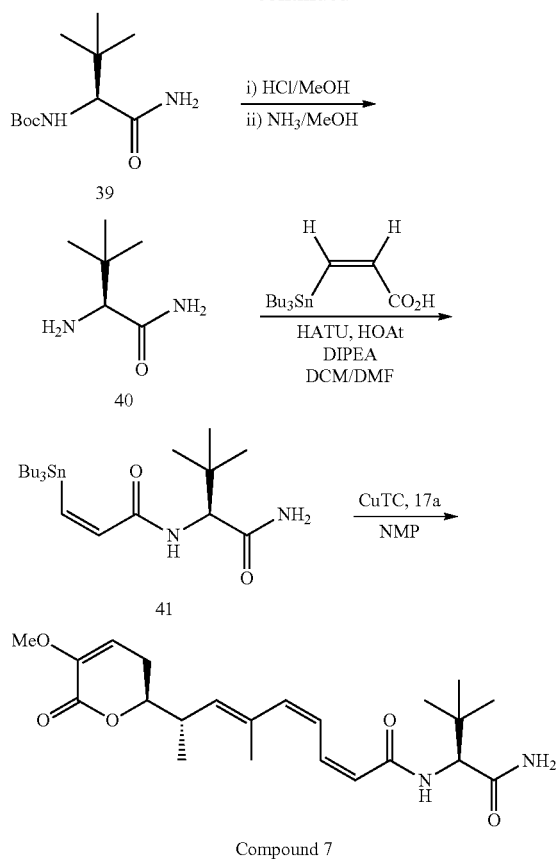

Synthesis of Intermediate 40

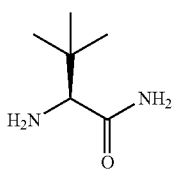

To a solution of Boc-tert-LeuCONH$_2$ 39 (prepared following the procedure described in Pozdnev, V. F., *Tetrahedron Letters* 1995, 36, 7115-7118) (1.9 g, 8.26 mmol) in MeOH, 66 mL of a solution 1.25 M of HCl in MeOH was added. The reaction mixture was stirred for 2 hours at room temperature and then was concentrated at reduced pressure. The solid was then suspended in MeOH and neutralized with concentrated ammonium hydroxide. The solvent was removed by rotary evaporation and the crude was dissolved in dichloromethane. The solution was dried over Na$_2$SO$_4$, filtered and concentrated to give 730 mg (yield: 68%) of the intermediate 40 as a white solid.

$^1$H NMR (CDCl$_3$, 300 MHz) δ: 6.65-6.55 (br s, 1H), 5.65-5.55 (br s, 1H), 3.18 (s, 1H), 1.65-1.55 (br s, 2H), 1.05 (s, 9H).

Synthesis of Intermediate 41

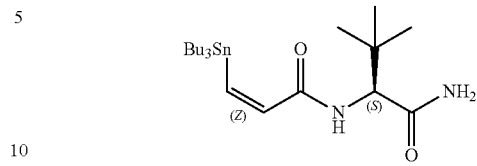

To a solution of amine 40 (100 mg, 0.77 mmol) in DCM/DMF (10:1, 7.7 mL), a solution of (Z)-3-tributylstannylpropenoic acid (306 mg, 0.85 mmol) in dry DCM was added, under argon atmosphere, and then was cooled at 0° C. DIPEA (0.27 mL, 1.54 mmol), HOAt (115.6 mg, 0.85 mmol), and HATU (323 mg, 0.85 mmol) were added to the solution and after 30 min the cold bath was removed. The reaction mixture was stirred at room temperature for 2 h, quenched with a saturated aqueous solution of NH$_4$Cl, poured into water and extracted with DCM. The combined organic phases were dried over Na$_2$SO$_4$, filtered and concentrated. The residue was purified by flash chromatography (Hexane/EtOAc 10:1 to 1:1) to give amide 41 (228 mg, yield: 63%) as a white foam.

$^1$H NMR (CDCl$_3$, 300 MHz) δ: 6.99 (d, 1H, J=12.3 Hz), 6.77 (d, 1H, J=12.3 Hz), 6.47 (d, 1H, J=9.6 Hz), 6.38 (br s, 1H), 6.12 (br s, 1H), 4.46 (d, 1H, J=9.9 Hz), 1.48-1.40 (m, 6H), 1.31-1.19 (m, 12H), 1.00 (s, 9H), 0.89-0.83 (m, 9H).

$^{13}$C NMR (CDCl$_3$, 75 MHz) δ: 173.4, 166.6, 153.4, 136.6, 60.0, 35.0, 29.6, 27.6, 26.8, 14.0, 11.7.

Synthesis of Compound 7

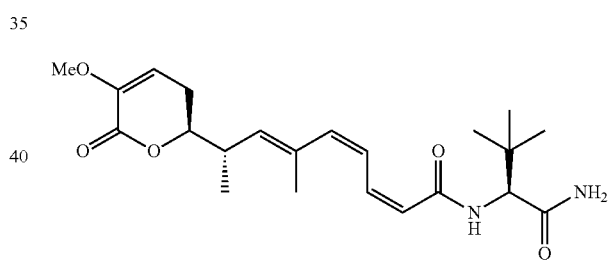

To a solution of alkenylstannane 41 (227.6 mg, 0.48 mmol) and 17a (200.9 mg, 0.58 mmol) in NMP (5 mL) at 0° C., Copper thiophenecarboxylate (19.1 mg, 0.10 mmol) was added. The reaction was stirred at 0° C. for 45 min and 20 min at room temperature. Then, the crude mixture was filtered through a plug of neutral alumina, washed with EtOAc/Ether 50:50 and the combined filtrates were washed with HCl 0.1%. The organic solution was dried and evaporated to give the crude product which was purified by column chromatography (dichloromethane/MeOH 100:1 to 10:1) to give Compound 7 (65.7 mg, yield: 34%) as a white foam. This synthetic product exhibited physical and spectroscopic characteristics ($^1$H, $^{13}$C RMN and MS) equivalent to those reported in Example 3.

The isomer (15R)- of Compound 7 was obtained when a racemic mixture of the amino acid (Boc-tert-LeuCONH$_2$) was used to carry out these reactions. The final mixture of isomers (15 mg) was separated by semipreparative reversed phase HPLC (SymmetryPrep C18 7 μm, 7.8×150 mm, gradient H$_2$O:MeOH from 50 to 70% MeOH in 75 min, UV detection, flow 2.5 mL/min, [rt ((15R)-7): 18.15 min, rt ((15S)-7]): 19.62 min) and it was obtained 3.1 mg of pure (15R)-Compound 7 and 2.9 mg of pure (15S)-Compound 7:

(15R)-Compound 7

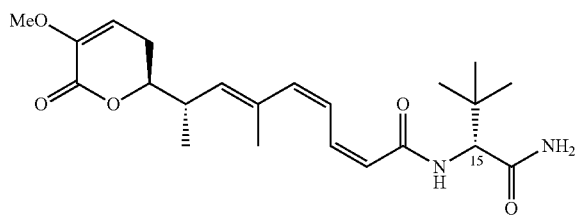 [SMILES: COC1=CC[C@@H]([C@@H](C)/C=C(C)/C=C\C=C/C(=O)N[C@H](C(N)=O)C(C)(C)C)OC1=O]

¹H NMR (MeOD, 500 MHz) δ: 7.23 (dd, 1H, J=12.5, 11.5 Hz), 6.94 (dd, 1H, J=12.5, 11.5 Hz), 6.18 (d, 1H, J=12.0 Hz), 5.91-5.88 (m, 1H), 5.86 (t, 1H, J=4.5 Hz), 5.34 (d, 1H, J=10.0 Hz), 4.33-4.28 (m, 1H), 3.64 (s, 3H), 2.92-2.88 (m, 1H), 2.47-2.44 (m, 2H), 1.85 (s, 3H), 1.17 (d, 3H, J=6.6 Hz), 1.02 (s, 9H).

¹³C NMR (MeOD, 125 MHz) δ: 175.3, 168.6, 164.0, 146.0, 140.8, 138.2, 135.4, 135.4, 125.5, 121.9, 111.1, 83.5, 61.8, 55.9, 38.4, 35.0, 27.2, 27.1, 17.3, 16.8.

Example 11

Scheme 8 depicts the processes for obtaining compounds 42 and 43.

Synthesis of Compound 42

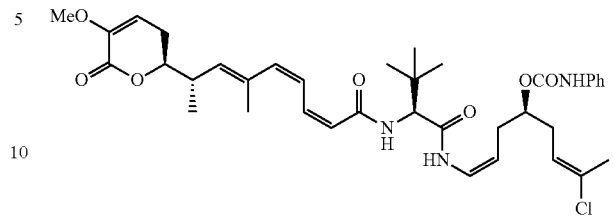

To a solution of alcohol 30a (5 mg, 8.8 mmol) in pyridine (0.45 mL), phenylisocianate (29 mL, 0.27 mmol) was added. The reaction was stirred at room temperature for 20 hours and then quenched with saturated aqueous solution of NH₄Cl and extracted with EtOAc. The combined organic phases were dried over Na₂SO₄, filtered and concentrated. The residue was purified by flash chromatography (Hexane/EtOAc 20:1 to 1:1) to give compound 42 (2.7 mg, yield: 44%) as a white solid.

¹H NMR (CDCl₃, 300 MHz) δ: 8.81-8.77 (m, 1H), 7.46-7.43 (m, 2H), 7.34-7.23 (m, 3H), 7.11-7.06 (m, 2H), 6.88-6.77 (m, 2H), 6.39 (d, 1H, J=9.9 Hz), 6.10 (d, 1H, J=11.7 Hz),

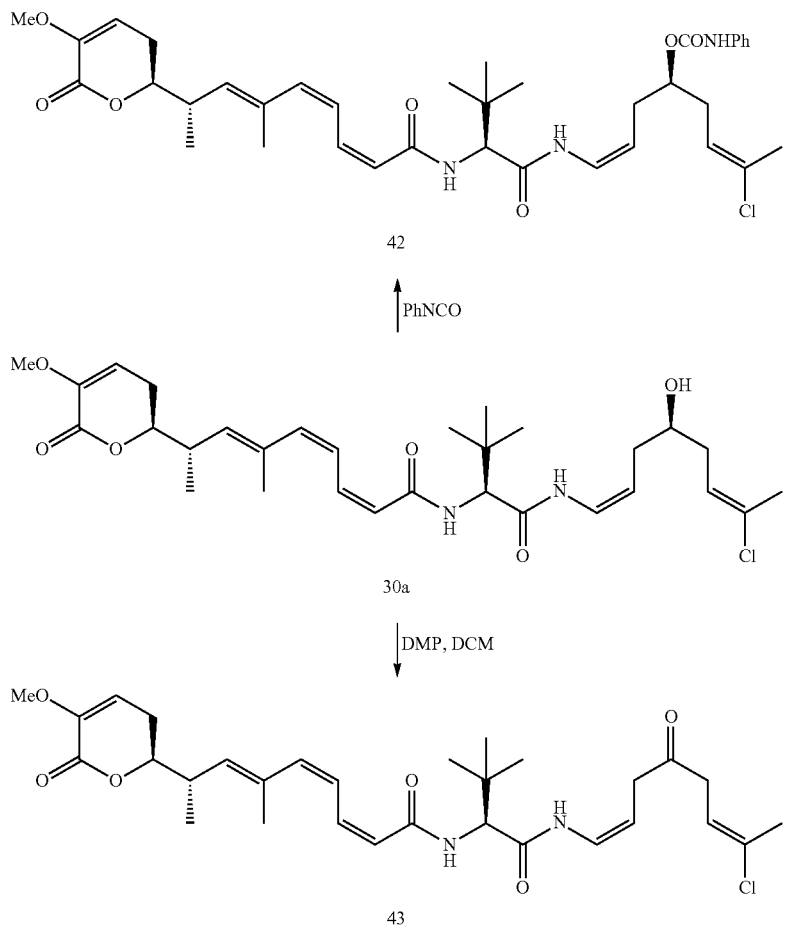

Scheme 8

5.67-5.57 (m, 3H), 5.27 (d, 1H, J=9.9 Hz), 4.85-4.78 (m, 1H), 4.62-4.56 (m, 1H), 4.54 (d, 1H, J=9.3 Hz), 4.25-4.17 (m, 1H), 3.66 (s, 3H), 2.87-2.80 (m, 1H), 2.41-2.38 (m, 5H), 2.21-2.13 (m, 1H), 2.08 (s, 3H), 1.82 (s, 3H), 1.16 (d, 3H J=6.6 Hz), 1.07 (s, 9H).

Synthesis of Compound 43

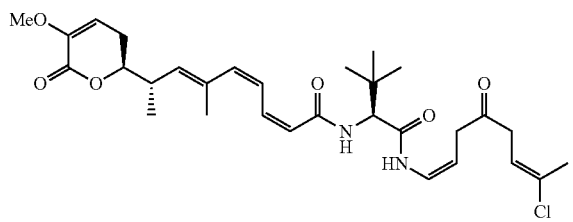 [SMILES: COC1=CC[C@@H]([C@@H](C)/C=C(C)/C=C\C=C/C(=O)N[C@H](C(=O)N/C=C\CC(=O)C/C=C(\C)Cl)C(C)(C)C)OC1=O]

Alcohol 30a (5 mg, 8.88 μmol) was stirred at room temperature in DCM (0.1 mL) under an inert atmosphere and periodinane (7.5 mg, 0.018 mmol) was added in one portion. The reaction was stirred until completion (TLC, about 1 hours) and then was quenched with $NaHCO_3$ (saturated solution), extracted with DCM, washed with brine, dried over magnesium sulphate, filtered and concentrated in vacuum. The product was purified by column chromatography eluting with EtOAc/Hexane 1:1 to yield about 4.5 mg (yield: 90%) of ketone 43 as a colourless oil.

$^1$H NMR (CDCl$_3$, 300 MHz) δ: 8.32 (d, 1H, J=9.9 Hz), 7.31-7.23 (m, 1H), 6.91 (dd, 1H, J=11.7, 11.4 Hz), 6.84 (dd, 1H, J=9.9, 8.7 Hz), 6.26 (d, 1H, J=8.7 Hz), 6.18 (d, 1H, J=11.4 Hz), 5.78-5.73 (m, 1H), 5.68 (d, 1H, J=11.4 Hz), 5.64-5.61 (m, 1H), 5.30-5.27 (m, 1H), 4.94-4.86 (m, 1H), 4.41 (d, 1H, J=9.0 Hz), 4.25-4.17 (m, 1H), 3.66 (s, 3H), 3.18 (dd, 4H, J=18.3, 7.2 Hz), 2.89-2.75 (m, 1H), 2.44-2.38 (m, 2H), 2.04 (s, 3H), 1.84 (s, 3H), 1.16 (d, 3H J=6.9 Hz), 1.05 (s, 9H).

Example 12

Bioassays for the Detection of Antitumor Activity

The aim of this assay is to evaluate the in vitro cytostatic (ability to delay or arrest tumor cell growth) or cytotoxic (ability to kill tumor cells) activity of the samples being tested.

Cell Lines

| Name | N° ATCC | Species | Tissue | Characteristics |
|---|---|---|---|---|
| A549 | CCL-185 | human | lung | lung carcinoma (NSCLC) |
| HT29 | HTB-38 | human | colon | colorectal adenocarcinoma |
| MDA-MB-231 | HTB-26 | human | breast | breast adenocarcinoma |

Evaluation of Cytotoxic Activity Using the SBR Colorimetric Assay

A colorimetric type of assay, using sulforhodamine B (SRB) reaction has been adapted for a quantitative measurement of cell growth and viability (following the technique described by Skehan P et al. J. Natl. Cancer Inst. 1990, 82, 1107-1112).

This form of assay employs SBS-standard 96-well cell culture microplates (Faircloth et al. Methods in cell science, 1988, 11(4), 201-205; Mosmann et al, Journal of. Immunological. Methods, 1983, 65(1-2), 55-63). All the cell lines used in this study, derived from different types of human cancer, were obtained from the American Type Culture Collection (ATCC).

Cells were maintained in Dulbecco's Modified Eagle Medium (DMEM) supplemented with 10% Fetal Bovine Serum (FBS), 2 mM L-glutamine, 100 U/mL penicillin and 100 U/mL streptomycin at 37° C., 5% $CO_2$ and 98% humidity. For the experiments, cells were harvested from subconfluent cultures using trypsinization and resuspended in fresh medium before counting and plating.

Cells were seeded in 96 well microtiter plates at $5\times10^3$ cells per well in aliquots of 150 μL, and allowed to attach to the plate surface for 18 hours in drug free medium. One control (untreated) plate of each cell line was fixed (as described below) and used for time zero reference value. Afterwards, test samples were added to the cultures in ten serial dilutions, in aliquots of 50 μL, ranging from 10 to 0.00262 μg/mL. After 48 hours exposure, the antitumor effect was estimated by the SRB method: Briefly, cells were washed twice with PBS, fixed for 15 min in 1% glutaraldehyde solution, rinsed twice in PBS, and stained in 0.4% SRB solution for 30 min at room temperature. Cells were then rinsed several times with 1% acetic acid solution and air-dried. SRB was then extracted in 10 mM trizma base solution and the absorbance measured in an automated spectrophotometric plate reader at 490 nm. Cell survival was expressed as percentage of control cell growth. The final effect of the sample being tested was estimated by applying the NCI algorithm (Boyd M R and Paull K D. Drug Dev. Res. 1995, 34, 91-104).

Using the mean±SD of triplicate cultures, a dose-response curve was automatically generated using nonlinear regression analysis. Three reference parameters were calculated (NCI algorithm) by automatic interpolation: $GI_{50}$=concentration that produces 50% growth inhibition; TGI=total growth inhibition (cytostatic effect) and $LC_{50}$=concentration that produces 50% net cell killing (cytotoxic effect).

Anti-Mitotic Assay Protocol

The mitotic ratio of the cell cultures (percentage of cells arrested in mitosis) was estimated using a specific 96-well microplate immunoassay that quantitatively detects a specific mitotic marker. HeLa cells (h-cervix carcinoma, ATCC# CCL-2) were incubated for 18 hours in the presence or absence of the samples being tested. Afterwards, cells were washed with PBS and lysed on ice in 75 μL of freshly prepared lysis buffer (1 mM EGTA (pH 7.5), 0.5 mM PMSF and 1 mM $NaVO_3$) for 30 min. An aliquot of the cell extract (60 μL) was transferred to a high-binding surface ELISA plate and dried in a speed-vac for 2 h at room temperature. Plates were then blocked in 100 μL. PBS-1% BSA for 30 min at 30° C. and sequentially incubated with anti-MPM2 primary mouse monoclonal antibody (*Upstate Biotechnology*, cat #05-368) for 18 h at 4° C. and appropriate peroxidase-conjugated secondary antibody for 1 h at 30° C. After intensive washing in 0.02% Tween-20, peroxidase reaction were performed using 30 μL of TMB (3,3',5,5'-tetramethyl-benzidine) for 30 min at 30° C. Reaction was stopped by adding 30 μL of a 4% $H_2SO_4$ solution. Assay was quantified by measuring the O.D. at 450 nm in a microplate spectrophotometer. Results were expressed as $IC_{50}$, sample concentration that produces 50% mitotic arrest in treated cell cultures, as compared to control, untreated cultures.

Tables 9 and 10 illustrate data on the biological activity of compounds of the present invention.

TABLE 9

Cytotoxicity assay - Activity Data (Molar)

|  |  | Compound 1 | Compound 2 | Compound 3 | Compound 4 |
|---|---|---|---|---|---|
| MDA-MB-231 | $GI_{50}$ | 4.45E-10 | 9.85E-09 | 9.24E-10 | 6.13E-10 |
|  | TGI | 9.90E-10 | 2.15E-08 | 2.47E-09 | 1.49E-09 |
|  | $LC_{50}$ | 2.80E-09 | 7.20E-08 | 9.57E-09 | 8.23E-09 |
| HT29 | $GI_{50}$ | 4.62E-10 | 8.31E-09 | 4.45E-10 | <4.31E-10 |
|  | TGI | 6.10E-10 | 1.09E-08 | 7.59E-10 | 9.28E-10 |
|  | $LC_{50}$ | 9.90E-10 | 1.72E-08 | >1.65E-07 | 1.12E-09 |
| A549 | $GI_{50}$ | 3.79E-10 | 8.63E-09 | 1.02E-09 | 5.95E-10 |
|  | TGI | 1.09E-09 | 2.37E-08 | 4.29E-09 | 2.45E-09 |
|  | $LC_{50}$ | >1.65E-07 | 1.65E-05 | >1.65E-07 | >1.64E-06 |

|  |  | Compound 5 | Compound 6 | Compound 7 | Compound 8 |
|---|---|---|---|---|---|
| MDA-MB-231 | $GI_{50}$ | 1.03E-10 | 4.90E-10 | 4.20E-07 | 3.46E-09 |
|  | TGI | 4.56E-10 | 3.21E-09 | 8.41E-07 | 1.01E-08 |
|  | $LC_{50}$ | 4.90E-09 | 1.55E-08 | 2.45E-06 | 4.12E-08 |
| HT29 | $GI_{50}$ | 4.39E-11 | 5.91E-10 | 4.20E-07 | 2.14E-09 |
|  | TGI | 1.28E-10 | 1.01E-09 | 5.44E-07 | 3.13E-09 |
|  | $LC_{50}$ | >1.69E-07 | 4.90E-09 | 8.16E-07 | 6.27E-09 |
| A549 | $GI_{50}$ | 6.08E-11 | 7.60E-10 | 6.18E-07 | 3.63E-09 |
|  | TGI | 3.21E-10 | >1.64E-06 | 1.19E-06 | 1.30E-08 |
|  | $LC_{50}$ | >1.69E-07 | >1.64E-06 | >2.47E-06 | >1.65E-06 |

|  |  | Compound 29a | Compound 29d | Compound 29e | Compound 30a |
|---|---|---|---|---|---|
| MDA-MB-231 | GI50 | 1.18E-06 | 1.10E-06 | 1.14E-06 | 1.95E-09 |
|  | TGI | 2.80E-06 | 1.39E-06 | 1.48E-06 | 9.41E-09 |
|  | LC50 | 6.20E-06 | 1.83E-06 | 2.07E-06 | 8.52E-08 |
| HT29 | GI50 | 6.05E-07 | 8.29E-07 | 2.07E-06 | 1.35E-09 |
|  | TGI | 1.42E-06 | 8.72E-07 | 2.21E-06 | 2.13E-09 |
|  | LC50 | 4.43E-06 | 9.28E-07 | 2.36E-06 | 1.01E-08 |
| A549 | GI50 | 8.86E-07 | 4.64E-07 | 1.15E-06 | 2.31E-09 |
|  | TGI | 3.40E-06 | 8.01E-07 | 1.77E-06 | 1.37E-07 |
|  | LC50 | 8.56E-06 | 1.38E-06 | 2.66E-06 | >1.78E-06 |

|  |  | Compound 30b | Compound 30c | Compound 30d | Compound 30f |
|---|---|---|---|---|---|
| MDA-MB-231 | $GI_{50}$ | 2.08E-08 | 9.83E-10 | 3.10E-10 | 6.94E-07 |
|  | TGI | 5.11E-07 | 5.83E-09 | 7.03E-10 | 1.07E-06 |
|  | $LC_{50}$ | 5.11E-06 | 5.28E-08 | >1.67E-08 | 1.61E-06 |
| HT29 | $GI_{50}$ | 9.84E-09 | 4.74E-10 | 1.32E-10 | 4.88E-07 |
|  | TGI | 9.27E-07 | 8.38E-10 | 2.51E-10 | 7.13E-07 |
|  | $LC_{50}$ | 4.73E-06 | >1.82E-07 | >1.67E-08 | 1.05E-06 |
| A549 | $GI_{50}$ | 2.27E-08 | 7.10E-10 | 3.18E-10 | 4.88E-07 |
|  | TGI | 3.22E-07 | 3.10E-09 | 1.06E-09 | 6.57E-07 |
|  | $LC_{50}$ | >1.89E-05 | >1.82E-07 | >1.67E-08 | 9.19E-07 |

|  |  | Compound 30e | Compound 31 | Compound 37 | Compound 38 |
|---|---|---|---|---|---|
| MDA-MB-231 | $GI_{50}$ | 2.31E-08 | 7.50E-11 | 3.10E-06 | 6.04E-08 |
|  | TGI | 6.57E-08 | 1.50E-10 | 5.61E-06 | >1.78E-07 |
|  | $LC_{50}$ | 2.66E-07 | 3.59E-10 | >1.48E-05 | >1.78E-07 |
| HT29 | $GI_{50}$ | 1.35E-08 | 4.06E-11 | 1.92E-06 | 3.91E-08 |
|  | TGI | 2.13E-08 | 1.02E-10 | 2.95E-06 | 6.39E-08 |
|  | $LC_{50}$ | 4.44E-08 | >1.56E-08 | 1.00E-05 | >1.78E-07 |
| A549 | $GI_{50}$ | 3.55E-08 | 9.22E-11 | 3.54E-06 | 4.62E-08 |
|  | TGI | 3.02E-07 | 2.19E-10 | 6.64E-06 | 6.75E-08 |
|  | $LC_{50}$ | 3.55E-06 | >1.56E-08 | 1.39E-05 | >1.78E-07 |

|  |  | Compound (21S)-1 | Compound (21S)-5 | Compound (15R)-7 | Compound (21S)-30a |
|---|---|---|---|---|---|
| MDA-MB-231 | $GI_{50}$ | 1.65E-09 | 4.56E-09 | 7.66E-07 | 2.49E-09 |
|  | TGI | 5.77E-09 | 1.86E-08 | 2.47E-06 | 2.13E-08 |
|  | $LC_{50}$ | 3.46E-08 | 1.03E-07 | >2.47E-05 | 2.84E-07 |
| HT29 | $GI_{50}$ | 8.91E-10 | 2.53E-09 | 3.46E-07 | 2.66E-09 |
|  | TGI | 1.63E-09 | 2.87E-09 | 5.93E-07 | 3.02E-09 |
|  | $LC_{50}$ | 2.31E-08 | 3.88E-09 | 1.31E-06 | >1.63E-06 |
| A549 | $GI_{50}$ | 2.14E-09 | 6.92E-09 | 1.04E-06 | 3.73E-09 |
|  | TGI | 4.29E-08 | 2.87E-08 | 3.46E-06 | 1.95E-07 |
|  | $LC_{50}$ | >1.65E-06 | >1.69E-06 | >2.47E-05 | >1.63E-06 |

TABLE 10

Antimitotic assay - Activity Data (Molar) of Compounds 1 and 2.

|  | $IC_{50}$ |
|---|---|
| Compound 1 | 2.64E-8 |
| Compound 2 | 2.64E-8 |

The invention claimed is:

1. A method of treating an individual affected by cancer comprising administering to said affected individual a therapeutically effective amount of a compound of general formula I

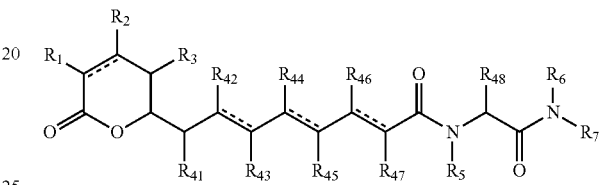

(I)

wherein $R_1$ is hydrogen or unsubstituted $C_1$-$C_{12}$ alkoxy; $R_2$, $R_3$, $R_{42}$, $R_{44}$, $R_{45}$, $R_{46}$, and $R_{47}$ are hydrogen; $R_{41}$ and $R_{43}$ are hydrogen or unsubstituted $C_1$-$C_{12}$ alkyl; $R_{48}$ is selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl; each $R_5$, $R_6$, and $R_7$ are independently selected from hydrogen, $COR_a$, $COOR_a$, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, or $R_5$ and $R_{48}$ together with the corresponding N atom and C atom to which they are attached may form a substituted or unsubstituted heterocyclic group; $R_a$ is selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl and substituted or unsubstituted heterocyclic group; and each dotted line represent an optional additional bond; or a tautomer or stereoisomer thereof.

2. The method according to claim 1, wherein, in the compound of formula I, $R_1$ is selected from hydrogen, —$OR_a$ and —$OCOR_a$, wherein $R_a$ is selected from hydrogen and substituted or unsubstituted $C_1$-$C_6$ alkyl, or a tautomer or stereoisomer thereof.

3. The method according to claim 2, wherein, in the compound of formula I, $R_1$ is hydrogen or methoxy, or a tautomer or stereoisomer thereof.

4. The method according to claim 1, wherein, in the compound of formula I, $R_{41}$, $R_{43}$, and $R_{48}$ groups are independently selected from hydrogen and unsubstituted $C_1$-$C_6$ alkyl, or a tautomer or stereoisomer thereof.

5. The method according to claim 4, wherein, in the compound of formula I, $R_{41}$, $R_{43}$, and $R_{48}$ groups are independently selected from hydrogen, unsubstituted methyl, unsubstituted isopropyl and unsubstituted tert-butyl, or a tautomer or stereoisomer thereof.

6. The method according to claim 4, wherein, in the compound of formula I, $R_{41}$ and $R_{43}$ are methyl, or a tautomer or stereoisomer thereof.

7. The method according to claim 6, wherein, in the compound of formula I, $R_{48}$ is selected from isopropyl, tert-butyl, and benzyl, or a tautomer or stereoisomer thereof.

8. The method according to claim 1, wherein, in the compound of formula I, $R_5$ and $R_6$ are each independently selected from the group consisting of hydrogen and substituted or unsubstituted $C_1$-$C_6$ alkyl, or a tautomer or stereoisomer thereof.

9. The method according to claim 8, wherein, in the compound of formula I, $R_5$ and $R_6$ are hydrogen, or a tautomer or stereoisomer thereof.

10. The method according to claim 1, wherein, in the compound of formula I, $R_7$ is selected from hydrogen, substituted or unsubstituted $C_1$-$C_{12}$ alkyl and substituted or unsubstituted $C_2$-$C_{12}$ alkenyl, or a tautomer or stereoisomer thereof.

11. The method according to claim 10, wherein, in the compound of formula I, $R_7$ is selected from hydrogen and substituted $C_2$-$C_{12}$ alkenyl, or a tautomer or stereoisomer thereof.

12. The method according to claim 11, wherein, in the compound of formula I, $R_7$ is an alkenyl group that is substituted in one or more positions with halogen, OR', =O, OCOR', OCONHR', OCON(R')$_2$ and protected OH, wherein each of the R' groups is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, and substituted or unsubstituted aryl, or a tautomer or stereoisomer thereof.

13. The method according to claim 1, wherein, in the compound of formula I, an additional bond is present in all the places indicated with a dotted line, or a tautomer or stereoisomer thereof.

14. The method according to claim 1, wherein the compound of formula I is selected from:

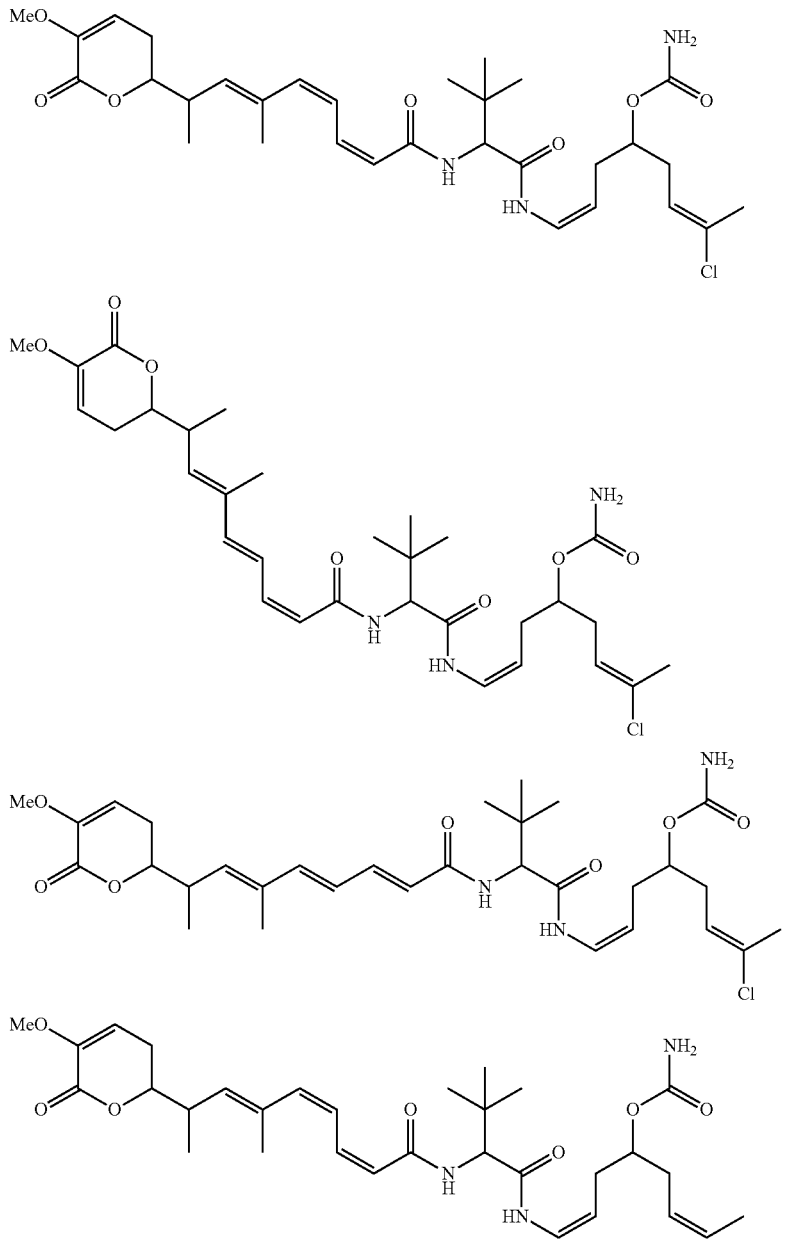

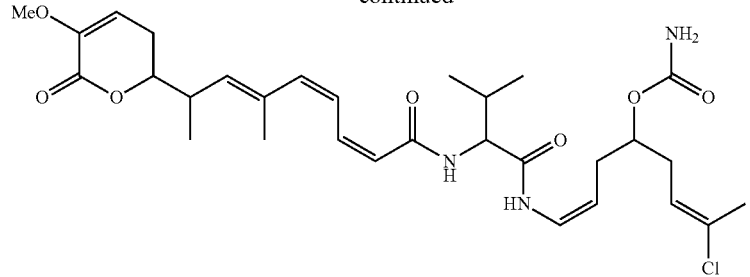
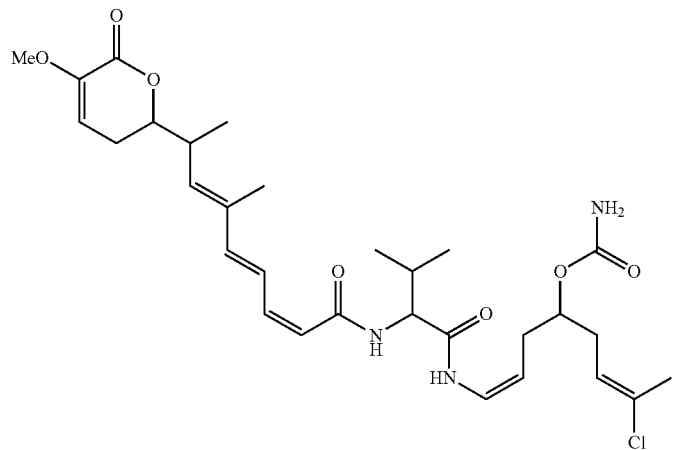
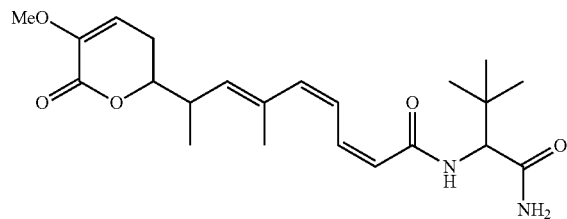
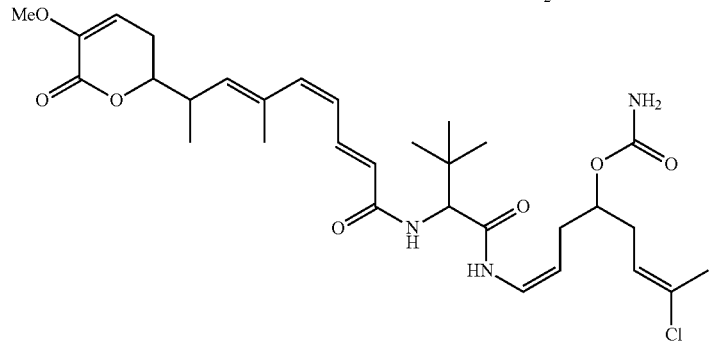
or a tautomer, or stereoisomer thereof.
15. The method according to claim 1, wherein the compound of formula I is selected from:
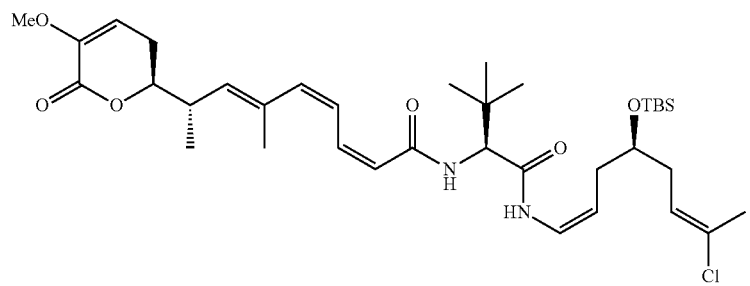

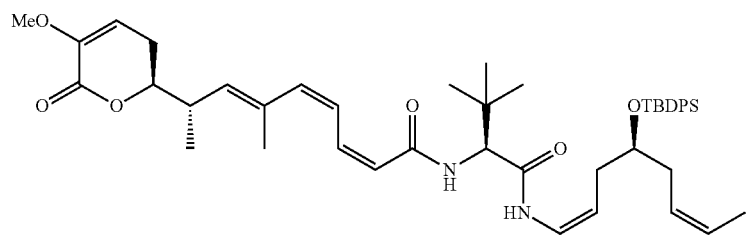
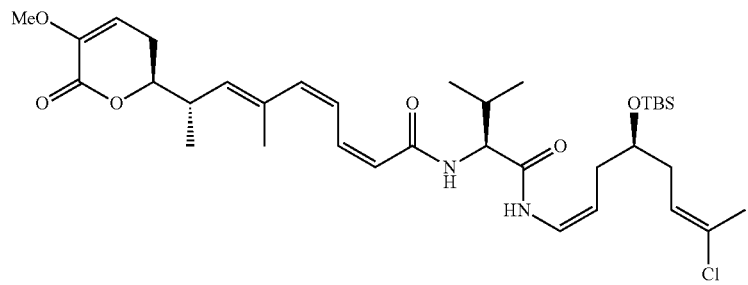
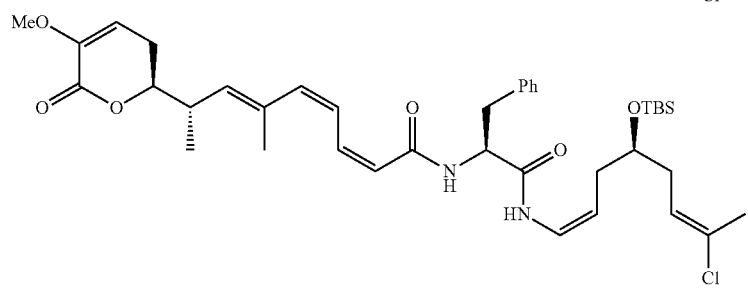
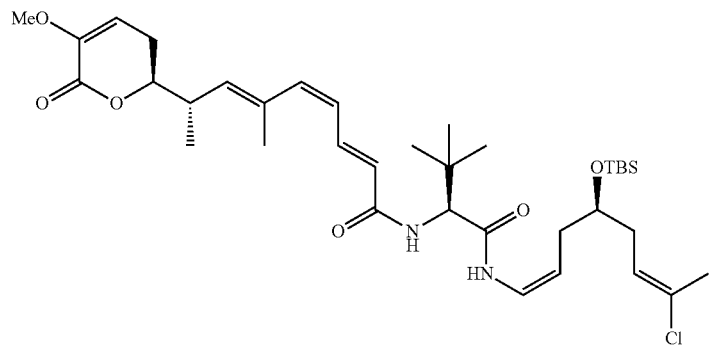
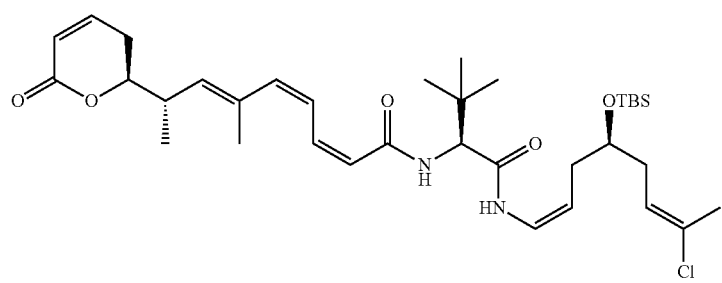
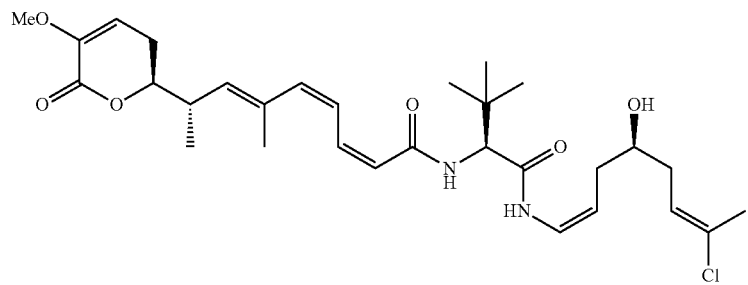

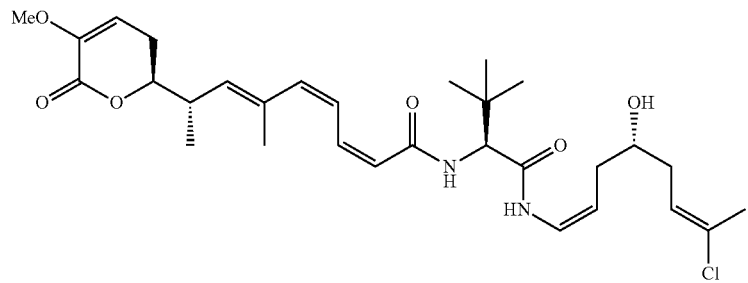
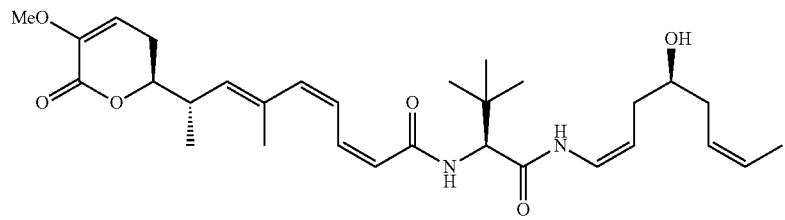
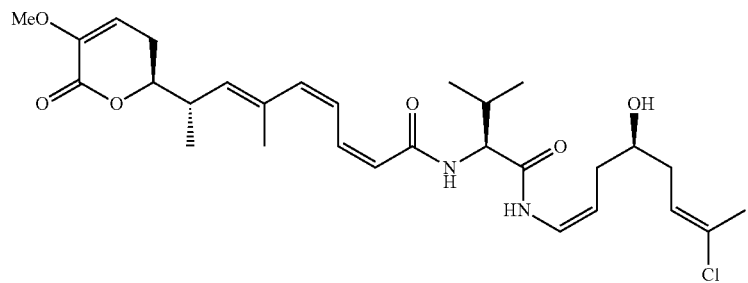
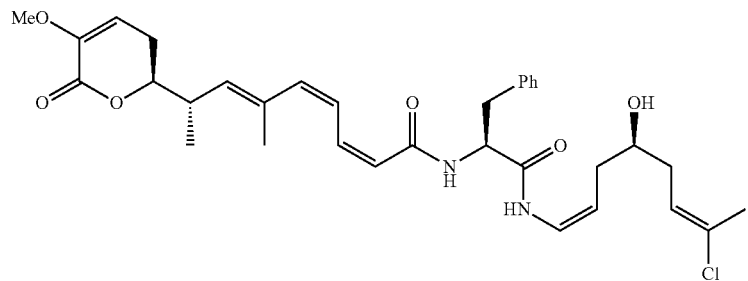
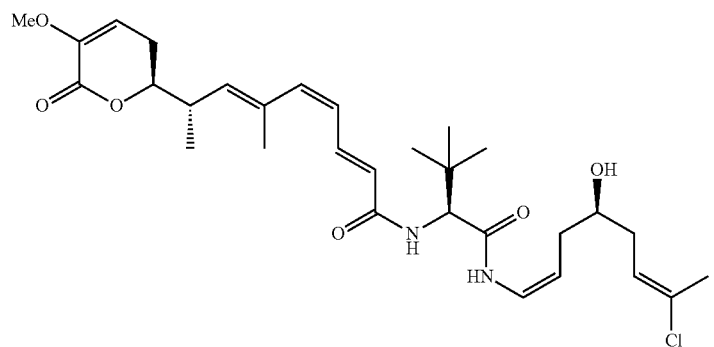

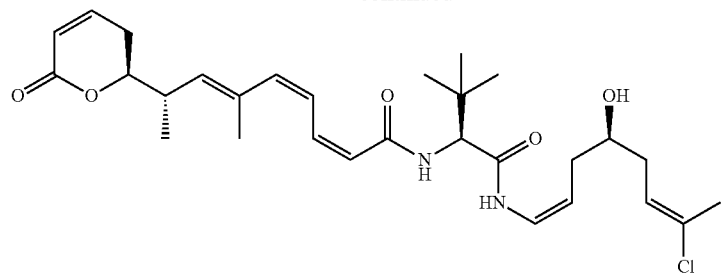
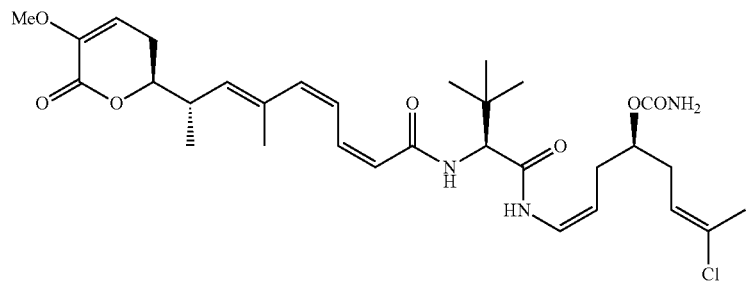
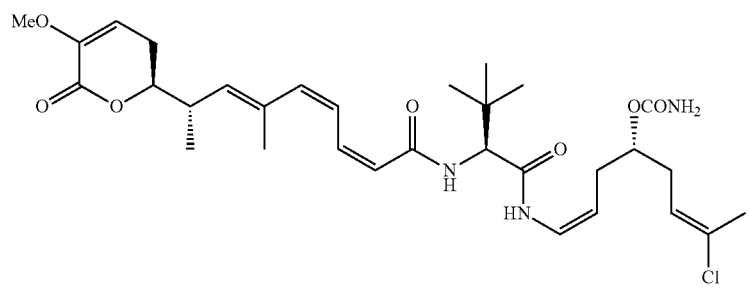
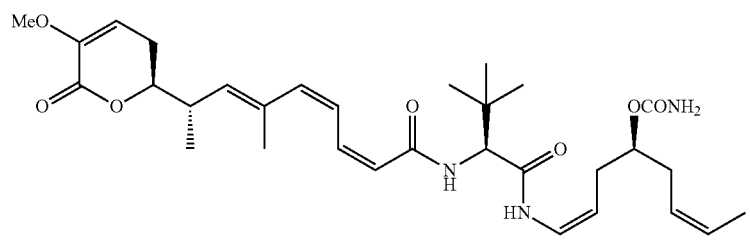
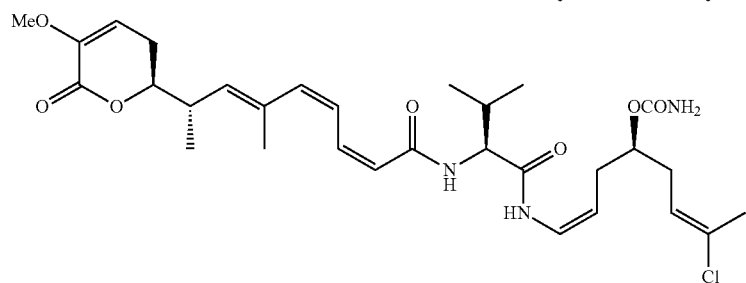
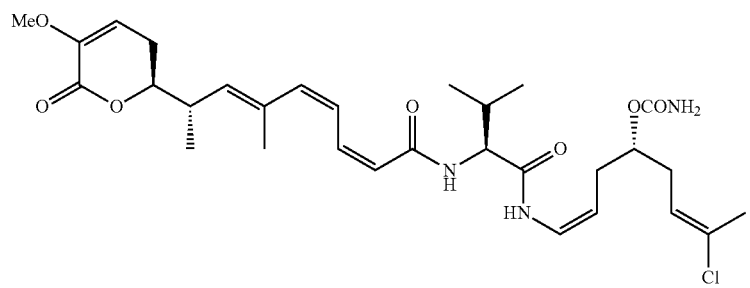

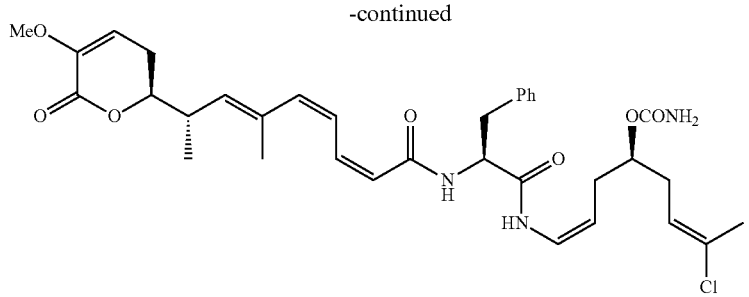
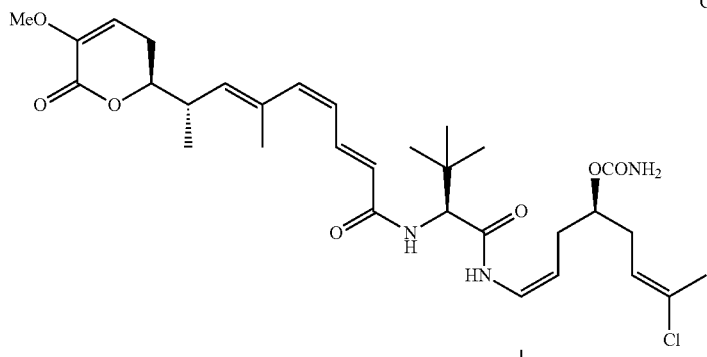
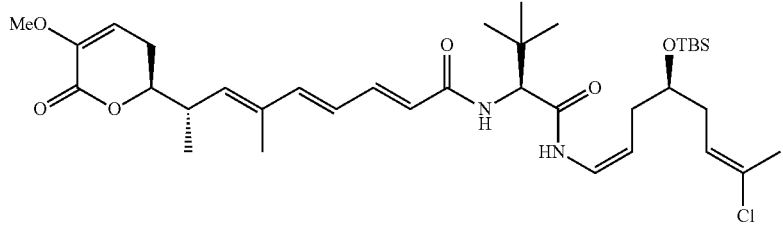
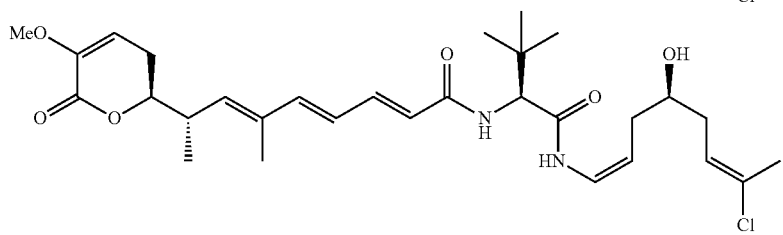
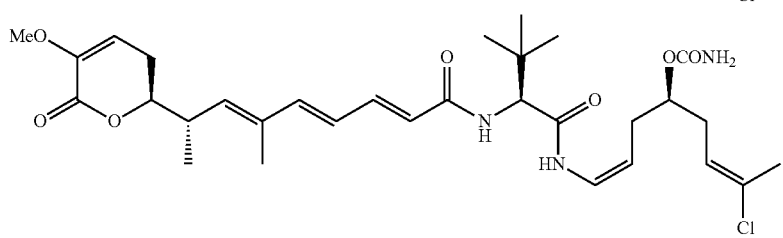
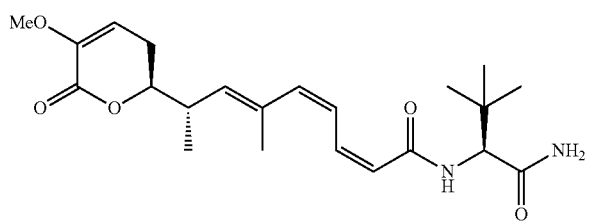
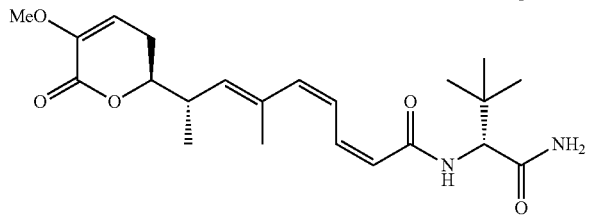

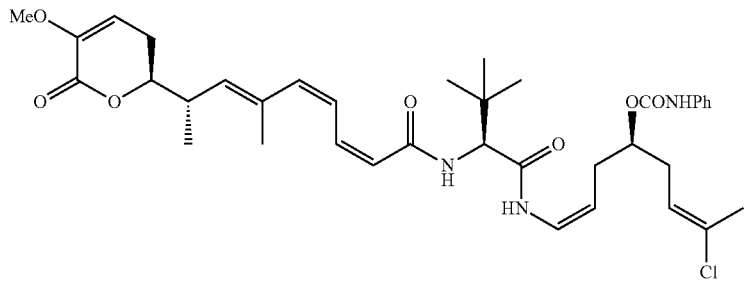

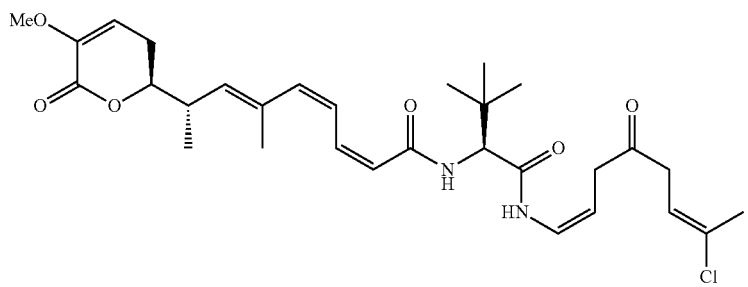

or a tautomer thereof.

16. The method according to claim 1, wherein the compound of formula I has the following formula

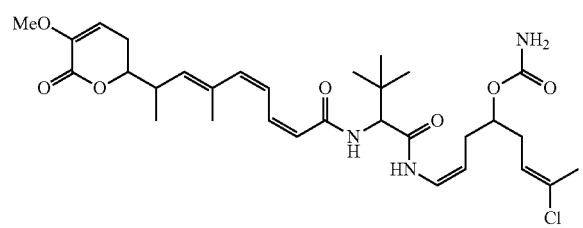 [SMILES: COC1=CCC(C(C)/C=C(C)/C=C\C=C/C(=O)NC(C(=O)N/C=C\CC(C/C=C(\C)Cl)OC(N)=O)C(C)(C)C)OC1=O]

or a tautomer or stereoisomer thereof.

17. The method according to claim 1, wherein the compound of formula I has the following formula

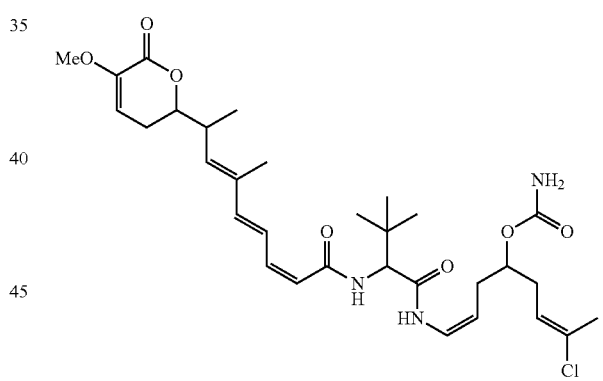

or a tautomer or stereoisomer thereof.

18. The method according to claim 1, wherein the compound of formula I has the following formula

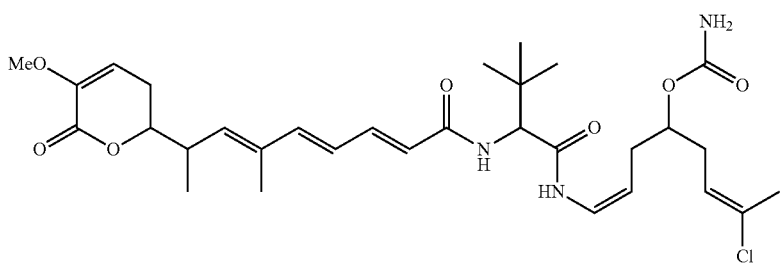 [SMILES: COC1=CCC(C(C)/C=C(C)/C=C/C=C/C(=O)NC(C(=O)N/C=C\CC(C/C=C(\C)Cl)OC(N)=O)C(C)(C)C)OC1=O]

or a tautomer or stereoisomer thereof.

19. The method according to claim 1, wherein the compound of formula I has the following formula

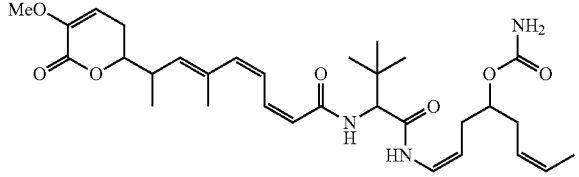 [SMILES: C/C=C\CC(C/C=C\NC(=O)C(NC(=O)\C=C/C=C\C(C)=C\C(C)C1CC=C(OC)C(=O)O1)C(C)(C)C)OC(N)=O]

or a tautomer or stereoisomer thereof.

20. The method according to claim 1, wherein the compound of formula I has the following formula

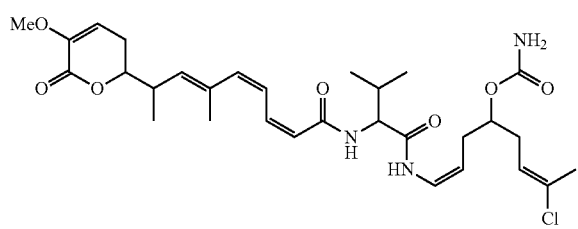 [SMILES: COC1=CCC(C(C)/C=C(C)/C=C\C=C/C(=O)NC(C(=O)N/C=C\CC(C/C=C(\C)Cl)OC(N)=O)C(C)C)OC1=O]

or a tautomer or stereoisomer thereof.

21. The method according to claim 1, wherein the compound of formula I has the following formula or a tautomer or stereoisomer thereof.

22. The method according to claim 1, wherein the compound of formula I has the following formula

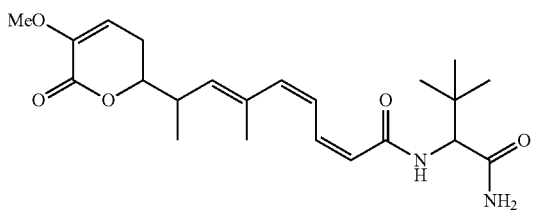 [SMILES: COC1=CCC(C(C)/C=C(C)/C=C\C=C/C(=O)NC(C(N)=O)C(C)(C)C)OC1=O]

or a tautomer or stereoisomer thereof.

23. The method according to claim 1, wherein the compound of formula I has the following formula or a tautomer or stereoisomer thereof.

24. The method according to claim 1, wherein the compound of formula I has the following formula or a tautomer thereof.

25. The method according to claim 1, wherein the compound of formula I has the following formula or a tautomer thereof.

26. The method according to claim 1, wherein the compound of formula I has the following formula

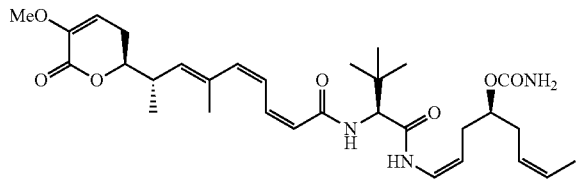

or a tautomer thereof.

27. The method according to claim 1, wherein the compound of formula I has the following formula

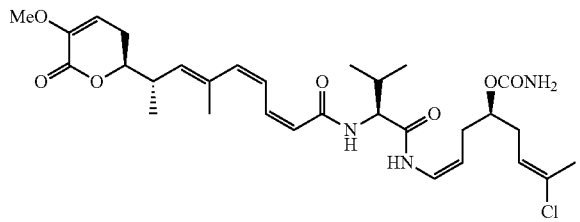

or a tautomer thereof.

28. The method according to claim 1, wherein the compound of formula I has the following formula

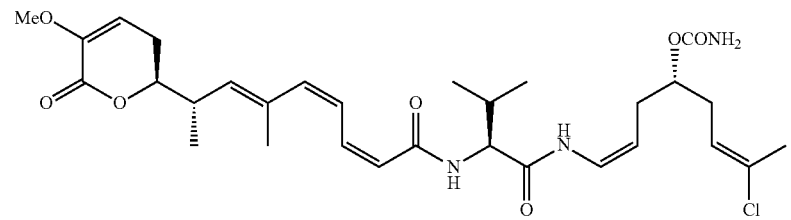

or a tautomer thereof.

29. The method according to claim 1, wherein the compound of formula I has the following formula

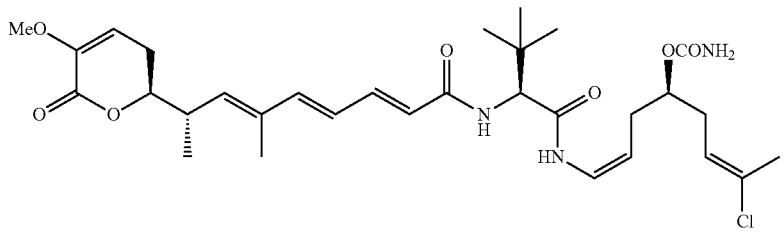

or a tautomer thereof.

30. The method according to claim 1, wherein the compound of formula I has the following formula or a tautomer thereof.

31. The method according to claim 1, wherein the compound of formula I has the following formula or a tautomer thereof.

32. The method according to claim 1, wherein the compound of formula I has the following formula

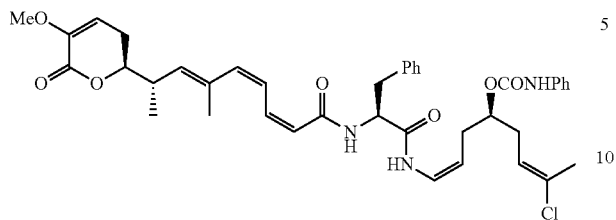

or a tautomer thereof.

33. The method according to claim 1, wherein, in the compound of formula I, $R_{48}$ is substituted $C_1$-$C_6$ alkyl, or a tautomer or stereoisomer thereof.

34. The method according to claim 33, wherein, in the compound of formula I, $R_{48}$ is selected from substituted methyl, substituted isopropyl, and substituted tert-butyl, or a tautomer, or stereoisomer thereof.

35. The method according to claim 34, wherein, in the compound of formula I, $R_{48}$ is selected from isopropyl, tert-butyl and benzyl, or tautomer or stereoisomer thereof.

* * * * *